(12) United States Patent
Asher et al.

(10) Patent No.: US 10,561,436 B2
(45) Date of Patent: Feb. 18, 2020

(54) SURGICAL INSTRUMENT USE INDICATOR

(71) Applicant: Ethicon LLC, Guaynabo, PR (US)

(72) Inventors: Ryan M. Asher, Cincinnati, OH (US);
Brian D. Black, Loveland, OH (US);
Chad P. Boudreaux, Cincinnati, OH (US); Nathan Cummings, Blue Ash, OH (US); William D. Dannaher, Cincinnati, OH (US); Craig T. Davis, Cincinnati, OH (US); Glenn W. Ellison, Maineville, OH (US);
Frederick L. Estera, Cincinnati, OH (US); Jacob S. Gee, Cincinnati, OH (US); Geni Giannotti, Cincinnati, OH (US); Timothy S. Holland, Cincinnati, OH (US); Kevin L. Houser, Springboro, OH (US); Gregory W. Johnson, Milford, OH (US); Amy M. Krumm, Cincinnati, OH (US); Jason R. Lesko, Cincinnati, OH (US);
Stephen M. Leuck, Cincinnati, OH (US); Ion V. Nicolaescu, Carpentersville, IL (US); Candice Otrembiak, Loveland, OH (US);
Amelia A. Pierce, Cincinnati, OH (US); Eric Roberson, Cincinnati, OH (US); Shan Wan, Mason, OH (US)

(73) Assignee: Ethicon LLC, Guaynabo, PR (US)

( * ) Notice: Subject to any disclaimer, the term of this patent is extended or adjusted under 35 U.S.C. 154(b) by 233 days.

(21) Appl. No.: 15/664,244

(22) Filed: Jul. 31, 2017

(65) Prior Publication Data
US 2019/0029707 A1    Jan. 31, 2019

(51) Int. Cl.
*A61B 17/32*    (2006.01)
*A61B 17/00*    (2006.01)

(52) U.S. Cl.
CPC ............... *A61B 17/320068* (2013.01); *A61B 2017/00473* (2013.01); *A61B 2017/00477* (2013.01); *A61B 2017/320071* (2017.08)

(58) Field of Classification Search
CPC .... A61B 17/320068; A61B 17/320092; A61B 2090/0803; A61B 2017/2929;
(Continued)

(56) References Cited

U.S. PATENT DOCUMENTS

| 5,059,210 A | 10/1991 | Clark et al. |
| 5,313,935 A | 5/1994 | Kortenbach et al. |

(Continued)

FOREIGN PATENT DOCUMENTS

| EP | 2 371 314 A2 | 10/2011 |
| EP | 2 478 861 A2 | 7/2012 |
| EP | 2 932 913 A1 | 10/2015 |

OTHER PUBLICATIONS

U.S. Appl. No. 15/644,930, filed Jul. 10, 2017.
(Continued)

*Primary Examiner* — Julian W Woo
(74) *Attorney, Agent, or Firm* — Frost Brown Todd LLC

(57) ABSTRACT

An ultrasonic instrument includes a housing, an ultrasonic transducer support by the housing, and an integrated usage indicator. The housing is configured to removably connect to a shaft assembly. The ultrasonic transducer is configured to be acoustically connected to a waveguide and operated a predetermined number of use cycles. The integrated usage indicator is operatively connected to the housing and includes a used state indicator. The used state indicator is configured to indicate to a clinician in a used state when the ultrasonic transducer has been operated at least the prede- (Continued)

termined number of use cycles for limiting usage of the ultrasonic transducer to the predetermined number of use cycles.

20 Claims, 42 Drawing Sheets

(58) Field of Classification Search
CPC .. A61B 2017/0046; A61B 2017/00477; A61B 2017/00473; A61B 2017/320071
See application file for complete search history.

(56) References Cited

U.S. PATENT DOCUMENTS

| | | | |
|---|---|---|---|
| 5,318,570 A * | 6/1994 | Hood | A61B 17/8847 601/2 |
| 5,322,055 A | 6/1994 | Davison et al. | |
| 5,792,135 A | 8/1998 | Madhani et al. | |
| 5,817,084 A | 10/1998 | Jensen | |
| 5,873,873 A | 2/1999 | Smith et al. | |
| 5,878,193 A | 3/1999 | Wang et al. | |
| 5,980,510 A | 11/1999 | Tsonton et al. | |
| 6,231,565 B1 | 5/2001 | Tovey et al. | |
| 6,283,981 B1 | 9/2001 | Beaupre | |
| 6,309,400 B2 | 10/2001 | Beaupre | |
| 6,325,811 B1 | 12/2001 | Messerly | |
| 6,364,888 B1 | 4/2002 | Niemeyer et al. | |
| 6,423,082 B1 | 7/2002 | Houser et al. | |
| 6,773,444 B2 | 8/2004 | Messerly | |
| 6,783,524 B2 | 8/2004 | Anderson et al. | |
| 7,524,320 B2 | 4/2009 | Tierney et al. | |
| 7,691,098 B2 | 4/2010 | Wallace et al. | |
| 7,806,891 B2 | 10/2010 | Nowlin et al. | |
| 8,057,498 B2 | 11/2011 | Robertson | |
| 8,425,545 B2 | 4/2013 | Smith et al. | |
| 8,461,744 B2 | 6/2013 | Wiener et al. | |
| 8,479,969 B2 | 7/2013 | Shelton, IV | |
| 8,573,461 B2 | 11/2013 | Shelton, IV et al. | |
| 8,573,465 B2 | 11/2013 | Shelton, IV | |
| 8,591,536 B2 | 11/2013 | Robertson | |
| 8,602,288 B2 | 12/2013 | Shelton, IV et al. | |
| 8,616,431 B2 | 12/2013 | Timm et al. | |
| 8,623,027 B2 | 1/2014 | Price et al. | |
| 8,663,220 B2 | 3/2014 | Wiener et al. | |
| 8,783,541 B2 | 7/2014 | Shelton, IV et al. | |
| 8,800,838 B2 | 8/2014 | Shelton, IV | |
| 8,820,605 B2 | 9/2014 | Shelton, IV | |
| 8,844,789 B2 | 9/2014 | Shelton, IV et al. | |
| 9,095,346 B2 * | 8/2015 | Houser | A61B 18/1206 |
| 9,095,367 B2 | 8/2015 | Olsen et al. | |
| 9,301,759 B2 | 4/2016 | Spivey et al. | |
| 9,358,003 B2 * | 6/2016 | Hall | A61B 17/068 |
| 9,750,521 B2 | 9/2017 | Lamping et al. | |
| 9,949,785 B2 | 4/2018 | Price et al. | |
| 10,111,679 B2 * | 10/2018 | Baber | A61B 90/92 |
| 2017/0000541 A1 | 1/2017 | Yates et al. | |
| 2019/0216493 A1 * | 7/2019 | Worrell | A61B 17/320068 |

OTHER PUBLICATIONS

U.S. Appl. No. 15/644,944, filed Jul. 10, 2017.
International Search Report and Written Opinion dated Oct. 1, 2018 for Application No. PCT/US2018/043625, 16 pgs.

* cited by examiner

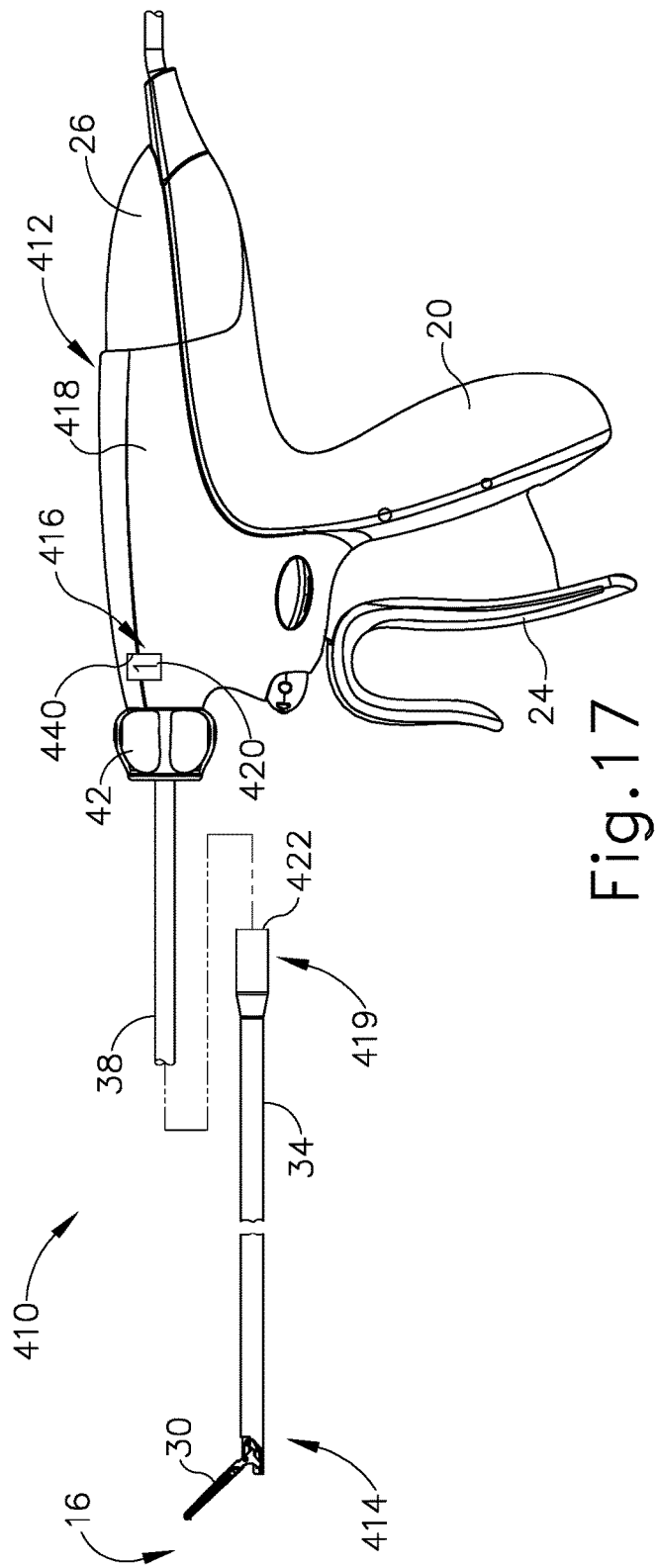
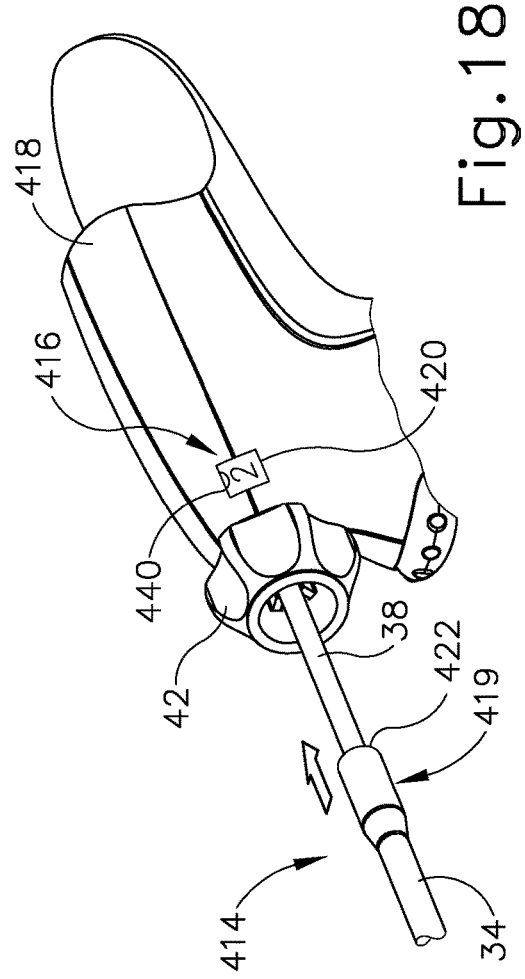
Fig.17
Fig.18

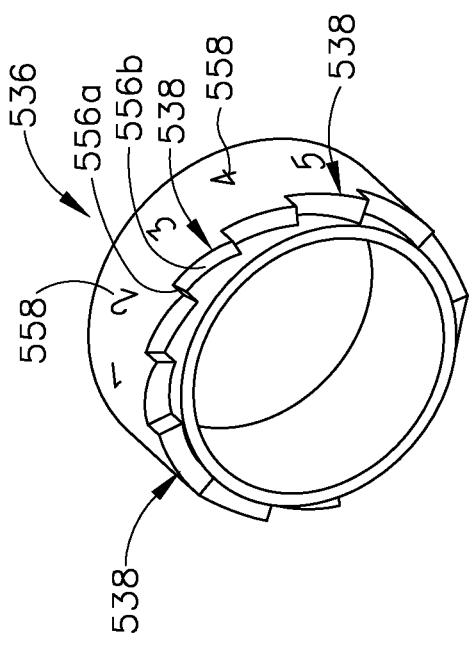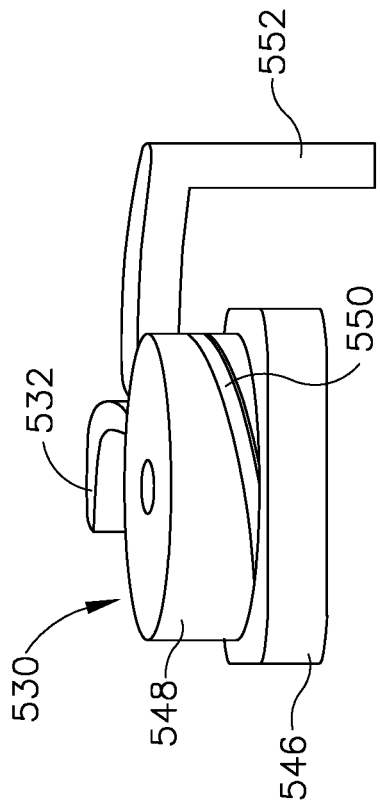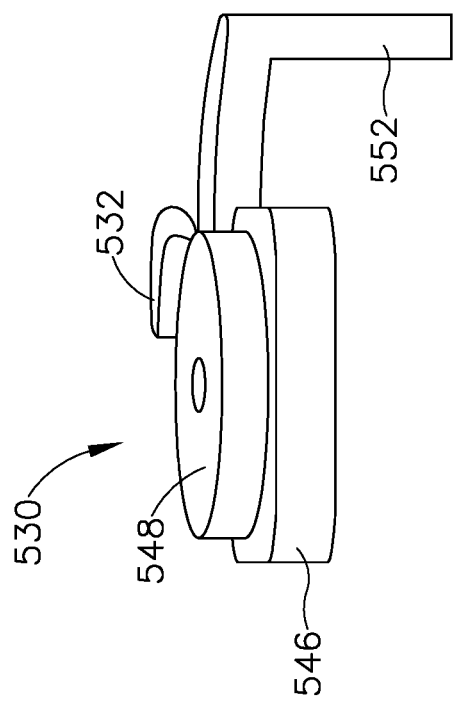

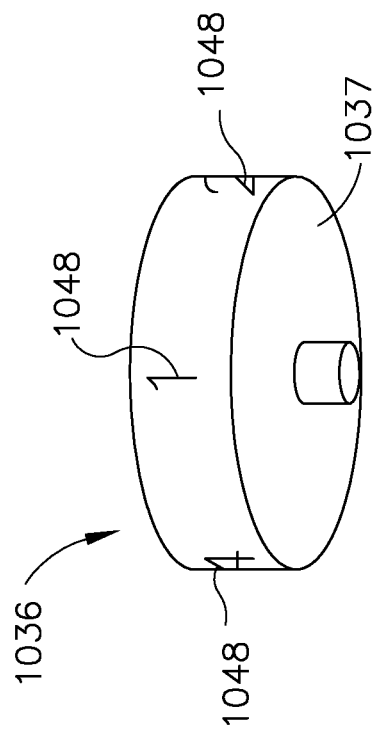
Fig.37
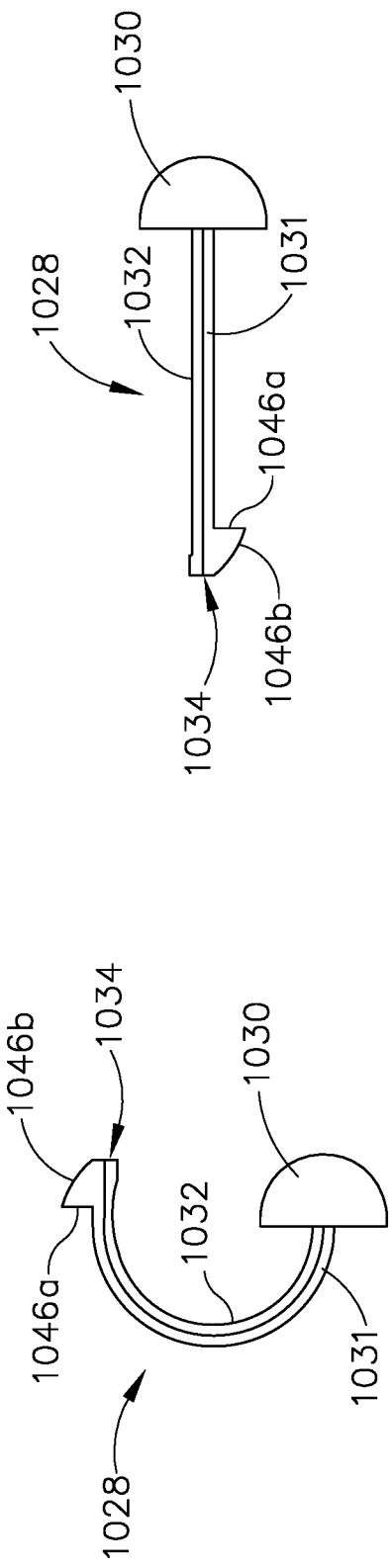
Fig.39
Fig.38

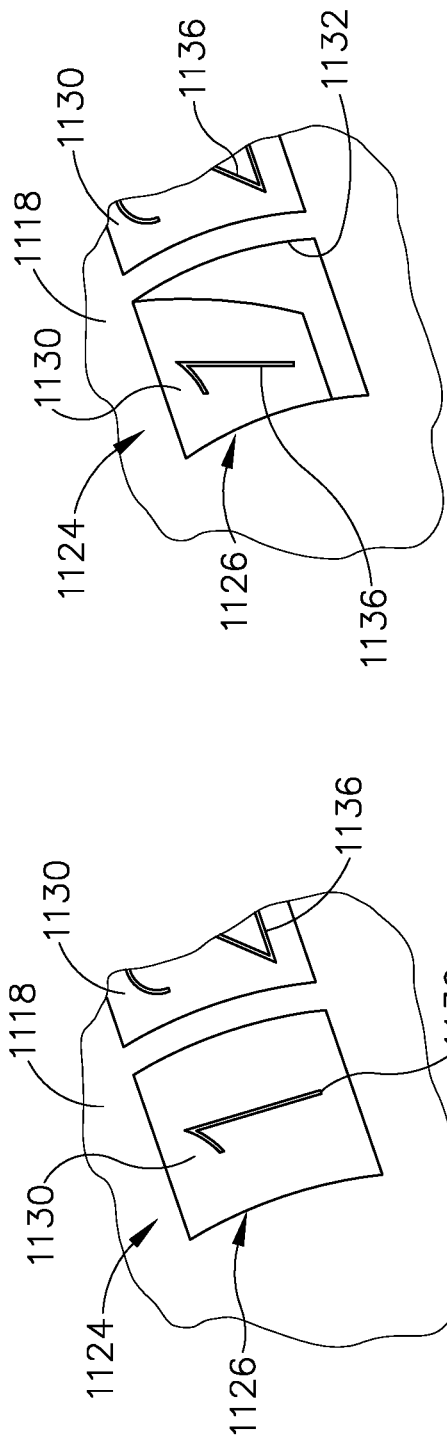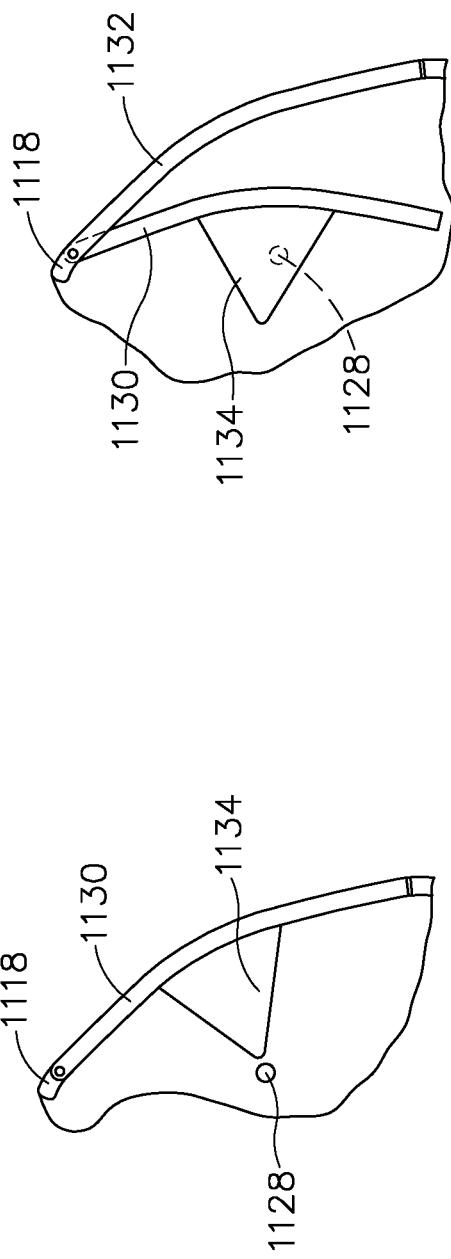
Fig. 44B
Fig. 45B
Fig. 44A
Fig. 45A

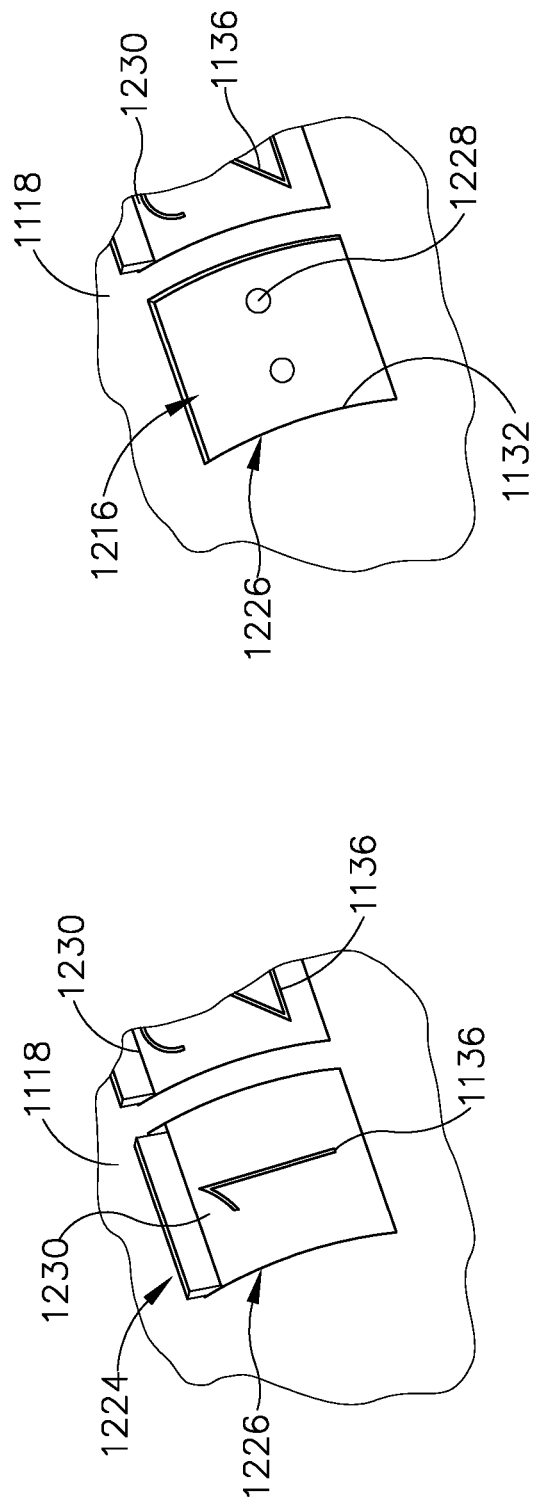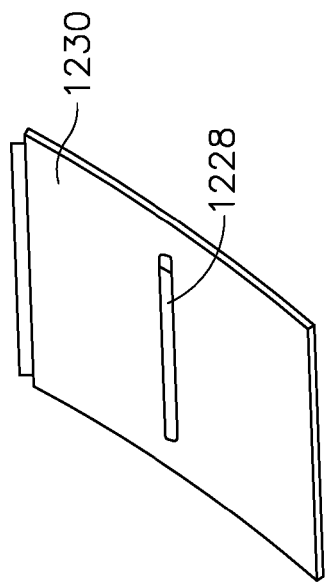
Fig.46B
Fig.47
Fig.46A

SURGICAL INSTRUMENT USE INDICATOR

BACKGROUND

Ultrasonic surgical instruments utilize ultrasonic energy for both precise cutting and controlled coagulation of tissue. The ultrasonic energy cuts and coagulates by vibrating a blade in contact with the tissue. Vibrating at frequencies of approximately 50 kilohertz (kHz), for example, the ultrasonic blade denatures protein in the tissue to form a sticky coagulum. Pressure exerted on the tissue with the blade surface collapses blood vessels and allows the coagulum to form a hemostatic seal. The precision of cutting and coagulation may be controlled by the surgeon's technique and adjusting the power level, blade edge, tissue traction, and blade pressure, for example.

Examples of ultrasonic surgical devices include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein; U.S. Pat. No. 6,283,981, entitled "Method of Balancing Asymmetric Ultrasonic Surgical Blades," issued Sep. 4, 2001, the disclosure of which is incorporated by reference herein; U.S. Pat. No. 6,309,400, entitled "Curved Ultrasonic Blade having a Trapezoidal Cross Section," issued Oct. 30, 2001, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,423,082, entitled "Ultrasonic Surgical Blade with Improved Cutting and Coagulation Features," issued Jul. 23, 2002, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,057,498, entitled "Ultrasonic Surgical Instrument Blades," issued Nov. 15, 2011, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; U.S. Pat. No. 8,623,027, entitled "Ergonomic Surgical Instruments," issued Jan. 7, 2014, the disclosure of which is incorporated by reference herein; U.S. Pat. No. 9,095,367, entitled "Flexible Harmonic Waveguides/Blades for Surgical Instruments," issued Aug. 4, 2015, the disclosure of which is incorporated by reference herein; and U.S. Pub. No. 2016/0022305, entitled "Ultrasonic Blade Overmold," published Jan. 28, 2016, issued as U.S. Pat. No. 9,750,521 on Sep. 5, 2017, the disclosure of which is incorporated by reference herein.

An ultrasonic surgical instrument generally includes an ultrasonic transducer and an ultrasonic blade configured to be driven by the ultrasonic transducer. Various ultrasonic surgical instruments enable the ultrasonic blade to be selectively attached and detached from the ultrasonic transducer, via a threaded coupling between the two components. It is desirable to apply an appropriate amount of torque to this threaded coupling when assembling the blade with the transducer. Applying too much torque can cause the threaded coupling to fracture and fail during use, and applying too little torque can cause the threaded coupling to loosen and inhibit effective transmission of ultrasonic energy to tissue during use. Either result is undesirable, and can render the surgical instrument ineffective or entirely inoperable. Ultrasonic blades and transducers of conventional ultrasonic surgical instruments may be assembled with a hand-held torque wrench tool that is provided separately from the surgical instrument. The torque wrench tool includes features that limit application of additional torque to the threaded coupling between the ultrasonic blade and transducer once a predetermined amount of torque has been reached. An example of such a torque wrench tool is disclosed in U.S. Pat. No. 5,059,210, entitled "Apparatus and Methods for Attaching and Detaching an Ultrasonic Actuated Blade/Coupler and an Acoustical Mount Therefor," issued Oct. 22, 1991, the disclosure of which is incorporated by reference herein.

While various types of ultrasonic surgical instruments and torque wrench mechanisms have been made and used, it is believed that no one prior to the inventor(s) has made or used the invention described herein.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 17 depicts a partially exploded side view of a fifth exemplary ultrasonic surgical instrument having a second wheel ratchet usage indicator for a shaft assembly and a handle assembly;

FIG. 18 depicts an enlarged perspective view of the ultrasonic surgical instrument of FIG. 17 with a portion of the shaft assembly being inserted into the handle assembly;

FIG. 22 depicts a perspective view of a ratchet wheel of the third wheel ratchet usage indicator of FIG. 20;

FIG. 23A depicts a perspective view of a ratchet mechanism of the third wheel ratchet usage indicator of FIG. 20 with the ratchet mechanism in a contracted state;

FIG. 23B depicts the perspective view of the ratchet mechanism similar to FIG. 23A, but showing the ratchet mechanism in an expanded state;

FIG. 37 depicts a perspective view of the cycle response usage indicator of FIG. 36;

FIG. 38 depicts a distal end view of a ratchet actuator of the cycle response usage indicator of FIG. 37 with the ratchet actuator in an unactuated state;

FIG. 39 depicts a distal end view of the ratchet actuator of FIG. 38 with the ratchet actuator in an actuated state;

FIG. 44A depicts an enlarged perspective view of the circuit board of FIG. 42 with a first numeral usage tab in a use remaining position indicating a first usage is in use;

FIG. 44B depicts the enlarged perspective view of the circuit board similar to FIG. 44A, but with the first use tab in a used position indicating the first usage is used;

FIG. 45A depicts a sectional view of the circuit board taken along a centerline of the first use tab in the use remaining position of FIG. 44A showing a closed-circuit portion;

FIG. 45B depicts a sectional view of the circuit board taken along a centerline of the first use tab in the used position of FIG. 44B showing an opened circuit portion;

FIG. 46A depicts an enlarged perspective view of a second circuit usage indicator having a circuit board with a first use tab in a use remaining position indicating a first usage is in use;

FIG. 46B depicts the enlarged perspective view of the circuit board similar to FIG. 46A, but with the first use tab removed thereby indicating the first usage is used;

FIG. 47 depicts a perspective view of the first numeral usage tab of FIG. 46A;

Figure 1:
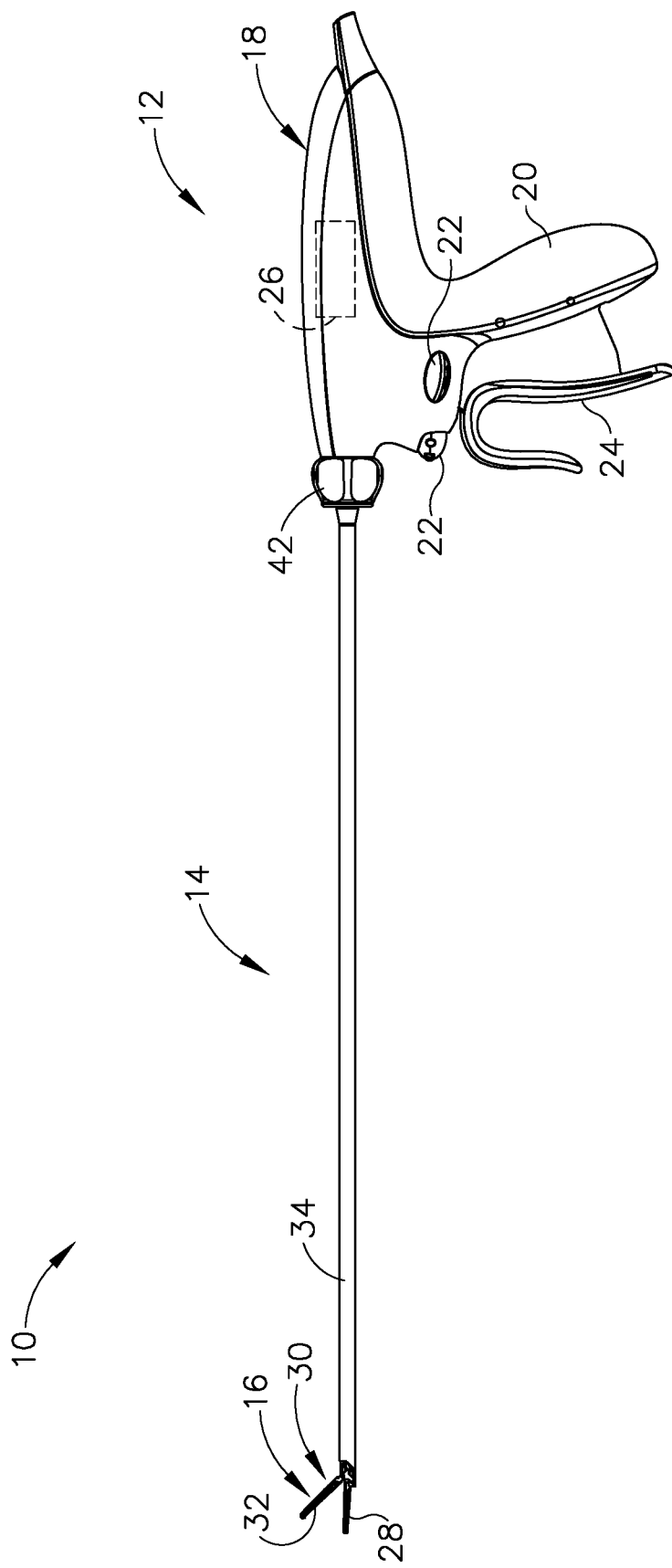
FIG. 1 depicts a side view of a first exemplary ultrasonic surgical instrument having a handle assembly and a shaft assembly with an end effector.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

I. Exemplary Surgical Instrument

Figure 2A:
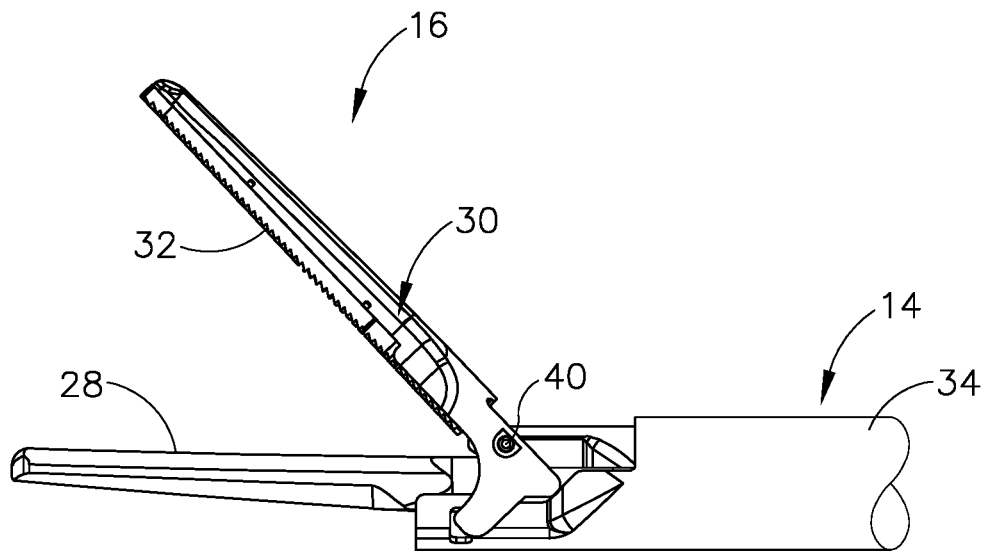
FIG. 2A depicts an enlarged side view of the end effector of FIG. 1 in an open configuration.
Figure 2B:
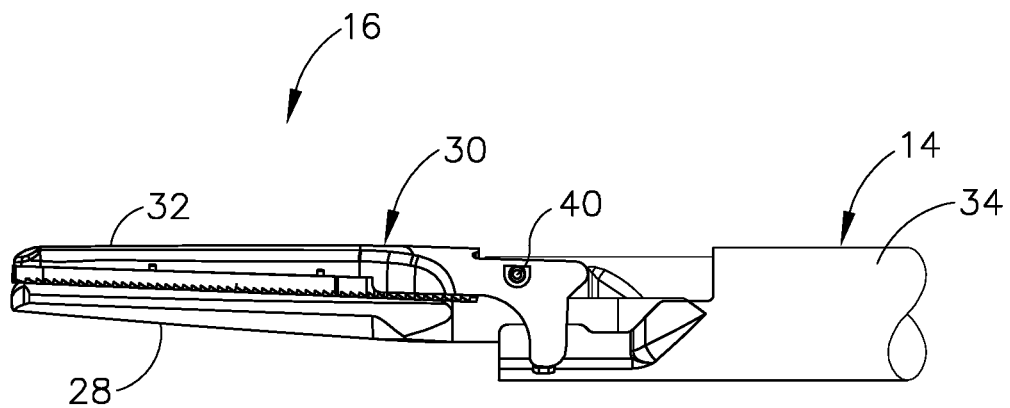
FIG. 2B depicts the enlarged side view of the end effector similar to FIG. 2A, but with the end effector in a closed configuration.

FIGS. 1-2B show an exemplary ultrasonic surgical instrument (10) that includes a handle assembly (12), a shaft assembly (14) extending distally from handle assembly (12), and an end effector (16) arranged at a distal end of shaft assembly (14). Handle assembly (12) comprises a body (18) including a pistol grip (20) and energy control buttons (22) configured to be manipulated by a surgeon to control various aspects of tissue treatment energy delivered by surgical instrument (10). A trigger (24) is coupled to a lower portion of body (18) and is pivotable toward and away from pistol grip (20) to selectively actuate end effector (16). In other suitable variations of surgical instrument (10), handle assembly (12) may comprise a scissor grip configuration, for example. Body (18) houses an ultrasonic transducer (20, shown schematically in FIG. 1, configured to deliver ultrasonic energy to end effector (16), as described in greater detail below. Body (18) may also be referred to herein as a housing (18) and may include one component or an assembly of components. The terms "body" and "housing" are thus not intended to unnecessarily limit the invention described herein to any number of discrete components.

As shown best in FIGS. 2A-2B, end effector (16) includes an ultrasonic blade (28) and a clamp arm (30) configured to selectively pivot toward and away from ultrasonic blade (28) for clamping tissue therebetween. Clamp arm (30) includes a clamp pad (32) arranged on a clamping side thereof and is moveable from an open position shown in FIG. 2A to a closed position shown in FIG. 2B. With respect to FIG. 3, ultrasonic blade (28) is acoustically coupled with ultrasonic transducer (26), which is configured to drive (i.e., vibrate) ultrasonic blade (28) at ultrasonic frequencies for cutting and/or sealing tissue positioned in contact with ultrasonic blade (28). Clamp arm (30) is operatively coupled with trigger (24) such that clamp arm (30) is configured to pivot toward ultrasonic blade (28), to the closed position, in response to pivoting of trigger (24) toward pistol grip (20). Further, clamp arm (30) is configured to pivot away from ultrasonic blade (28), to the open position in response to pivoting of trigger (24) away from pistol grip (20). Various suitable ways in which clamp arm (30) may be coupled with trigger (24) will be apparent to those of ordinary skill in the art in view of the teachings provided herein. In some versions, one or more resilient members may be incorporated to bias clamp arm (30) and/or trigger (24) toward the open position.

Shaft assembly (14) of the present example extends along a longitudinal axis and includes an outer tube (34), an inner tube (36) received within outer tube (34), and an ultrasonic waveguide (38) supported within and extending longitudinally through inner tube (36). Ultrasonic blade (28) is formed integrally with and extends distally from waveguide (38). A proximal end of clamp arm (30) is pivotally coupled to distal ends of outer and inner tubes (34, 36), enabling clamp arm (30) to pivot relative to shaft assembly (14) about a pivot axis defined by a pivot pin (40) (see FIG. 2A) extending transversely through the distal end of inner tube (36).

In the present example, inner tube (36) is longitudinally fixed relative to handle assembly (18), and outer tube (34) is configured to translate relative to inner tube (36) and handle assembly (18), along the longitudinal axis of shaft assembly (20). As outer tube (34) translates distally, clamp arm (30) pivots about its pivot axis toward its open position. As outer tube (34) translates proximally, clamp arm (30) pivots about its pivot axis in an opposite direction toward its closed position. Though not shown, a proximal end of outer tube (34) is operatively coupled with trigger (24) such that actuation of trigger (24) causes translation of outer tube (34) relative to inner tube (36), thereby opening or closing clamp arm (30) as discussed above. In other suitable configurations not shown herein, outer tube (34) may be longitudinally fixed and inner tube (36) may be configured to translate for moving clamp arm (30) between the open and closed positions. Various other suitable mechanisms for actuating clamp arm (30) between the open and closed positions will be apparent to those of ordinary skill in the art.

Figure 3:
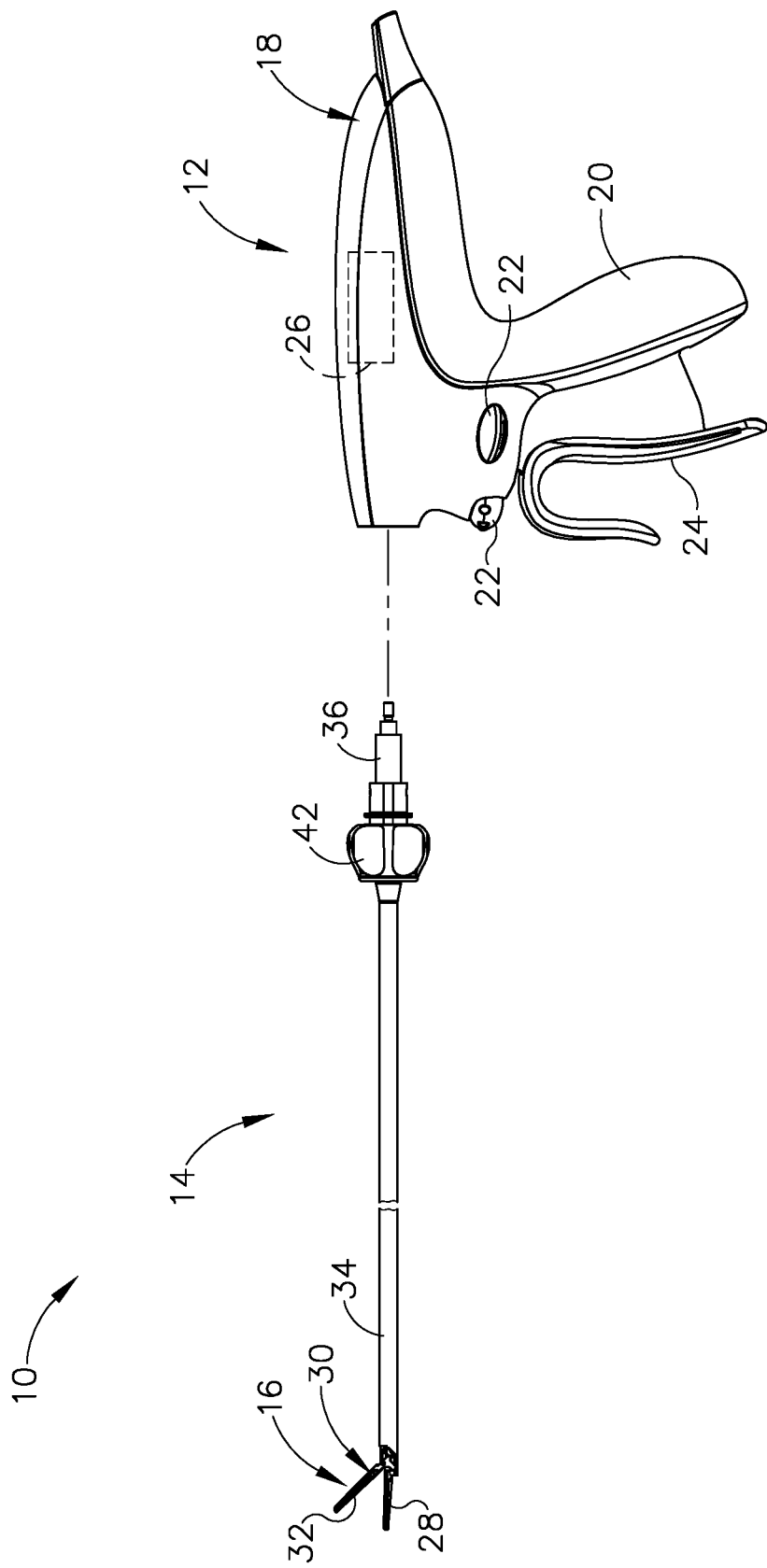
FIG. 3 depicts a partially exploded side view of the ultrasonic surgical instrument of FIG. 1.
Figure 4:
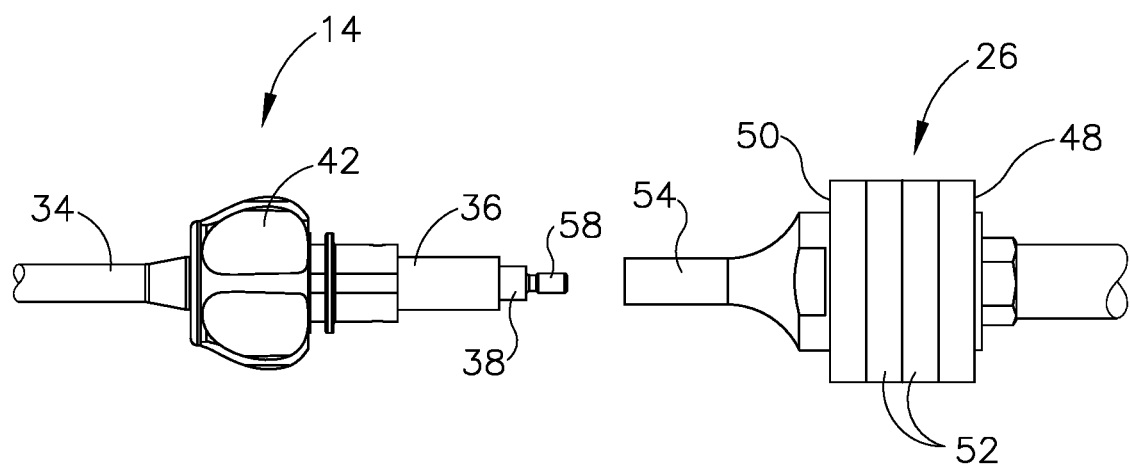
FIG. 4 depicts a partially schematic enlarged side view of an ultrasonic transducer, a waveguide, and a rotation knob of the ultrasonic surgical instrument of FIG. 1, showing attachment of the waveguide to the ultrasonic transducer.

Shaft assembly (14) and end effector (16) are configured to rotate together relative to body (18) about the longitudinal axis defined by shaft assembly (14). As shown in FIGS. 3-4, shaft assembly (14) further includes a rotation knob (42) arranged at a proximal end thereof. Rotation knob (42) is rotatably coupled to body (18) of handle assembly (12), and is rotationally fixed to outer tube (34), inner tube (36), and waveguide (38) by a coupling pin (not shown) extending transversely therethrough. Coupling pin (not shown) is arranged at a longitudinal location corresponding to an acoustic node of waveguide (38). In other examples, rotation knob (42) may be rotationally fixed to the remaining components of shaft assembly (14) in various other manners. Rotation knob (42) is configured to be gripped by a user to selectively manipulate the rotational orientation of shaft assembly (14) and end effector (16) relative to handle assembly (12). Various examples of acoustic and mechanical connections between shaft assembly (14) and handle assembly (14) are described in greater detail in U.S. patent application Ser. No. 15/644,930, entitled "Acoustic Drivetrain with External Collar at Nodal Position," filed on Jul. 10, 2017, published as U.S. Pub. No. 2019/0008546 on Jan. 10, 2019, and U.S. patent application Ser. No. 15/644,944, entitled "Features to Couple Acoustic Drivetrain Components in Ultrasonic Surgical Instrument," filed on Jul. 10, 2017, published as U.S. Pub. No. 2019/0008547 on Jan. 10, 2019, the disclosures of which are each incorporated by reference herein.

Figure 5:
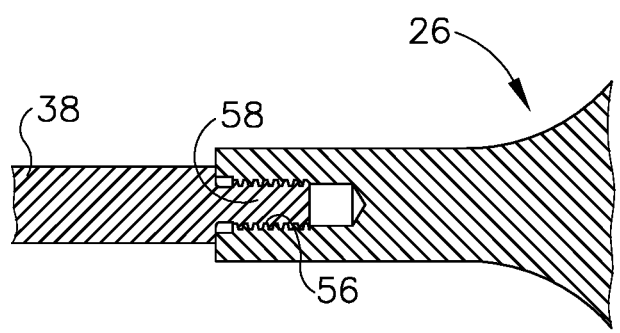
FIG. 5 depicts a partially schematic enlarged side view of a threaded coupling between the ultrasonic transducer and the waveguide of FIG. 4.
Figure 6:
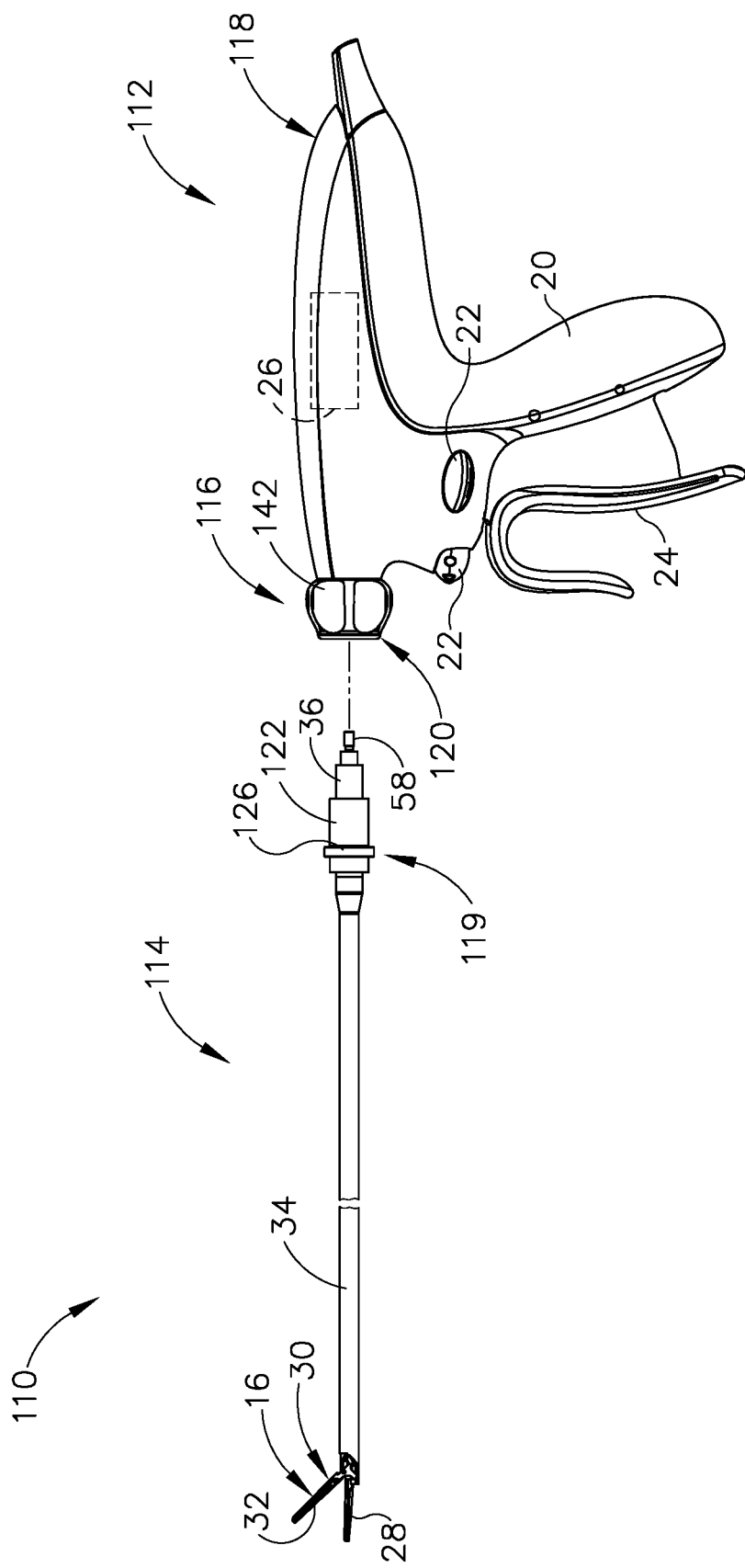
FIG. 6 depicts a partially exploded side view of a second exemplary ultrasonic surgical instrument having a first additive usage indicator for a shaft assembly and a handle assembly.

FIGS. 3-5 show additional details of ultrasonic transducer (26) and waveguide (38). In particular, ultrasonic transducer (26) and waveguide (38) are configured to threadedly couple together. Accordingly, waveguide (38) is configured to acoustically couple ultrasonic transducer (26) with ultrasonic blade (28), and thereby communicate ultrasonic mechanical vibrations from ultrasonic transducer (26) to blade (28). In this manner, ultrasonic transducer (26), waveguide (38), and ultrasonic blade (28) together define an acoustic assembly of ultrasonic surgical instrument (10). Ultrasonic transducer (26) is rotatably supported within body (18) of handle assembly (12), and is configured to rotate with shaft assembly (14), including waveguide (38), and end effector (16) about the longitudinal axis of shaft assembly (14).

Ultrasonic transducer (26) is electrically coupled with a generator (not shown), which may be provided externally of ultrasonic surgical instrument (10) or integrated within surgical instrument (10). During use, generator (not shown) powers ultrasonic transducer (26) to produce ultrasonic mechanical vibrations, which are communicated distally through waveguide (38) to ultrasonic blade (28). Ultrasonic blade (28) is caused to oscillate longitudinally in the range of approximately 10 to 500 microns peak-to-peak, for example, and in some instances in the range of approximately 20 to 200 microns, at a predetermined vibratory frequency $f_o$ of approximately 50 kHz, for example. Vibrating ultrasonic blade (28) may be positioned in direct contact with tissue, with or without assistive clamping force provided by clamp arm (30), to impart ultrasonic vibrational energy to the tissue and thereby cut and/or seal the tissue. For example, blade (28) may cut through tissue clamped between clamp arm (30) and a clamping side of blade (28), or blade (28) may cut through tissue positioned in contact with an oppositely disposed non-clamping side of blade (28) having an edge, for example during a "back-cutting" movement. In some versions, waveguide (38) may be configured to amplify the ultrasonic vibrations delivered to blade (28). Waveguide (38) may include various features operable to control the gain of the vibrations, and/or features suitable to tune waveguide (38) to a selected resonant frequency.

In the present example, ultrasonic transducer (26) includes a first resonator (or "end-bell") (48), a conically shaped second resonator (or "fore-bell") (50), and a transduction portion arranged between end-bell (48) and fore-bell (50) that includes a plurality of piezoelectric elements (52). A compression bolt (not shown) extends distally, coaxially through end-bell (48) and piezoelectric elements (52), and is threadedly received within a proximal end of fore-bell (50). A velocity transformer (or "horn") (54) extends distally from fore-bell (146) and includes an internally threaded bore (56) configured to receive and threadedly couple with an externally threaded proximal tip (58) of waveguide (38) as shown in FIGS. 4-5.

While the teachings herein are disclosed in connection with ultrasonic surgical instruments, it will be appreciated that they may also be employed in connection with surgical instruments configured to provide a combination of ultrasonic and radio frequency (RF) energies. Examples of such instruments and related methods and concepts are disclosed in U.S. Pat. No. 8,663,220, entitled "Ultrasonic Surgical Instruments," issued Mar. 4, 2014, the disclosure of which is incorporated by reference herein; U.S. Pub. No. 2015/0141981, entitled "Ultrasonic Surgical Instrument with Electrosurgical Feature," published May 21, 2015, issued in U.S. Pat. No. 9,949,785 on Apr. 24, 2018, the disclosure of which is incorporated by reference herein; and U.S. Pub. No. 2017/0000541, entitled "Surgical Instrument with User Adaptable Techniques," published Jan. 5, 2017, the disclosure of which is incorporated by reference herein.

II. Various Integrated Usage Indicators

Given that various portions of ultrasonic surgical instrument (10) removably connect together, it may be desirable in various examples to reuse some portions of ultrasonic surgical instrument (10) while replacing others upon reconnection for further use by the surgeon. For example, handle assembly (12) in the present example is reusable whereas shaft assembly (14) may be disconnected and replaced with an unused, replacement shaft assembly (14). Despite the reusability of handle assembly (12), one or more components of handle assembly (12) may be replaced after a predetermined number of use cycles of use for each respective patient treatment. For example, ultrasonic transducer (26) may operate efficiently and effectively up to five use cycles, but performance may deteriorate beyond the five use cycles such that replacement of handle assembly (12) is desirable.

While such reuse of handle assembly (12) followed by replacement of handle assembly (12) may be desirable, inhibiting reuse beyond the predetermined number of use cycles may be complicated, difficult, or tedious given that inspection of handle assembly (12) may not readily communicate the predetermined complete usage of handle assembly (12). An integrated usage indicator (116, 216, 316, 416, 516, 716, 816, 916, 1016, 1116, 1216, 1316, 1416) with a used state indicator as described below may thus be desirable in some instance for indicating usage to a clinician, such as the surgeon, without the need for manually tracking such usage separate from handle assembly (12). Once used state indicator indicates such use in a used state to the clinician, a replacement handle assembly (12) may be used for a following patient treatment. While various examples are given below regarding a particular number of uses and/or reuses, it will be appreciated that any number of uses and/or reuses may be possible in other examples. The invention is thus not intended to be unnecessarily limited to a particular number of uses and/or reuses.

The following description provides various examples of integrated usage indicators (116, 216, 316, 416, 516, 716, 816, 916, 1016, 1116, 1216, 1316, 1416). Such integrated usage indicators (116, 216, 316, 416, 516, 716, 816, 916, 1016, 1116, 1216, 1316, 1416) described below may be used with any ultrasonic surgical instrument described above and below and in any of the various procedures described in the various patent references cited herein. To this end, like numbers below indicated like features described above. Other suitable ways in which various ultrasonic surgical instruments may be used will be apparent to those of ordinary skill in the art in view of the teachings herein.

A. First Additive Usage Indicator

FIGS. 6-8B illustrate a second exemplary ultrasonic surgical instrument (110) having a handle assembly (112) configured to be operated up to a predetermined number of use cycles, a shaft assembly (114) configured for a single use cycle of treatment, and a first additive usage indicator (116). With respect to FIGS. 6-7A, first additive usage indicator (116) is integrated into portions of shaft assembly (114) and a housing (118) of handle assembly (112) for recording and indicating each respective use cycle of handle assembly (112) in a use remaining state to a used state. First additive usage indicator (116) has a shaft portion (119) that cooperates with a housing portion (120) upon connection of shaft assembly (114) to handle assembly (112) to thereby direct first additive usage indicator (116) toward the used state with each replacement shaft assembly (114). Once shaft assembly (114) has been replaced the predetermined number of use cycles, first additive usage indicator (116) indicates the used state of handle assembly (112) to the clinician. Such indication of first additive usage indicator (116) is visual as well as a lockout, which inhibits operation of handle assembly (112).

Figure 7A:
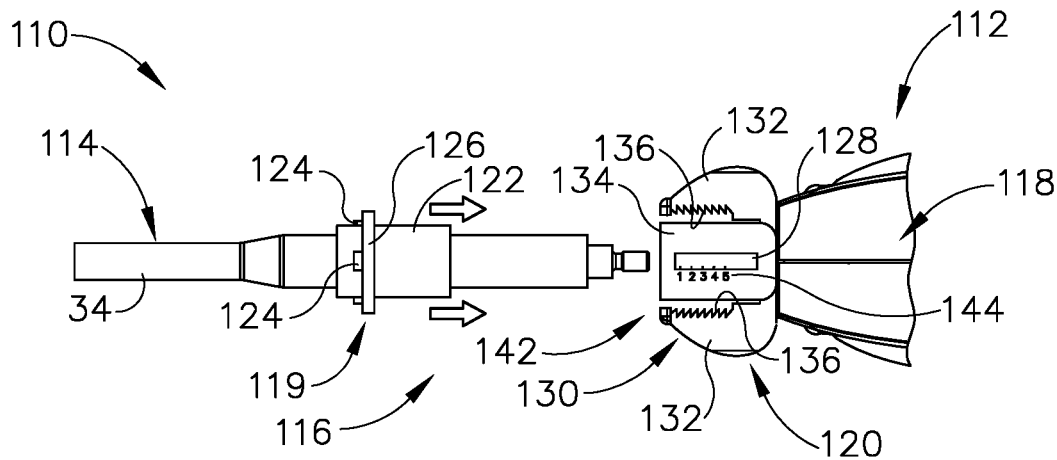
FIG. 7A depicts an enlarged top view of the ultrasonic surgical instrument and the first additive usage indicator of FIG. 6 with the shaft assembly being inserted into the handle assembly.

As shown in FIG. 7A, shaft portion (119) of first additive usage indicator (116) includes an annular collar body (122) position on a proximal end portion of shaft assembly (114) about outer tube (34). A plurality of stop members (124) are angularly positioned about the annular collar (122) and extend radially outward therefrom. In addition, a counter ring member (126) is translatably positioned on annular collar body (122) against a proximal surface of stop members (124). Thereby, stop members (124) inhibit distal movement of counter ring member (126) relative to annular collar body (122), but allow proximal movement of counter ring member (126) relative to annular collar body (122) until detached therefrom.

Figure 7B:
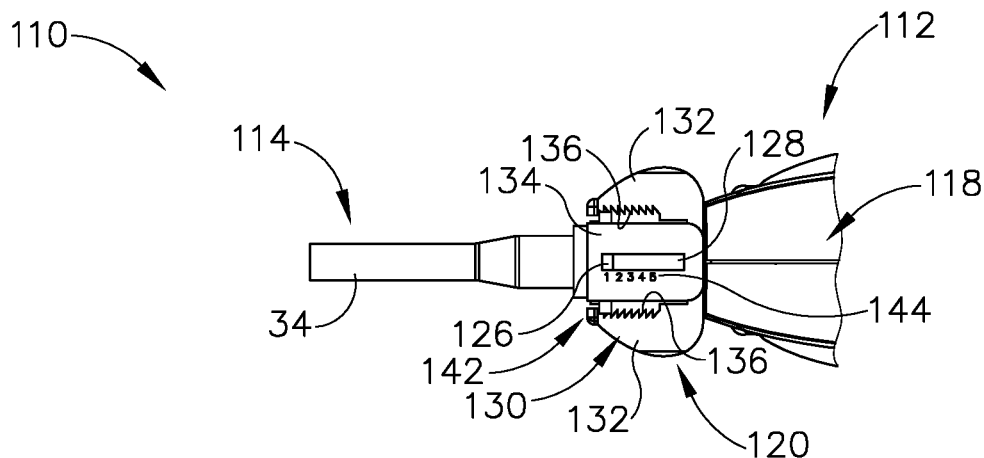
FIG. 7B depicts the enlarged top view of the ultrasonic surgical instrument and the first additive usage indicator similar to FIG. 7A, but showing the shaft assembly inserted into the handle assembly.
Figure 7C:
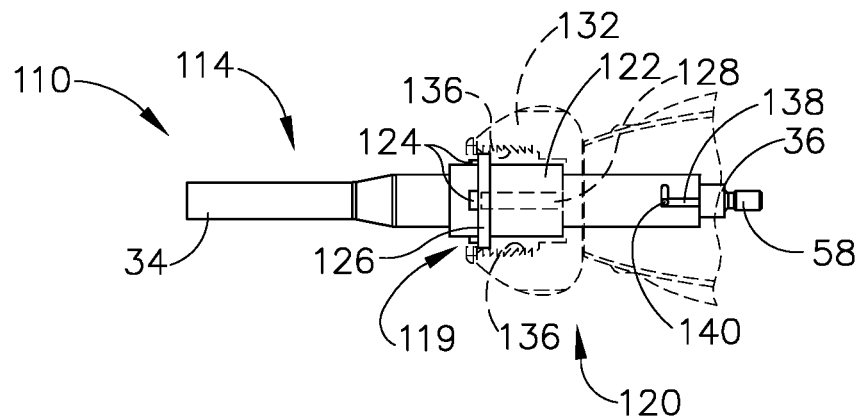
FIG. 7C depicts the enlarged top view of the ultrasonic surgical instrument and the first additive usage indicator similar to FIG. 7B, but having various features hidden for more clearly showing a shaft coupling in an unlocked state between the shaft assembly and the handle assembly.
Figure 7D:
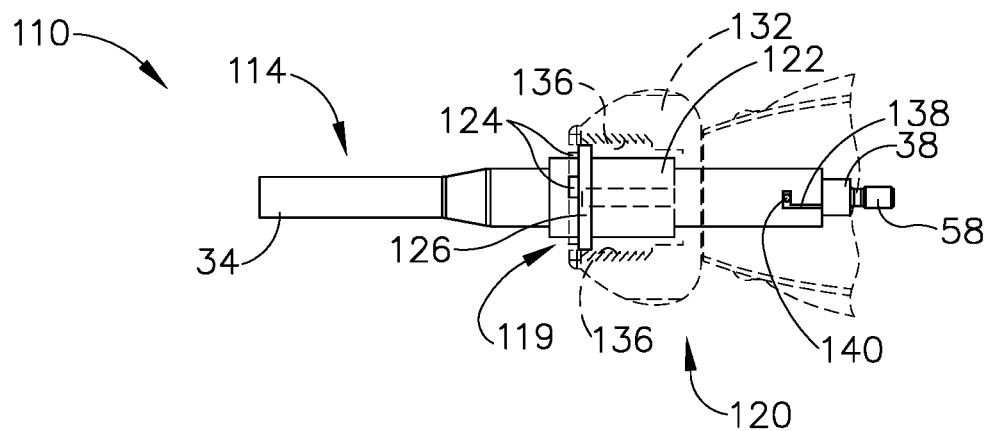
FIG. 7D depicts the enlarged top view of the ultrasonic surgical instrument and the first additive usage indicator similar to FIG. 7C, but showing the shaft coupling in a locked state and the shaft assembly attached to the handle assembly with the first additive usage indicator indicating a first use of the handle assembly.

Housing portion (120) of first additive usage indicator (116) includes a capture knob (142) having a longitudinally extending indicia window (128) and a catch (130) having a pair of laterally positioned and longitudinally cantilevered catch arms (132) about a catch post (134). Capture knob (142) operates similar to knob (42) (see FIG. 2) once receiving outer tube (34) for treatment, but is a portion of housing (118) rather than shaft assembly (114). As the proximal portion of shaft assembly (114) is inserted into handle assembly (112) for mechanical and acoustic connection therewith, catch post (134) axially receives counter ring member (126) thereon. In addition, catch arms (132) bias radially outward to receive counter ring member (126) between and capture counter ring member (126) on catch post (134) as shown in FIG. 7B. Each capture arm (132) of the present example further includes a plurality of inner ratchet teeth (136) configured to inhibit distal movement of counter ring member (126) relative to capture knob (142), but allow proximal movement of counter ring member (126) relative to capture knob (142). In this respect, proximal movement of stop members (124) urge counter ring member (126) onto catch post (134) for capture by catch arms (132) until bayonet slot (138) receives bayonet pin (140) for mechanically coupling shaft assembly (114) to handle assembly (112) as shown in FIGS. 7C-7D.

Figure 7E:
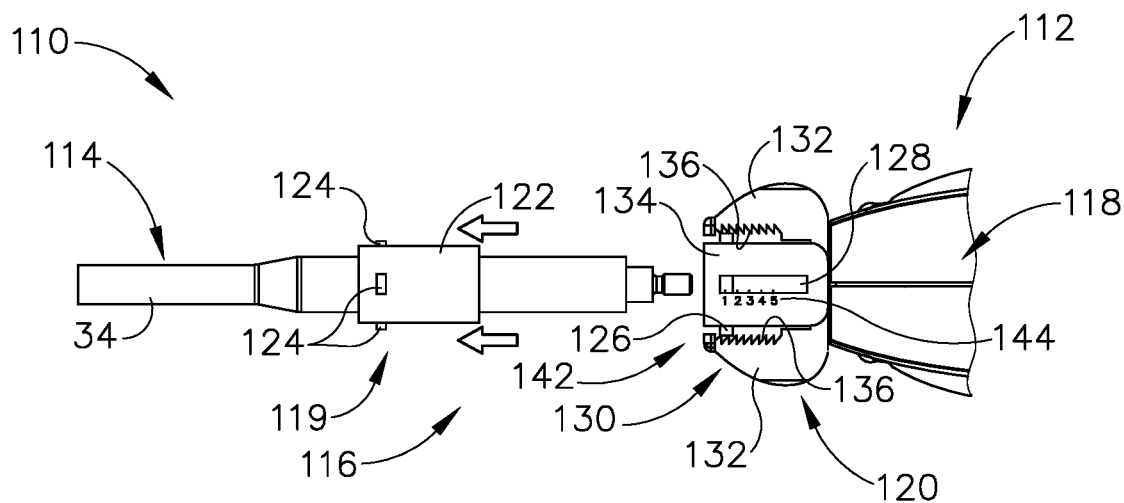
FIG. 7E depicts the enlarged top view of the ultrasonic surgical instrument and the first additive usage indicator similar to FIG. 7D, but showing the shaft assembly removed from the handle assembly after use and the first additive usage indicator indicating the first use of the handle assembly.
Figure 7F:
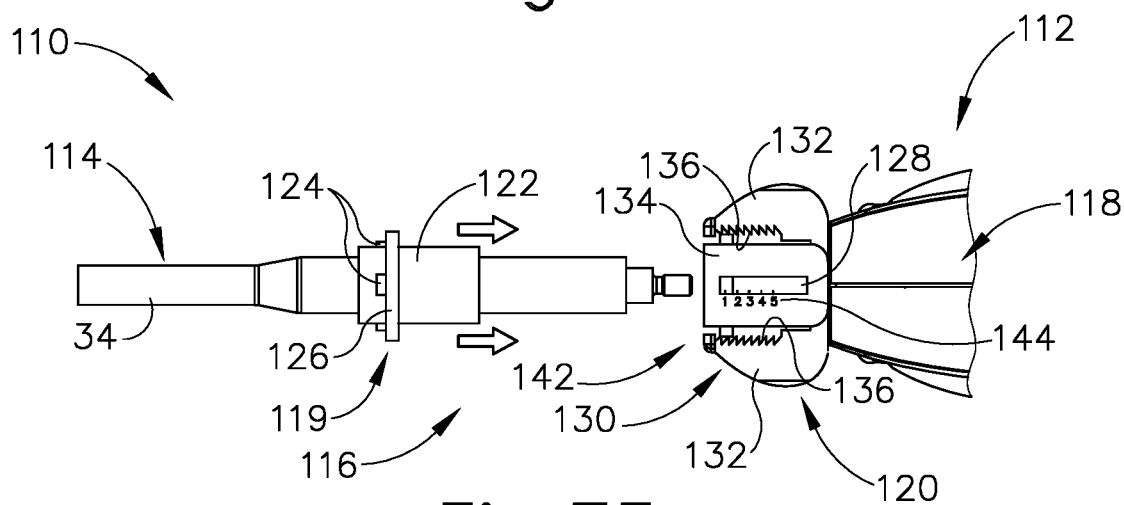
FIG. 7F depicts the enlarged top view of the ultrasonic surgical instrument and the first additive usage indicator similar to FIG. 7E, but showing another, replacement shaft assembly being inserted into the handle assembly.
Figure 7G:
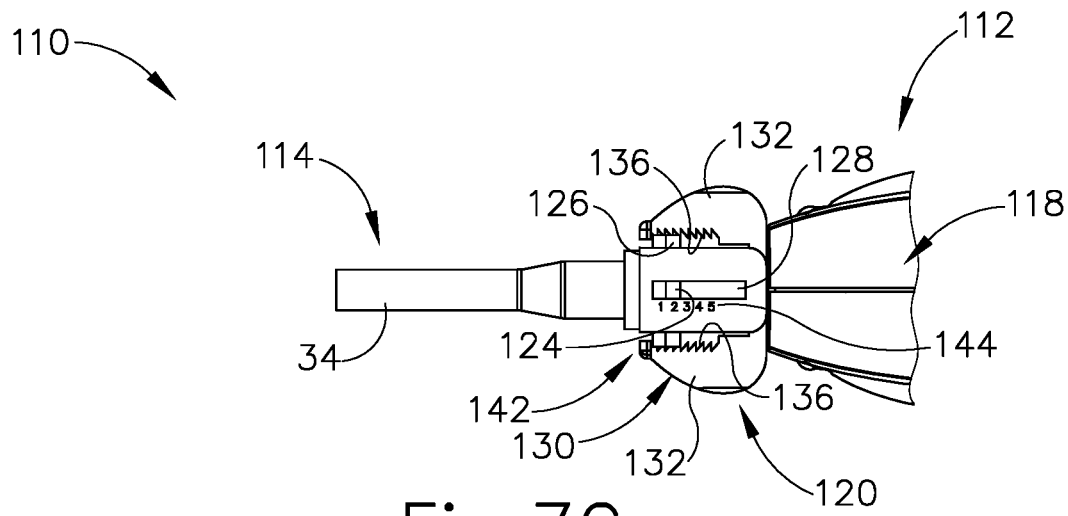
FIG. 7G depicts the enlarged top view of the ultrasonic surgical instrument and the first additive usage indicator similar to FIG. 7F, but showing the shaft assembly inserted into the handle assembly and the first additive usage indicator indicating a second use of the handle assembly.

As briefly discussed above, capture knob (142) includes indicia window (128) through catch post (134) for clinician to visually identify the presence of any counter ring members (126) received on catch post (134). In addition, catch post (132) further includes a series of counter indices (144), which are longitudinally and linearly positioned on capture knob (142) increasing in the proximal direction. The present example of counter indices (144) includes proximally increasing numbers "1," "2," "3," "4," and "5" and are respectively configured to correspond to each replacement shaft assembly (114) used with handle assembly (112) in relation to counter ring members (126). For example, as shown in FIGS. 7D-7E, a first counter ring member (126) longitudinally aligns with counter indicia (144) "1" to indicate to the clinician through indicia window (128) that handle assembly (112) is in its first use.

Given that catch arms (132) are configured to capture counter ring member (126), removal of shaft assembly (114) from handle assembly (112) causes capture ring member (126) to remain with capture knob (142). With respect to FIGS. 7F-7G, additional replacement shaft assemblies (114) with respective counter ring members (126) used with handle assembly (112) simply urge each captured counter ring member (126) proximally to align with the successive counter indicia (144). Thus, even after removal of one or more shaft assemblies (114) from handle assembly (112), the number of use cycles based shaft assembly connections (114) is recorded with handle assembly (112) throughout the remaining use state. In one example, counter ring members (126) may in addition or alternatively include a radio-frequency identification (RFID) tag for recording uses.

Figure 8A:
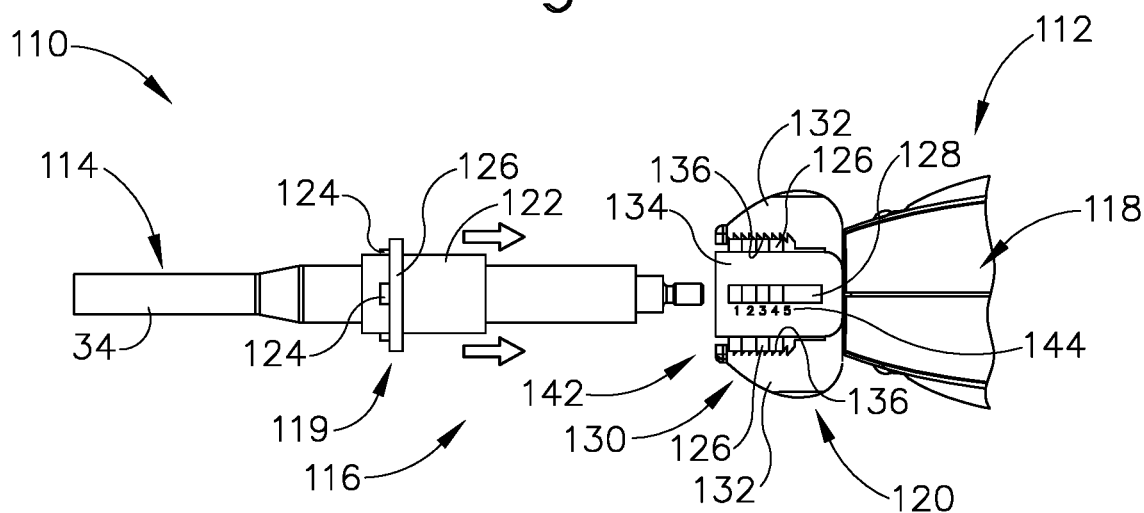
FIG. 8A depicts an enlarged top view of the ultrasonic surgical instrument and the first additive usage indicator of FIG. 6 indicating a complete usage of the handle assembly and the shaft assembly being inserted toward the handle assembly.
Figure 8B:
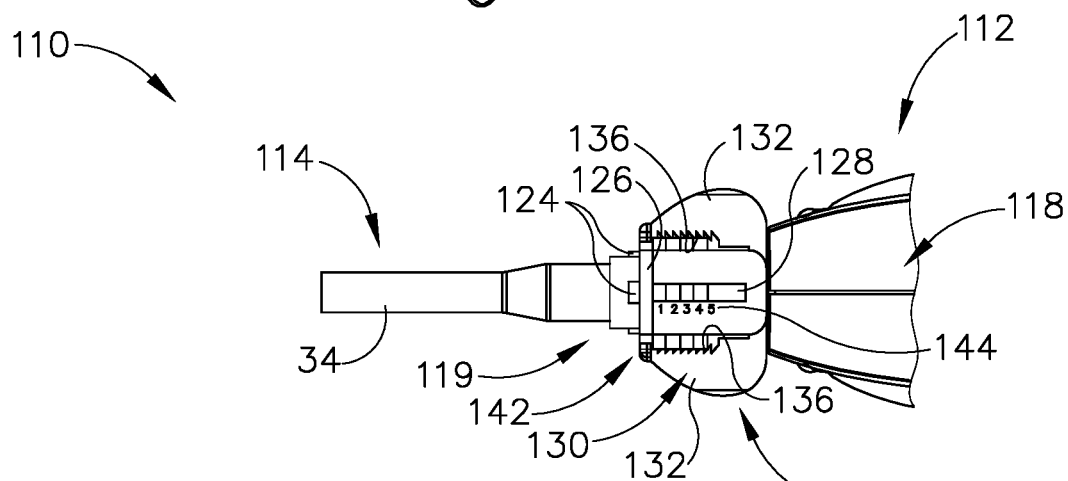
FIG. 8B depicts the enlarged top view of the ultrasonic surgical instrument and the first additive usage indicator similar to FIG. 8B, but showing the first additive usage indicator inhibiting attachment of the shaft assembly to the handle assembly following the complete usage of the handle assembly.
Figure 9:
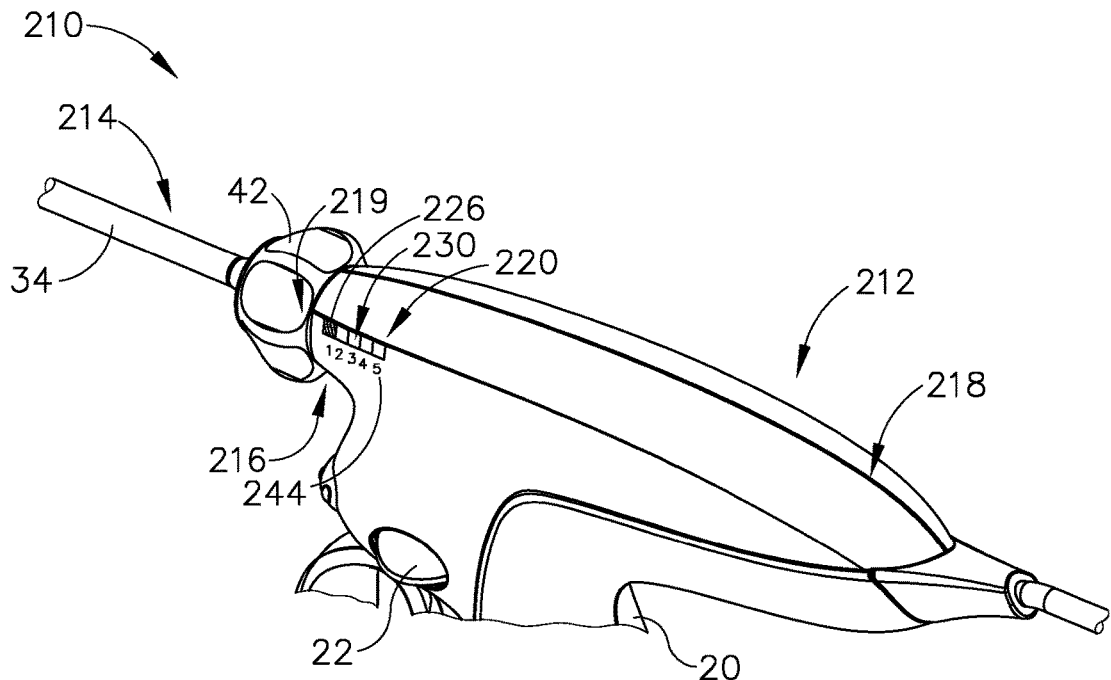
FIG. 9 depicts an enlarged perspective view of a third exemplary ultrasonic surgical instrument having a second additive usage indicator for a shaft assembly and a handle assembly.

Once catch (130) is full of counter ring members (126), first additive usage indicator is visually in the used state as shown in FIGS. 8A-8B. In addition, catch (130) is configured to receive no more counter ring members (126) than those that correspond to the predetermined number of use cycles based on replacement shaft assemblies (114). An additional counter ring member (126) greater than the predetermined number of use cycles, which in the present example is five, is configured to block acoustic and mechanical connection of another replacement shaft assembly (114) to handle assembly. First additive usage indicator (116) is thereby configured to inhibit inadvertently using handle assembly (112) beyond the predetermined number of use cycles.

In use, with respect to FIGS. 7A-7G, the clinician connects the first replacement shaft assembly (114) to handle assembly (112) such that counter ring member (126) is captured by catch (130) in alignment with the first indicia (144) for indicating the first use to clinician. Following treatment of the patient, shaft assembly (114) is disconnected from handle assembly (112) thereby detaching counter ring member (126) from shaft assembly (114). Handle assembly (112) is then prepped, such as by heating and/or sterilizing, for another surgical procedure and another replacement shaft assembly (114) is connected to handle assembly (112). The second counter ring member (126) urges the first counter ring member (126) in alignment with the second indicia for indicating the second use to the clinician. Such reuse continues as shown in FIGS. 7A-7G in the remaining use state until catch (130) is full of counter ring members (126) in the used state as shown in FIGS. 8A-8G.

B. Second Additive Usage Indicator

FIGS. 9-12E illustrate a third exemplary ultrasonic surgical instrument (210) having a handle assembly (212) configured to be operated up to a predetermined number of use cycles, a shaft assembly (214) configured for a single use cycle of treatment, and a second additive usage indicator (216). With respect to FIGS. 9-10, second additive usage indicator (216) is integrated into portions of shaft assembly (214) and a housing (218) of handle assembly (212) for recording and indicating each respective use cycle of handle assembly (212) in a use remaining state to a used state. Second additive usage indicator (216) has a shaft portion (219) that cooperates with a housing portion (220) upon connection of shaft assembly (214) to handle assembly (212) to thereby direct second additive usage indicator (216) toward the used state with each replacement shaft assembly (214). Once shaft assembly (214) has been replaced the predetermined number of use cycles, second additive usage indicator (216) indicates the used state of handle assembly (212) to the clinician. Such indication of second additive usage indicator (216) is visual as well as a lockout, which inhibits operation of handle assembly (212).

Figure 10:
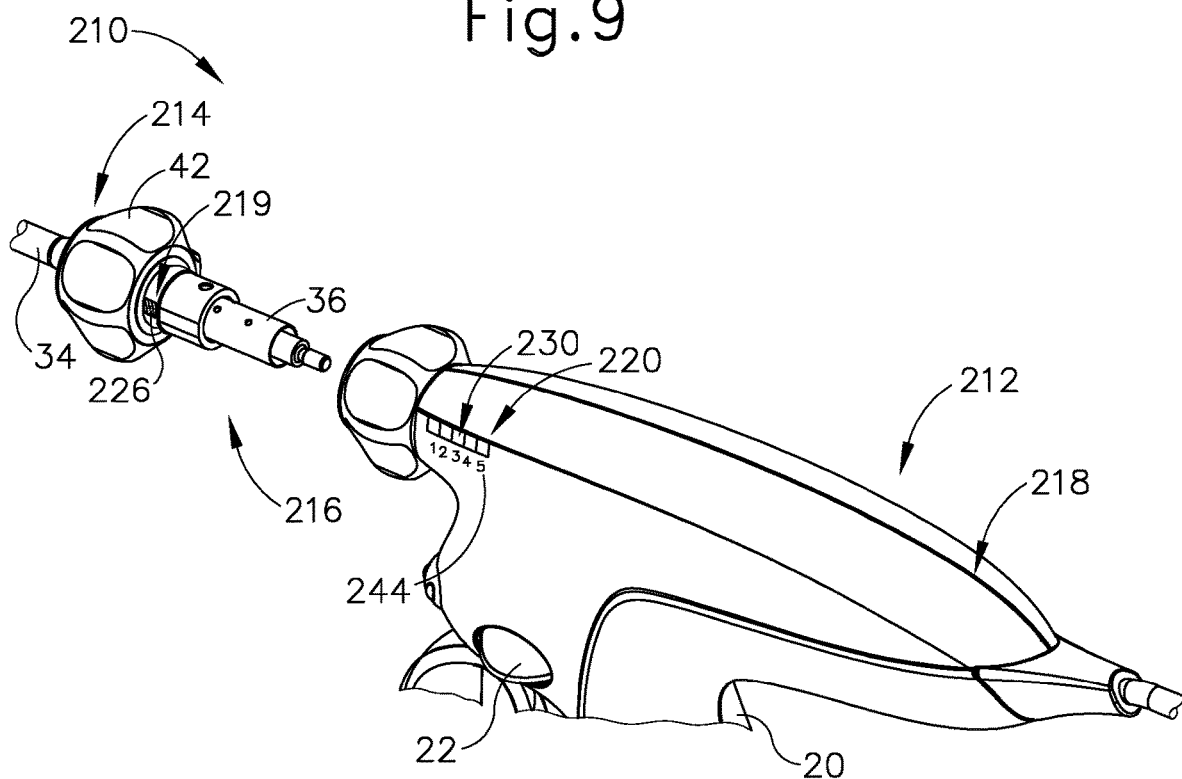
FIG. 10 depicts an enlarged, partially exploded perspective view of the ultrasonic surgical instrument with the second additive usage indicator of FIG. 9.
Figure 11:
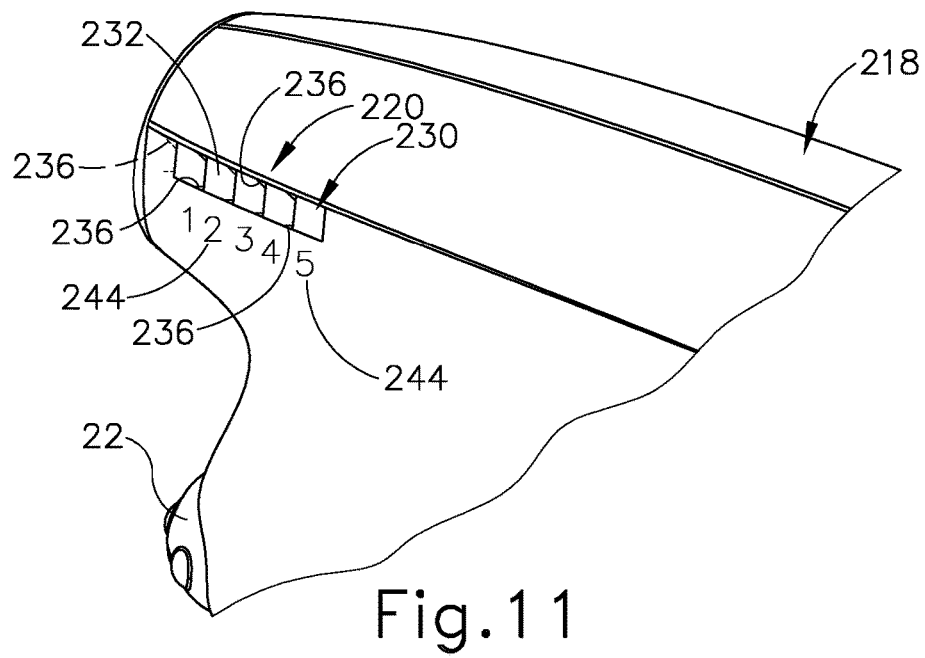
FIG. 11 depicts an enlarged perspective view of the handle assembly with the second additive usage indicator of FIG. 9.
Figure 12A:
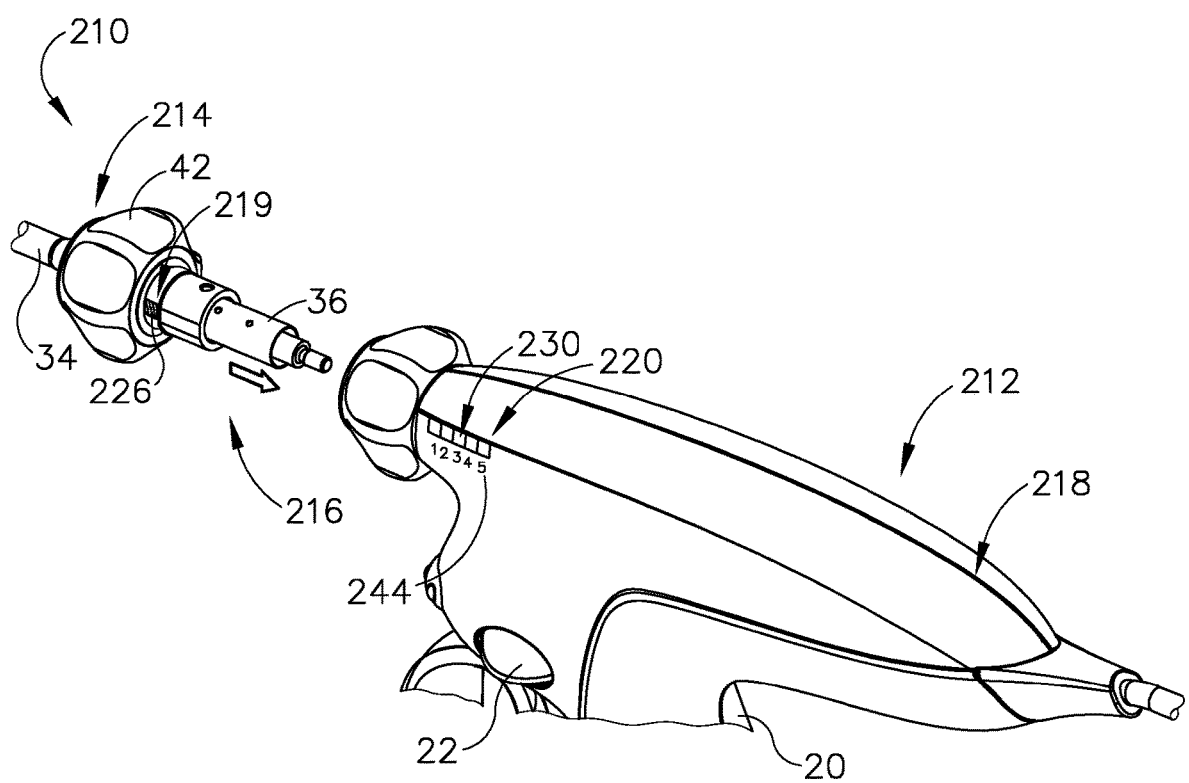
FIG. 12A depicts an enlarged perspective view of the ultrasonic surgical instrument and the second additive usage indicator of FIG. 9 with the shaft assembly being inserted into the handle assembly.

As shown in FIG. 10, shaft portion (219) of first additive usage indicator (216) includes a detachable counter tab member (226) projecting proximally knob (42). Counter tab member (226) is more particularly frangible connected to shaft assembly (214) such that applying a shear force to counter tab member (226) breaks counter tab member (226) therefrom. Housing portion (220) of second additive usage indicator (216) includes longitudinally extending indicia window (228) into a catch (230) having a longitudinally extending catch tab slot (232). As the proximal portion of shaft assembly (214) is inserted into handle assembly (112) for mechanical and acoustic connection therewith, counter tab member (226) is inserted into a distal opening (not shown) of catch tab slot (232) as shown in FIGS. 11-12A. Catch tab slot (232) includes a plurality of inner ratchet teeth (236) configured to inhibit distal movement of counter tab member (226) relative to housing (218), but allow proximal movement of counter tab member (226) relative to housing (218). In this respect, proximal movement of shaft assembly (214) urges counter tab member (226) into catch tab slot (232) for capture by inner ratchet teeth (236) until bayonet slot (138) (see FIG. 7C) receives bayonet pin (140) (see FIG. 7C) for mechanically coupling shaft assembly (214) to handle assembly (212). Rotating shaft assembly (214) for such connection with counter tab member (226) simultaneously captured within catch tab slot (232) breaks counter tab member (226) from shaft assembly (2214) to be retained within catch tab slot (232) as discussed below in greater detail.

Figure 12B:
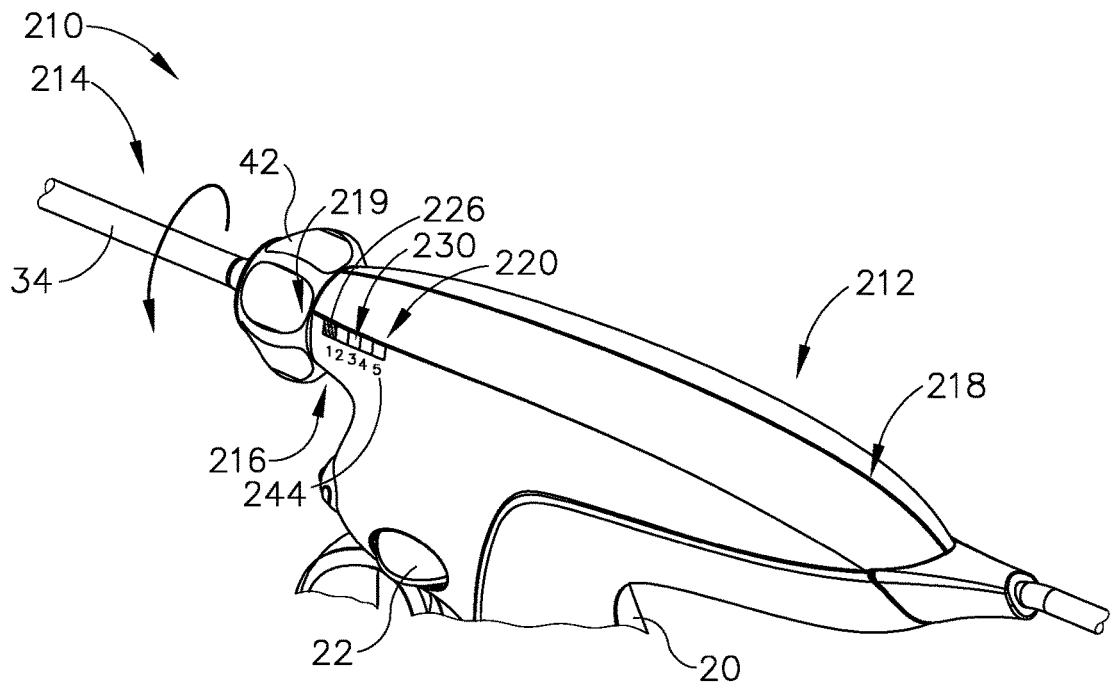
FIG. 12B depicts the enlarged perspective view of the ultrasonic surgical instrument and the second additive usage indicator similar to FIG. 12A, but showing the shaft assembly being connected to the handle assembly and the second additive usage indicator indicating the first use of the handle assembly.
Figure 12C:
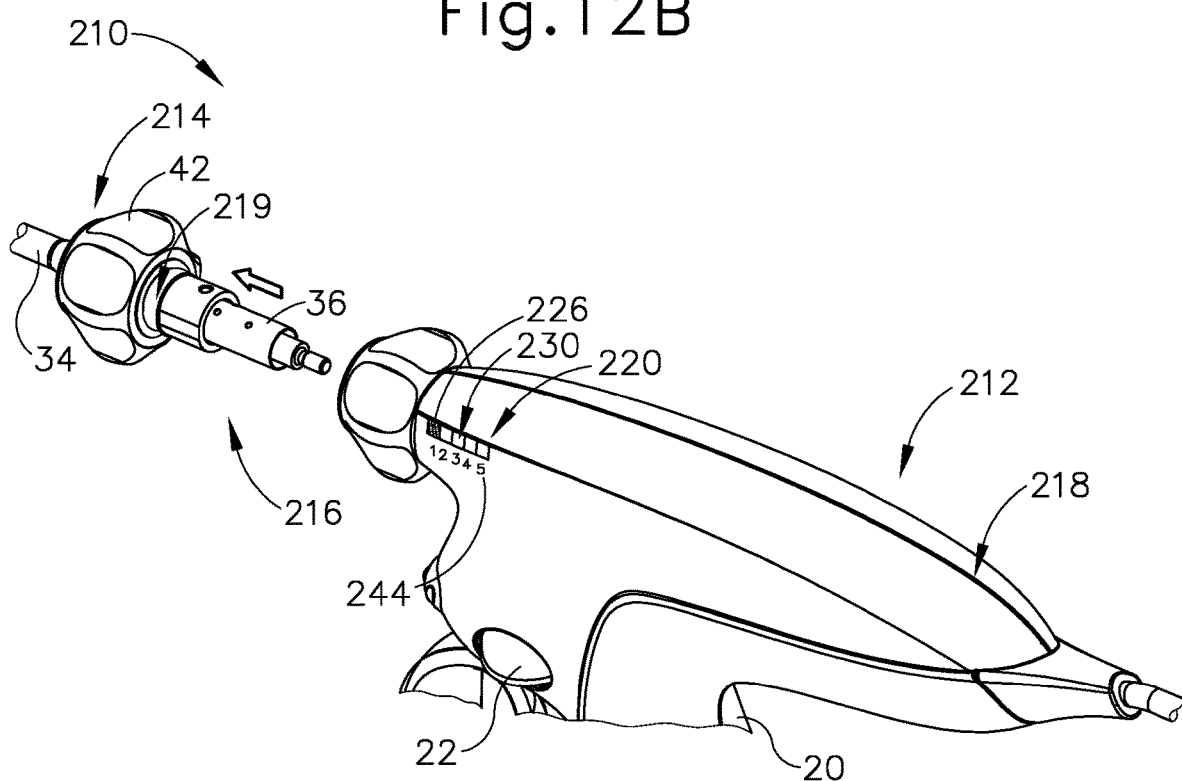
FIG. 12C depicts the enlarged perspective view of the ultrasonic surgical instrument and the second additive usage indicator similar to FIG. 12B, but showing the shaft assembly being removed from the handle assembly after use and the second additive usage indicator indicating the first use of the handle assembly.
Figure 12D:
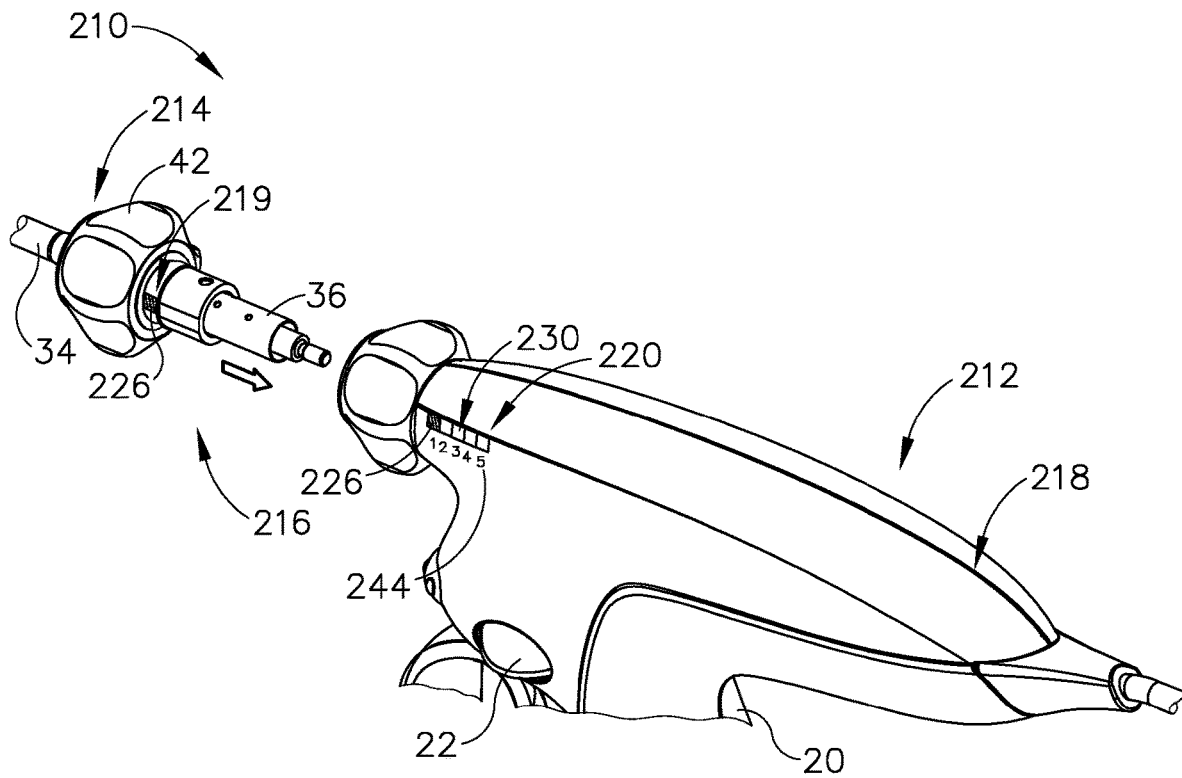
FIG. 12D depicts the enlarged perspective view of the ultrasonic surgical instrument and the second additive usage indicator similar to FIG. 12C, but showing another, replacement shaft assembly being inserted into the handle assembly.
Figure 12E:
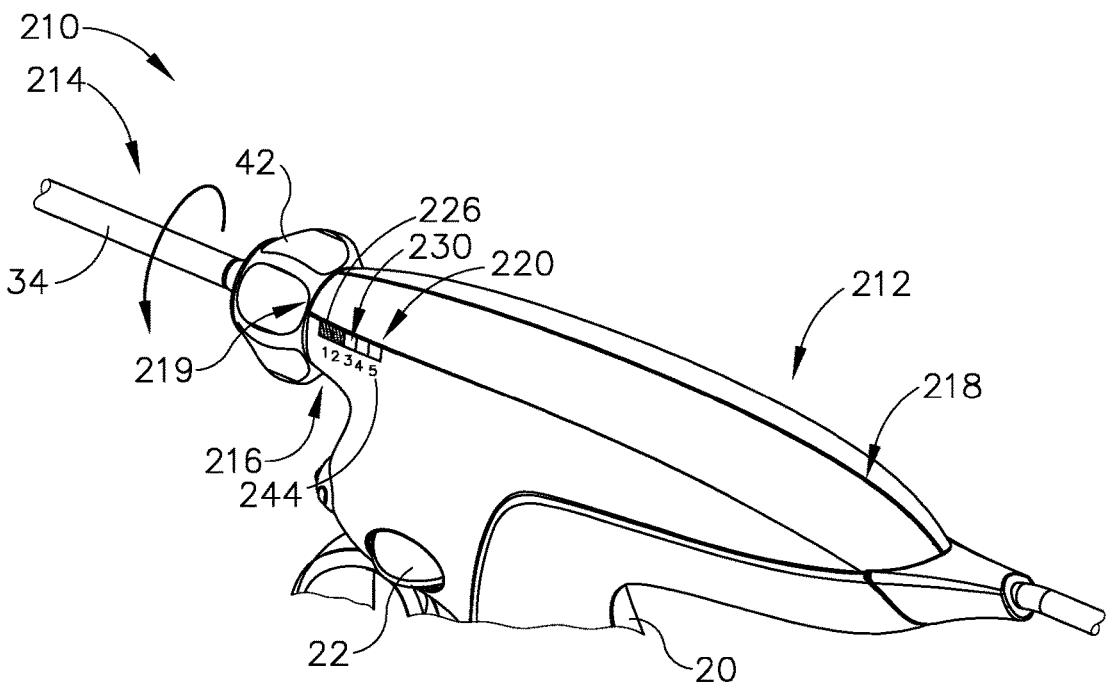
FIG. 12E depicts the enlarged perspective view of the ultrasonic surgical instrument and the second additive usage indicator similar to FIG. 12D, but showing the replacement shaft assembly being connected to the handle assembly and the second additive usage indicator indicating a second use of the handle assembly.
Figure 13:
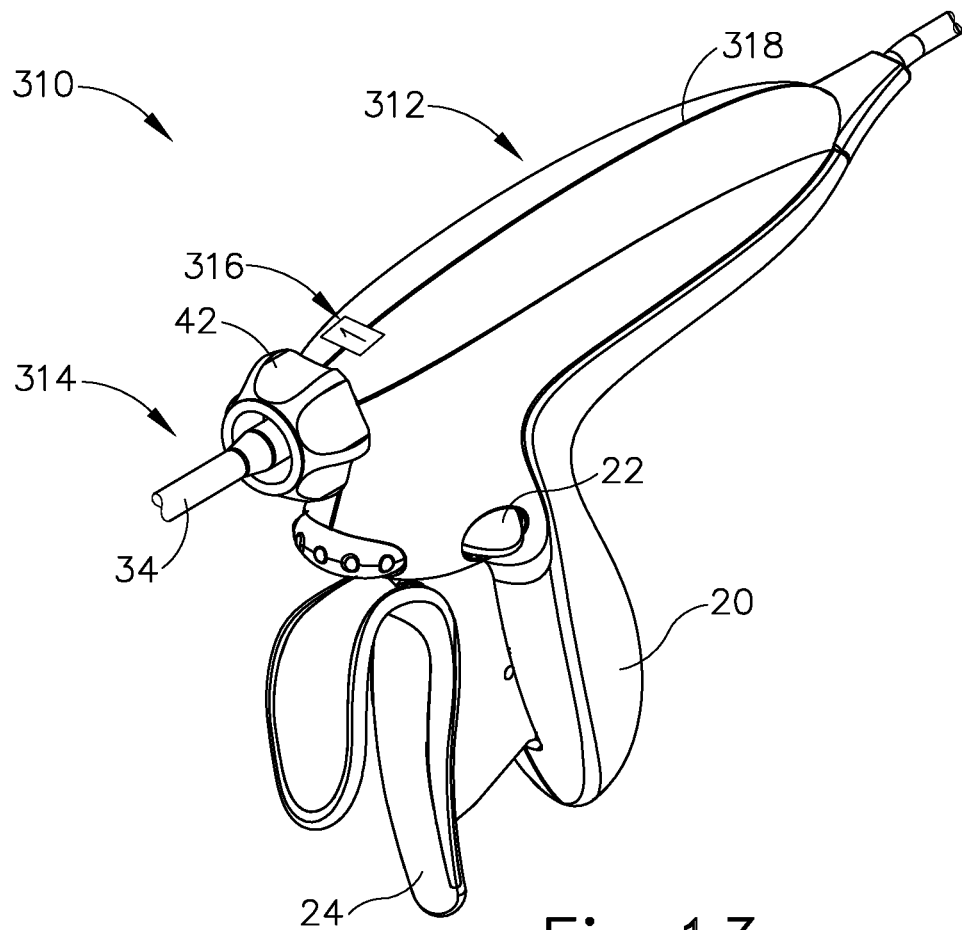
FIG. 13 depicts a perspective view of an enlarged perspective view of a fourth exemplary ultrasonic surgical instrument having a first wheel ratchet usage indicator for a shaft assembly and a handle assembly.

As briefly discussed above, indicia window (228) into catch tab slot (232) provides clinician with visual identification of the presence of any counter tab members (226) received therein. In addition, housing (218) further includes a series of counter indices (244), which are longitudinally and linearly positioned on housing (244) increasing in the proximal direction. The present example of counter indices (244) includes proximally increasing numbers "1," "2," "3," "4," and "5" and are respectively configured to correspond to each replacement shaft assembly (214) used with handle assembly (212) in relation to counter tab members (226). For example, as shown in FIG. 12B, a first counter tab member (226) longitudinally aligns with counter indicia (244) "1" to indicate to the clinician through indicia window (228) that handle assembly (212) is in its first use.

Given that inner ratchet teeth (232) are configured to capture counter tab member (226), capture tab member (226) remains within catch (230) upon removal of shaft assembly (214) from handle assembly (212). With respect to FIGS. 12D-12E, additional replacement shaft assemblies (214) with respective counter tab members (226) used with handle assembly (212) simply urge each captured counter tab member (226) proximally to align with the successive counter indicia (244). Thus, even after removal of one or more shaft assemblies (214) from handle assembly (212), the number of use cycles based shaft assembly connections (214) is recorded with handle assembly (212) throughout the remaining use state. In one example, counter tab members (226) may in addition or alternatively include a radio-frequency identification (RFID) tag for recording uses.

Once catch (230) is full of counter ring members (226), first additive usage indicator is visually in the used state. In addition, catch (230) is configured to receive no more counter tab members (226) than those that correspond to the predetermined number of use cycles based on replacement shaft assemblies (214). An additional counter tab member (226) greater than the predetermined number of use cycles, which in the present example is five, is configured to block acoustic and mechanical connection of another replacement shaft assembly (214) to handle assembly. First additive usage indicator (216) is thereby configured to inhibit inadvertently using handle assembly (212) beyond the predetermined number of use cycles.

In use, with respect to FIGS. 12A-12G, the clinician connects the first replacement shaft assembly (214) to handle assembly (212) such that counter tab member (226) is captured by catch (230) in alignment with the first indicia (244) for indicating the first use to clinician. Following treatment of the patient, shaft assembly (214) is disconnected from handle assembly (212) thereby detaching counter tab member (226) from shaft assembly (214). Handle assembly (212) is then prepped, such as by heating and/or sterilizing, for another surgical procedure and another replacement shaft assembly (214) is connected to handle assembly (212). The second counter tab member (226) urges the first counter tab member (226) in alignment with the second indicia for indicating the second use to the clinician. Such reuse continues as shown in FIGS. 12A-12G in the remaining use state until catch (230) is full of counter tab members (226) in the used state.

C. First Wheel Ratchet Usage Indicator

FIGS. 13-16B illustrate a fourth exemplary ultrasonic surgical instrument (310) having a handle assembly (312) configured to be operated up to a predetermined number of use cycles, a shaft assembly (314) configured for a single use cycle of treatment, and a first wheel ratchet usage indicator (316). With respect to FIGS. 13-14, first wheel ratchet usage indicator (316) is integrated into portions of shaft assembly (314) and a housing (318) of handle assembly (312) for recording and indicating each respective use cycle of handle assembly (312) in a use remaining state to a used state. First wheel ratchet usage indicator (316) has a shaft portion (319) that cooperates with a housing portion (320) upon connection of shaft assembly (314) to handle assembly (312) to thereby direct first wheel ratchet usage indicator (316) toward the used state with each replacement shaft assembly (314). Once shaft assembly (314) has been replaced the predetermined number of use cycles, first wheel ratchet usage indicator (316) indicates the used state of handle assembly (312) to the clinician. Such indication of first wheel ratchet usage indicator (316) is visual as well as a lockout, which inhibits operation of handle assembly (312).

Figure 14:
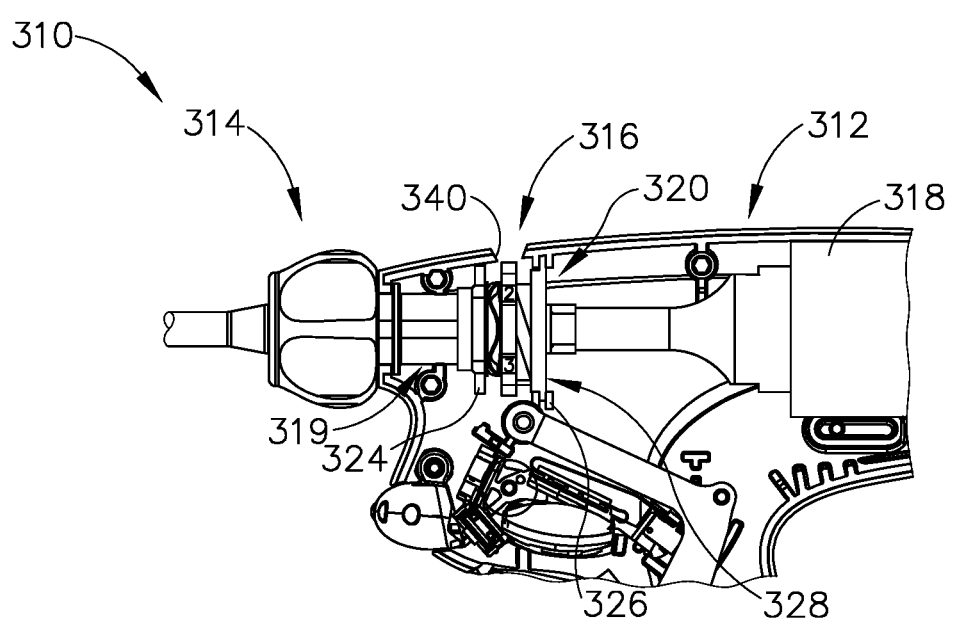
FIG. 14 depicts an enlarged side view of the ultrasonic surgical instrument and the first wheel ratchet usage indicator of FIG. 13 having various components hidden for clarity.
Figure 15:
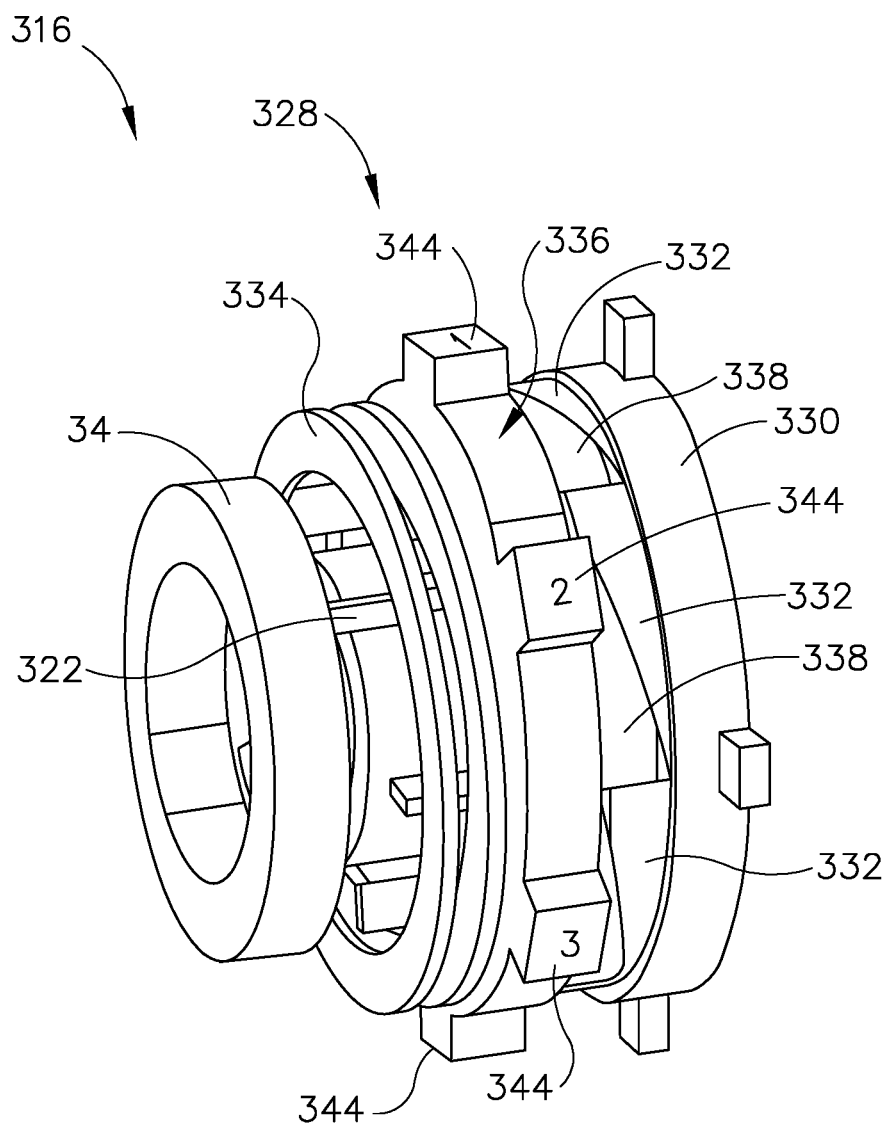
FIG. 15 depicts a perspective view of the first wheel ratchet usage indicator of FIG. 13.

As shown in FIGS. 14-15, shaft portion (319) of first wheel ratchet usage indicator (316) includes an actuator (322) extending proximally from outer tube (34) toward housing portion (320). Housing portion (320) of first wheel ratchet usage indicator (316) includes a distal housing mount (324), a proximal housing mount (326), and a clutch arrangement (328) mounted therebetween. Clutch arrangement (328) more particularly includes a ratchet base (330) with a plurality of base ratchet teeth (332) fixed relative to proximal housing mount (326), a biasing element, such as a compressed coil spring (334), and a wheel ratchet (336). Wheel ratchet (336) is rotatably mounted about the longitudinal axis and has a plurality of slip ratchet teeth (338). Wheel ratchet (336) is thus configured to indicate usage through an indicia window (340) extending through an upper surface of housing (318) as discussed below in greater detail. Compressed coil spring (334) is longitudinally captured between wheel ratchet (336) and distal housing mount (326) and thereby biases slip ratchet teeth (338) of wheel ratchet (336) against base ratchet teeth (332) of ratchet base (330).

Wheel ratchet (336) and ratchet base (330) are generally cylindrical and coaxially aligned along the longitudinal axis such that slip ratchet teeth (338) and base ratchet teeth (332) are angularly positioned about the longitudinal axis. Each of coil spring (334), ratchet base (330), and wheel ratchet (336) further includes a longitudinally extending hole therethrough configured to receive waveguide (38) for connection within ultrasonic transducer (26). With respect to FIG. 15, engagement between slip ratchet teeth (338) and base ratchet teeth (332) as coil spring (334) proximally urges wheel ratchet (336) toward ratchet base (33) and creates a camming effect that causes slip ratchet teeth (338) to rotate clockwise against base ratchet teeth (332) until effectively locked thereagainst. Ratchet base (330) thus inhibits further clockwise rotation of wheel ratchet (336). In contrast, forced counterclockwise rotation of wheel ratchet (336) that overcomes the camming effect from coil spring (334) provides for further counterclockwise rotation and ratcheting of wheel ratchet (336) relative to ratchet base (330) as discussed below in greater detail. In the present example, "clockwise" and "counterclockwise" refer to rotation of wheel ratchet (336) as viewed from a distal end of clutch arrangement (328).

In the present example, shaft assembly (314) mechanically and acoustically couples to handle assembly (312) by rotation similar to shaft and handle assemblies (114, 112) (see FIG. 7D). Insertion of outer tube (34) into housing (318) engages actuator (322) with an inner portion of wheel ratchet (336) as shown in FIG. 15. For connection of shaft assembly (314), rotating outer tube (34) counterclockwise similarly rotates actuator (322) about the longitudinal axis while engaged with wheel ratchet (336). Wheel ratchet (336) thereby simultaneously rotates counterclockwise for each connection of a replacement shaft assembly (314) from handle assembly (312). However, because ratchet base (330) locks clockwise movement wheel ratchet (336), the clockwise connection of shaft assembly (314) from handle assembly (312) does not affect the angular position of wheel ratchet (336). The angular position of wheel ratchet (336) is thus configured to indicate to the clinician the use remaining state as it is rotated in the counterclockwise direction toward the used state by successive connections of replacement shaft assemblies (314).

As briefly discussed above, indicia window (340) (see FIG. 14) provides clinician with visual identification of the angular position of wheel ratchet (336). The relative angular position is recorded by a series of counter indices (344), which are angularly positioned about wheel ratchet (336) and increasing in the clockwise direction. The present example of counter indices (344) includes clockwise increasing numbers "1," "2," "3," "4," and "5" and are respectively configured to correspond to each replacement shaft assembly (314) used with handle assembly (312) in relation to the rotational position of wheel ratchet (336). For example, as shown in FIGS. 14-15, a first counter indicia (344) "1" transversely aligns through indicia window (340) to indicate to the clinician that handle assembly (312) is in its first use.

Successive connections of replacement shaft assemblies (314) continue to rotate wheel ratchet (336) until a fifth counter indicia (344) "5" transversely aligns through indicia window (340) to visually indicate the used state of handle assembly (312). In addition, clutch arrangement (328) is configured to mechanically inhibit further connection of replacement shaft assemblies (314) greater than the predetermined number of use cycles. More particularly, wheel ratchet (336) and ratchet base (330) have cooperating blockers (not shown) that longitudinally overlap and engage once wheel ratchet (336) is in the used state to inhibit further use. First wheel ratchet usage indicator (316) is thereby configured to inhibit inadvertently using handle assembly (312) beyond the predetermined number of use cycles.

Figure 16B:
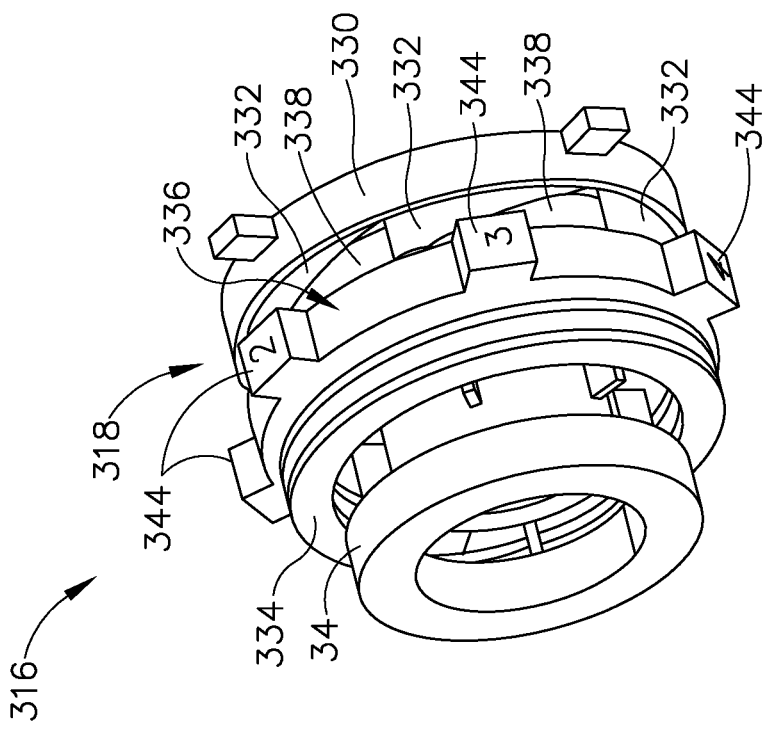
FIG. 16B depicts the perspective view of the first wheel ratchet usage indicator similar to FIG. 16A, but showing the first wheel ratchet usage indicator indicating the second usage.
Figure 16A:
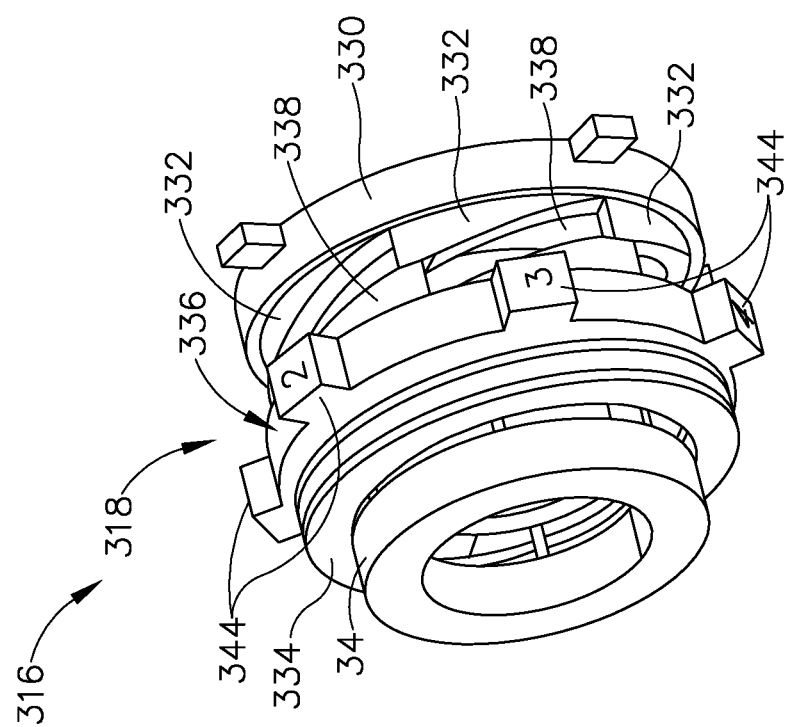
FIG. 16A depicts a perspective view of the first wheel ratchet usage indicator of FIG. 13 actuating from a first usage indication to a second usage indication.

In use, with respect to FIGS. 14-16B, the clinician disconnects first replacement shaft assembly (314) from handle assembly (312) such that actuator (322) urges wheel ratchet (336) with the camming effect counterclockwise in alignment with the first indicia (344) for indicating the first use to clinician. Handle assembly (312) is then prepped, such as by heating and/or sterilizing, for another surgical procedure and another replacement shaft assembly (314) is connected to handle assembly (312). Such reuse continues as shown in FIGS. 16A-16B in the remaining use state until blockers (not shown) on wheel ratchet (336) and ratchet base (330) overlap in the used state.

In an alternative example, shaft assembly (314) mechanically and acoustically couples to handle assembly (312) by rotation in the opposite direction to the directions discussed above. First wheel ratchet usage indicator (316) would thus cooperate with housing portion (320) upon disconnection, rather than connection, of shaft assembly (314) to handle assembly (312). More particularly, upon disconnection of shaft assembly (314), rotating outer tube (34) counterclockwise would thereby rotate actuator (322) about the longitudinal axis while engaged with wheel ratchet (336). The angular position of wheel ratchet (336) may thus be alternatively configured to indicate to the clinician the use remaining state as it is rotated in the counterclockwise direction toward the used state by successive disconnections of replacement shaft assemblies (314). The particular use cycle indications may progress upon either connection or disconnection of shaft assembly (312) for this example and other examples described herein.

D. Second Wheel Ratchet Usage Indicator

Figure 19:
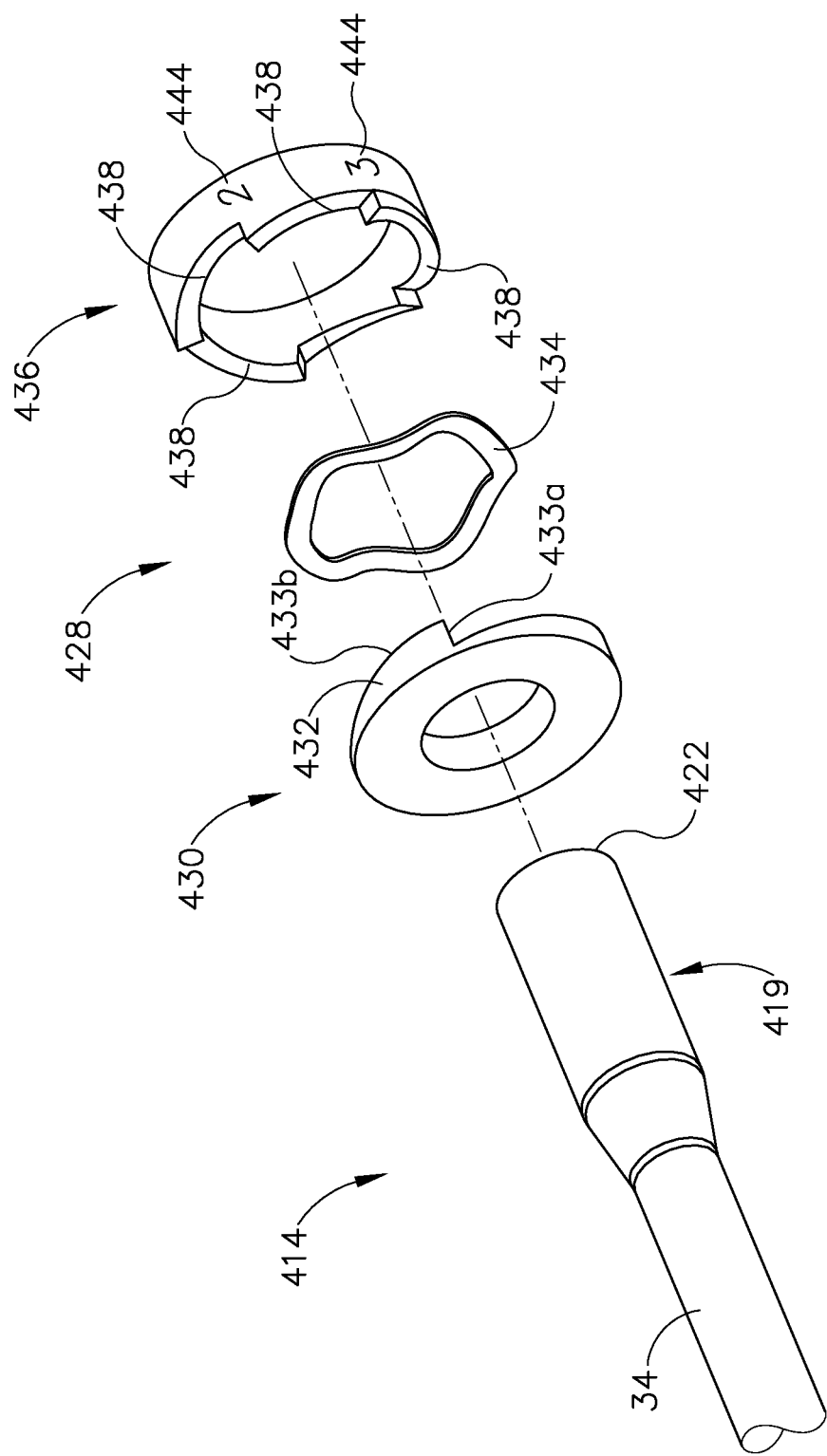
FIG. 19 depicts an exploded perspective view of the second wheel ratchet usage indicator of FIG. 17.

FIGS. 17-19 illustrate a fifth exemplary ultrasonic surgical instrument (410) having a handle assembly (412) configured to be operated up to a predetermined number of use cycles, a shaft assembly (414) configured for a single use cycle of treatment, and a second wheel ratchet usage indicator (416). Second wheel ratchet usage indicator (416) is integrated into portions of shaft assembly (414) and a housing (418) of handle assembly (412) for recording and indicating each respective use cycle of handle assembly (412) in a use remaining state to a used state. Second wheel ratchet usage indicator (416) has a shaft portion (419) that cooperates with a housing portion (420) upon connection of shaft assembly (414) to handle assembly (412) to thereby direct second wheel ratchet usage indicator (416) toward the used state with each replacement shaft assembly (414). Once shaft assembly (414) has been replaced the predetermined number of use cycles, second wheel ratchet usage indicator (416) indicates the used state of handle assembly (412) to the clinician. Such indication of second wheel ratchet usage indicator (416) is visual as well as a lockout, which inhibits operation of handle assembly (412).

As shown in FIGS. 18-19, shaft portion (419) of second wheel ratchet usage indicator (416) includes a cylindrical distal end actuator (422) extending proximally from outer tube (34) toward housing portion (420). Housing portion (420) of second wheel ratchet usage indicator (416) includes distal and proximal housing mounts (324, 326) (see FIG. 14) and a clutch arrangement (428) mounted therebetween. Clutch arrangement (428) more particularly includes a ratchet plate (430) with a plurality of ramp ratchet teeth (432), a biasing element, such as a compressed wave spring (434), and a wheel ratchet (436). Wheel ratchet (436) is rotatably mounted about the longitudinal axis and has a plurality of slip ratchet teeth (438). Wheel ratchet (436) is thus configured to indicate usage through an indicia window (440) extending through a side surface of housing (418) as discussed below in greater detail. Compressed wave spring (434) is longitudinally captured between wheel ratchet (436) and ratchet plate (430) and thereby biases wheel ratchet (436) and ratchet plate (430) away from each other.

Wheel ratchet (436) and ratchet plate (430) are generally cylindrical and coaxially aligned along the longitudinal axis such that slip ratchet teeth (438) and base ratchet teeth (432) are angularly positioned about the longitudinal axis. Each of wave spring (434), ratchet plate (430), and wheel ratchet (436) further includes a longitudinally extending hole therethrough configured to receive waveguide (38) (see FIG. 4) for connection within ultrasonic transducer (26) (see FIG. 4). Without shaft assembly (414) introduced in handle assembly (412), ratchet plate (430) is disengaged from wheel ratchet (436) and thus unable to rotate wheel ratchet (436). In addition, wheel ratchet (436) further includes an arrester (not shown) to inhibit inadvertent clockwise or counterclockwise rotation. In the present example, "clockwise" and "counterclockwise" refer to rotation of wheel ratchet (436) as viewed from a distal end of clutch arrangement (428).

In the present example, shaft assembly (414) mechanically and acoustically couples to handle assembly (412) by rotation similar to shaft and handle assemblies (114, 112) (see FIG. 7D). Insertion of outer tube (34) into housing (418) engages actuator (422) into frictional engagement with ratchet plate (430) by overcoming wave spring (434) bias and urging ratchet plate (430) proximally such that ramp ratchet teeth (432) of ratchet plate (430) engage with slip ratchet teeth (438) of wheel ratchet (436). Rotating outer tube (34) clockwise for mechanical connection similarly rotates actuator (422) about the longitudinal axis and simultaneously rotates wheel ratchet (436) for each connection of a replacement shaft assembly (414) to handle assembly (412). More particularly, engagement portions (433a) of ramp ratchet teeth (432) engage slip ratchet teeth (438) to overcome arrester (not shown) in the clockwise direction for connection of shaft assembly (414). In contrast, ramp portions (433b) of ramp ratchet teeth (432) are unable to overcome arrester (not shown) and thus simply slip by slip ratchet teeth (438) in the counterclockwise direction for removal of shaft assembly (414).

As briefly discussed above, indicia window (440) provides clinician with visual identification of the angular position of wheel ratchet (436). The relative angular position is recorded by a series of counter indices (444), which are angularly positioned about wheel ratchet (436) and increasing in the clockwise direction. The present example of counter indices (444) includes clockwise increasing numbers "1," "2," "3," "4," and "5" and are respectively configured to correspond to each replacement shaft assembly (414) used with handle assembly (412) in relation to the rotational position of wheel ratchet (436). For example, as shown in FIG. 17, a first counter indicia (444) "1" transversely aligns through indicia window (440) to indicate to the clinician that handle assembly (412) is in its first use.

Successive connections of replacement shaft assemblies (414) continue to rotate wheel ratchet (436) until a fifth counter indicia (444) "5" transversely aligns through indicia window (440) to visually indicate the used state of handle assembly (412). In addition, clutch arrangement (428) is configured to mechanically inhibit further connection of replacement shaft assemblies (414) greater than the predetermined number of use cycles. More particularly, arrester (not shown) engages wheel ratchet (436) in the used state to inhibit further counterclockwise rotation thereof. Second wheel ratchet usage indicator (416) is thereby configured to inhibit inadvertently using handle assembly (412) beyond the predetermined number of use cycles.

In use, with respect to FIGS. 18-19, the clinician connects first replacement shaft assembly (414) to handle assembly (412) such that actuator (422) urges wheel ratchet (436) in alignment with the first indicia (444) for indicating the first use to clinician. Following treatment of the patient, shaft assembly (414) is disconnected from handle assembly (412) by slipping ramp portions (433b) of ramp ratchet teeth (432) by slip ratchet teeth (438). Handle assembly (412) is then prepped, such as by heating and/or sterilizing, for another surgical procedure and another replacement shaft assembly (414) is connected to handle assembly (412). Actuator (426) of the second replacement shaft assembly (414) urges wheel ratchet (436) in alignment with the second indicia for indicating the second use to the clinician. Such reuse continues in the remaining use state until arrester (not shown) engages wheel ratchet (436) in the used state.

E. Third Wheel Ratchet Usage Indicator

FIGS. 20-25C illustrate a sixth exemplary ultrasonic surgical instrument (510) having a handle assembly (512) configured to be operated up to a predetermined number of use cycles, a shaft assembly (514) configured for a single use cycle of treatment, and a third wheel ratchet usage indicator (516). With respect to FIGS. 20-21, third wheel ratchet usage indicator (516) is integrated into portions of shaft assembly (514) and a housing (518) of handle assembly (512) for recording and indicating each respective use cycle of handle assembly (512) in a use remaining state to a used state. Third wheel ratchet usage indicator (516) has a shaft portion (519) that cooperates with a housing portion (520) upon connection of shaft assembly (514) to handle assembly (512) to thereby direct third wheel ratchet usage indicator (516) toward the used state with each replacement shaft assembly (514). Once shaft assembly (514) has been replaced the predetermined number of use cycles, third wheel ratchet usage indicator (516) indicates the used state of handle assembly (512) to the clinician. Such indication of third wheel ratchet usage indicator (516) is visual as well as a lockout, which inhibits operation of handle assembly (512).

As shown in FIGS. 21-23B, shaft portion (519) of third wheel ratchet usage indicator (516) includes an outer surface of outer tube (34) as an actuator (522). Housing portion (520) of third wheel ratchet usage indicator (516) includes a ratchet knob (542) having a knob cover (524), which includes an indicia window (528). Ratchet knob (542) operates similar to knob (42) (see FIG. 2) once receiving outer tube (34) for treatment, but is a portion of housing (518) rather than shaft assembly (514). Ratchet knob (542) more particularly includes a ratchet mechanism (530) with a ratchet pawl tooth (532), a biasing element, such as a tension spring (534), and a wheel ratchet (536). Wheel ratchet (536) is rotatably mounted about the longitudinal axis and has a plurality of slip ratchet teeth (538). Wheel ratchet (536) is thus configured to indicate usage through indicia window (528) in knob cover (524) as discussed below in greater detail.

Wheel ratchet (536) generally cylindrical and coaxially aligned along the longitudinal axis such that slip ratchet teeth (538) are angularly positioned about the longitudinal axis. Wheel ratchet (536) further includes a longitudinally extending hole therethrough configured to receive waveguide (38) (see FIG. 4) for connection within ultrasonic transducer (26) (see FIG. 4). Ratchet pawl tooth (532) of ratchet mechanism (530) is configured to urge wheel ratchet (536) counterclockwise, but inhibit clockwise rotation. In addition, third wheel ratchet usage indicator (516) further includes an arrester (540). Arrester (540) has a plurality of detents (544) configured to engage a proximal end of wheel ratchet (536) to further inhibit inadvertent clockwise or counterclockwise rotation wheel ratchet (536). In the present example, "clockwise" and "counterclockwise" refer to rotation of wheel ratchet (536) as viewed from a distal end of ratchet knob (542).

With respect to FIGS. 23A-23B, ratchet mechanism includes a base (546) that movably receives a pivot core (548). Pivot core (548) has an outer slot (550) that spirals about an outer surface of the pivot core (548) such that rotation of pivot core (548) also causes pivot core (548) to transversely move upward and downward within base (546) between respective contracted and expanded states. Ratchet pawl tooth (532) extends radially outward from pivot core (548) to similarly pivot and transversely move therewith for urging movement of wheel ratchet (536) when shaft assembly (514) is inserted into ratchet knob (542).

Figure 24B:
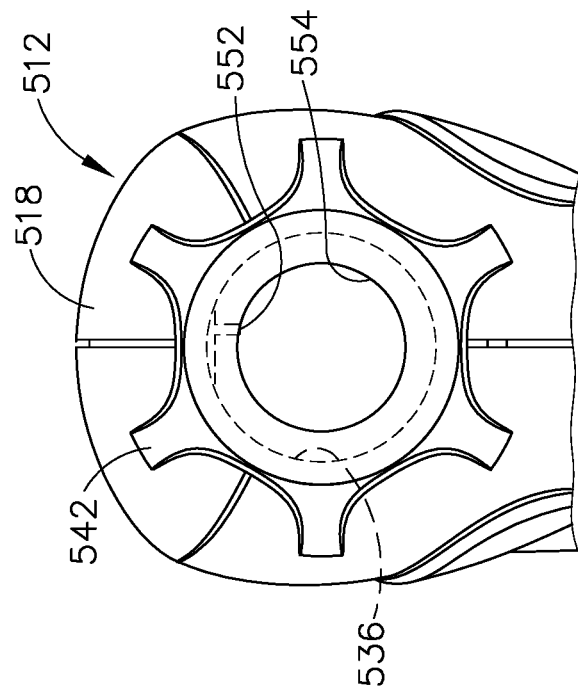
FIG. 24B depicts the enlarged distal end view of the ultrasonic surgical instrument similar to FIG. 24A, but showing the ratchet mechanism of FIG. 23B in the expanded state.
Figure 24A:
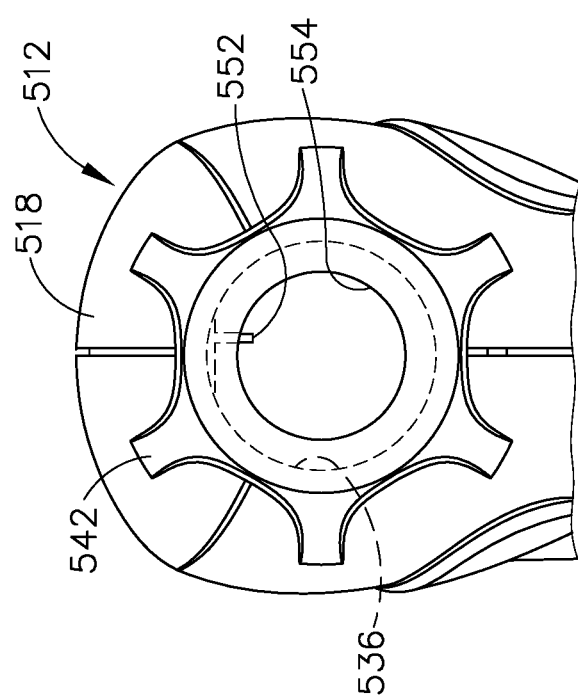
FIG. 24A depicts an enlarged distal end view of the ultrasonic surgical instrument of FIG. 20 with the ratchet mechanism of FIG. 23A in the contracted state.

To this end, a lever (552) extends transversely downward from pivot core (548) and into a longitudinal bore (554) through ratchet knob (542) to engage actuator (522) upon connection of shaft assembly (514) with handle assembly (512). As shown in FIG. 24A, lever (522) is in the path along which outer tube (34) is inserted into longitudinal bore such that actuator (522) engages lever (522) to rotate lever and, in turn, rotate pivot core (548) to urge wheel ratchet (536). Lever (522) also moves transversely upward with pivot core (548) as lever (522) rotates in order to transversely clear the introduction path of outer tube (34) as shown in FIG. 24B.

Figure 25A:
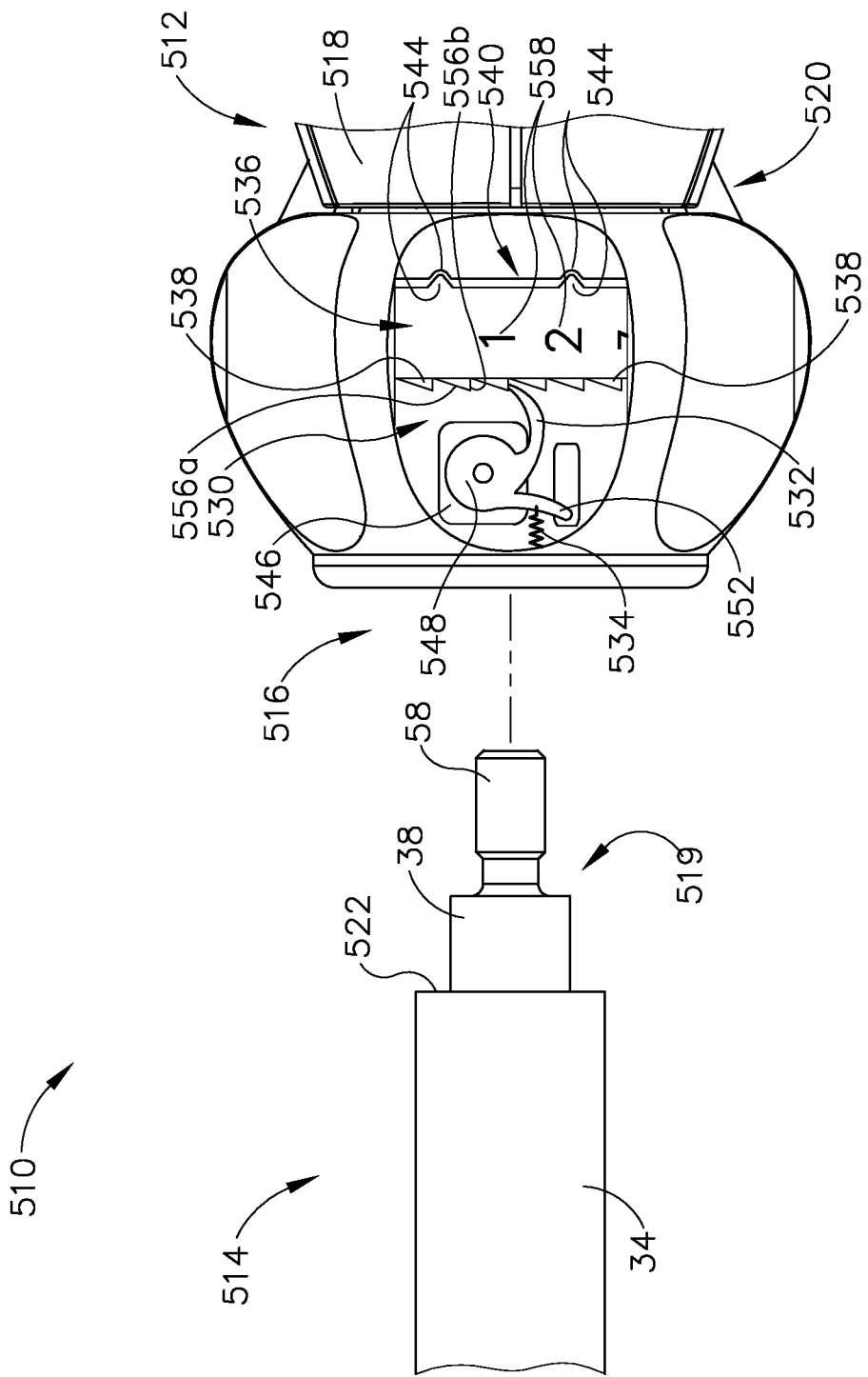
FIG. 25A depicts an enlarged top view of the ultrasonic surgical instrument and the third wheel ratchet usage indicator of FIG. 20 with various features hidden for clarity.

In the present example, with respect to FIG. 25A, shaft assembly (514) mechanically and acoustically couples to handle assembly (512) by rotation similar to shaft and handle assemblies (114, 112) (see FIG. 7D). Insertion of outer tube (34) into housing (518) rotates lever (522), pivot core (548), and ratchet pawl tooth (532). With ratchet pawl tooth (532) engaged with one of slip ratchet teeth (538), rotation of ratchet pawl tooth (532) thereby urges wheel ratchet (536) with sufficient force to overcome arrester (540). Removal of outer tube (34) from housing (518) causes, tension spring (534) to rotate pivot core (548) back such that ratchet pawl tooth (532) slips in the clockwise direction along slip ratchet teeth (538). Arrester (540) is configured to secure wheel ratchet (536) such that ratchet pawl tooth (532) slips in the clockwise direction without also rotating wheel ratchet (536) in the clockwise direction. Ratchet pawl tooth (532) and slip ratchet teeth (538) each include engagement and ramp portions (556a, 556b) to further aid to respective urging and slipping of wheel ratchet (536) similar to those discussed above in other examples herein.

Figure 20:
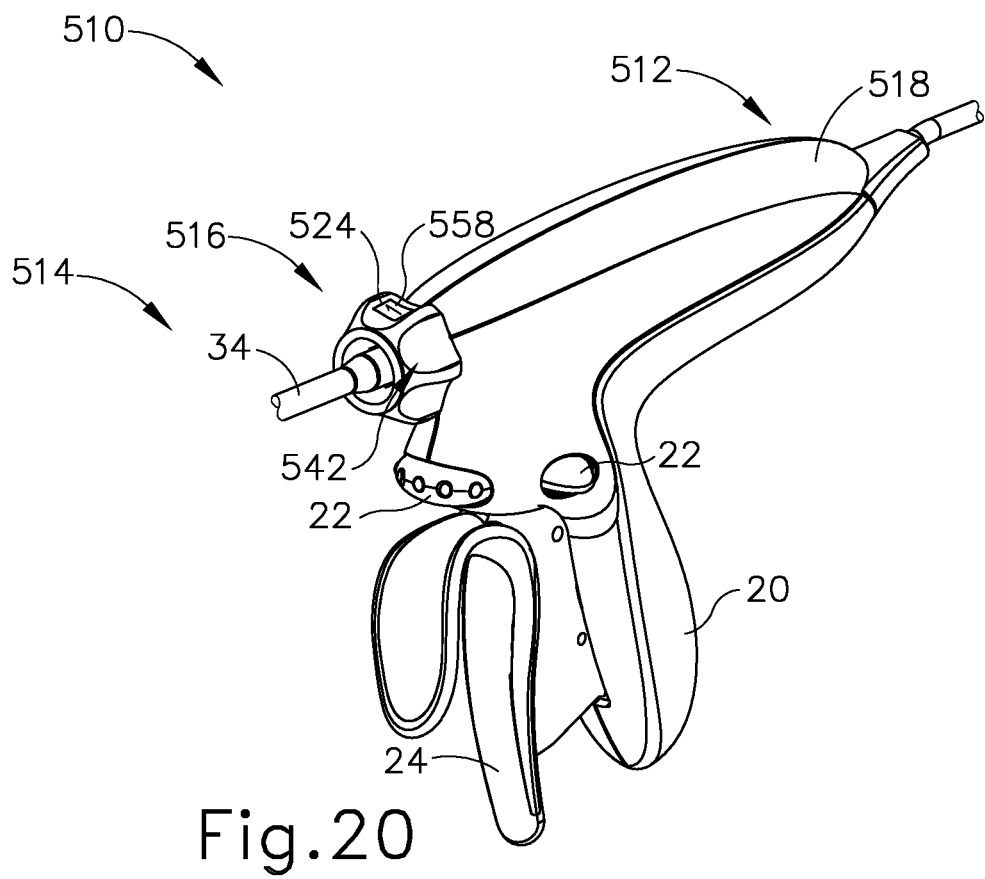
FIG. 20 depicts an enlarged perspective view of a sixth exemplary ultrasonic surgical instrument having a third wheel ratchet usage indicator for a shaft assembly and a handle assembly.
Figure 21:
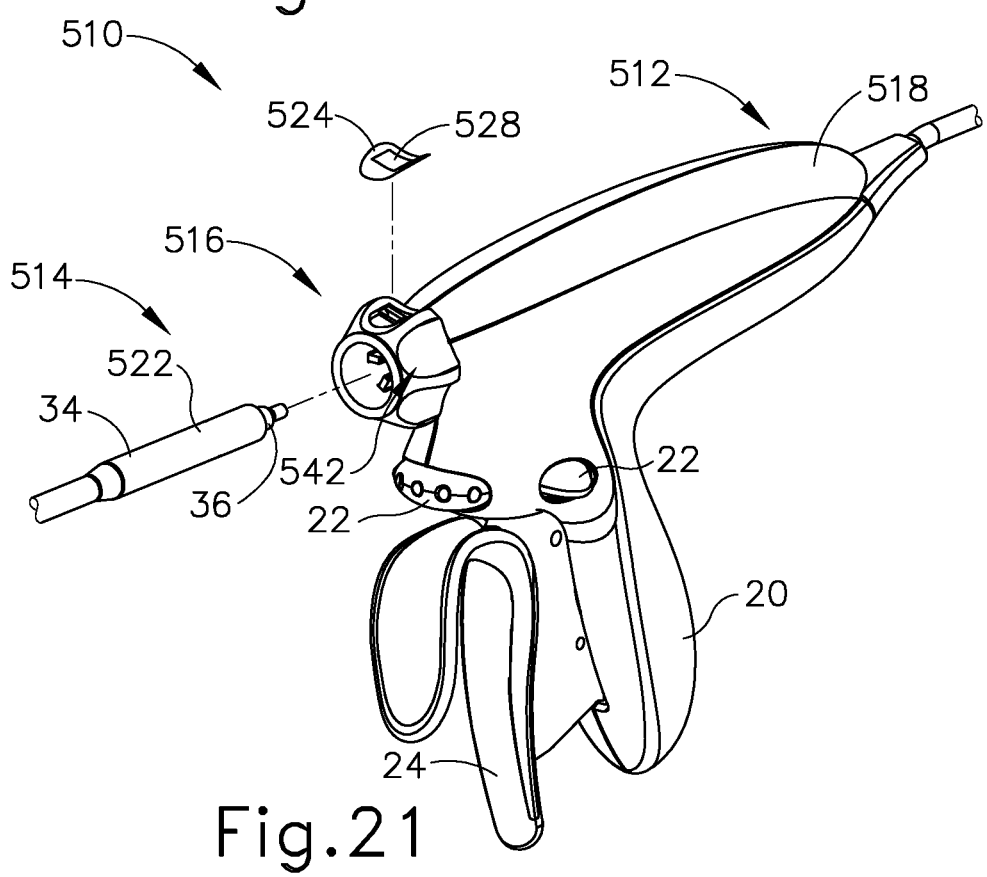
FIG. 21 depicts a partially exploded, enlarged perspective view of the ultrasonic surgical instrument of FIG. 20.

As briefly discussed above, indicia window (528) (see FIG. 20) provides clinician with visual identification of the angular position of wheel ratchet (536). The relative angular position is recorded by a series of counter indices (558), which are angularly positioned about wheel ratchet (536) and increasing in the clockwise direction. The present example of counter indices (558) includes clockwise increasing numbers "1," "2," "3," "4," and "5" and are respectively configured to correspond to each replacement shaft assembly (514) used with handle assembly (512) in relation to the rotational position of wheel ratchet (536). For example, as shown in FIG. 20 and FIG. 25A, a first counter indicia (558) "1" transversely aligns through indicia window (528) to indicate to the clinician that handle assembly (512) is in its first use.

Successive connections of replacement shaft assemblies (414) continue to rotate wheel ratchet (536) until a fifth counter indicia (544) "5" transversely aligns through indicia window (528) to visually indicate the used state of handle assembly (512). In addition, ratchet knob (542) is configured to mechanically inhibit further connection of replacement shaft assemblies (514) greater than the predetermined number of use cycles. More particularly, arrester (540) engages wheel ratchet (536) in the used state to inhibit further counterclockwise rotation thereof. Third wheel ratchet usage indicator (516) is thereby configured to inhibit inadvertently using handle assembly (512) beyond the predetermined number of use cycles.

Figure 25B:
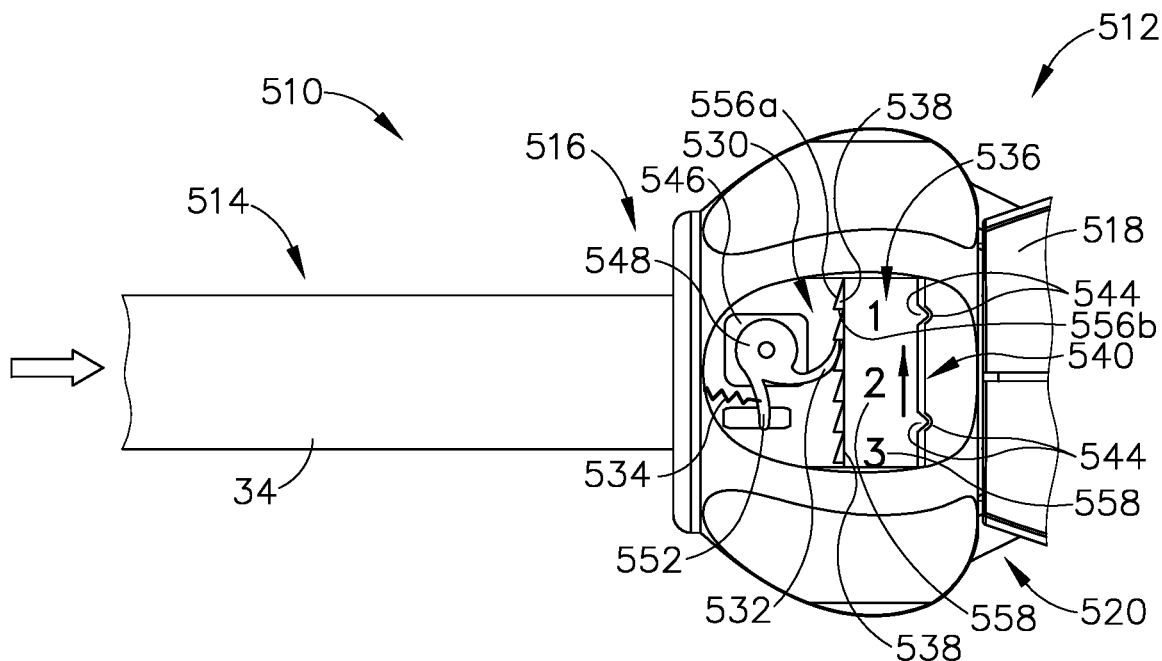
FIG. 25B depicts the enlarged top view of the ultrasonic surgical instrument and the third wheel ratchet usage indicator similar to FIG. 25A, but showing the shaft assembly being inserted into the handle assembly and the ratchet mechanism urging the ratchet wheel to indicate a second usage.
Figure 25C:
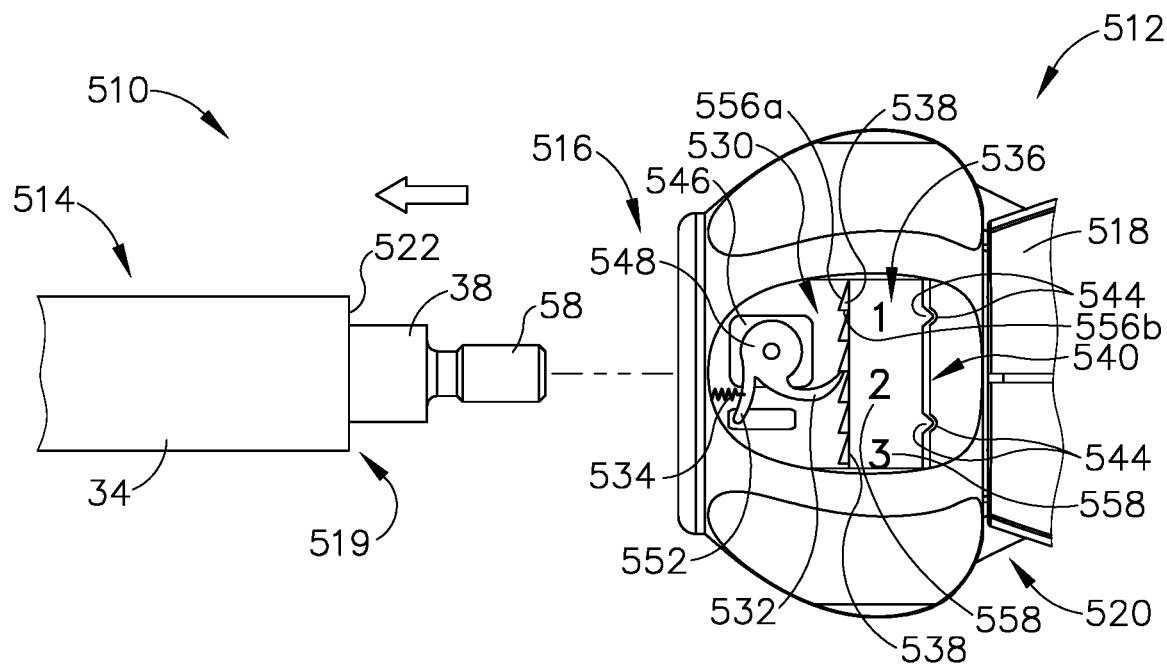
FIG. 25C depicts the enlarged top view of the ultrasonic surgical instrument and the third wheel ratchet usage indicator similar to FIG. 25B, but showing the shaft assembly being removed from the handle assembly after use and the third wheel ratchet usage indicator indicating the second use of the handle assembly.

In use, with respect to FIGS. 25A-25C, the clinician connects first replacement shaft assembly (514) to handle assembly (512) such that actuator (522) urges wheel ratchet (536) in alignment with the first indicia (558) for indicating the first use to clinician. Following treatment of the patient, shaft assembly (514) is disconnected from handle assembly (512) by slipping ramp portions (556b) of ratchet pawl tooth (532) by slip ratchet teeth (538). Handle assembly (512) is then prepped, such as by heating and/or sterilizing, for another surgical procedure and another replacement shaft assembly (514) is connected to handle assembly (512). Actuator (522) of the second replacement shaft assembly (514) urges wheel ratchet (536) in alignment with the second indicia for indicating the second use to the clinician. Such reuse continues in the remaining use state until arrester (540) engages wheel ratchet (536) in the used state.

F. Fourth Wheel Ratchet Usage Indicator

FIGS. 26-28C illustrate a seventh exemplary ultrasonic surgical instrument (610) having a handle assembly (612) configured to be operated up to a predetermined number of use cycles, shaft assembly (14) configured for a single use cycle of treatment, and a fourth wheel ratchet usage indicator (616). With respect to FIGS. 26-27, fourth wheel ratchet usage indicator (616) is integrated into a housing (618) of handle assembly (612) for recording and indicating each respective use cycle of handle assembly (612) in a use remaining state to a used state. Fourth wheel ratchet usage indicator (616) has a housing portion (620) that cooperates with shaft assembly (14) upon connection of shaft assembly (14) to handle assembly (612) to thereby direct fourth wheel ratchet usage indicator (616) toward the used state with each replacement shaft assembly (14). Once shaft assembly (14) has been replaced the predetermined number of use cycles, fourth wheel ratchet usage indicator (616) indicates the used state of handle assembly (612) to the clinician. Such indication of fourth wheel ratchet usage indicator (616) is visual as well as a lockout, which inhibits operation of handle assembly (612).

Housing portion (620) of fourth wheel ratchet usage indicator (616) includes an actuator (622), an indicia window (628) through housing (618), a rotatable wheel mount (624), a ratchet mechanism (630), and a wheel ratchet (636). Actuator (622) of the present example is a distal end of ultrasonic transducer (26). Wheel ratchet (636) is rotatably mounted to wheel mount (624) within housing (618), whereas ratchet mechanism (630) is translatably mounted within housing (618) and biased in the proximal direction toward actuator ultrasonic transducer (26). In the present example, threadably connecting waveguide (38) to ultrasonic transducer (26) distally pulls ultrasonic transducer (26) from a proximal position to a distal position. Thereby, actuator (622) is configured to distally urge ratchet mechanism (630) into engagement with wheel ratchet (636) for rotating wheel ratchet (636) while wheel ratchet (636) is visible to clinician through indicia window (628) as discussed below in greater detail.

In the present example, ratchet mechanism (630) is a pawl tab (632) configured to be distally translated by actuator (622) as ultrasonic transducer (26) slides from the proximal position to the distal position. Pawl tab (632) is more particularly rigid in the longitudinal direction so as to engage and rotate wheel ratchet (636), but resiliently deflectable in the lateral direction. Wheel ratchet (636) has an upper ratchet gear (638) with a plurality of radially projecting slip ratchet teeth (640) about rotatable wheel mount (624). Upper ratchet gear (638) is attached to and extending upward from a lower wheel body (640). Pawl tab (632) is thus configured to engage slip ratchet teeth (640) while moving the distal direction and urge wheel ratchet (636) in the clockwise direction, but inhibit movement in the counterclockwise direction. In addition, fourth wheel ratchet usage indicator (616) further includes an arrester (644). Arrester (644) has a plurality of detent tabs (646) configured to engage a detent catch (not shown) below lower wheel body (642) and fixed within housing (618). Cooperation between detent tabs (646) positioned on lower wheel body (640) and detent catch (not shown) further inhibits inadvertent clockwise or counterclockwise rotation of wheel ratchet (636). In the present example, "clockwise" and "counterclockwise" refer to rotation of wheel ratchet (636) as viewed from a top view of wheel ratchet (636).

Figure 28A:
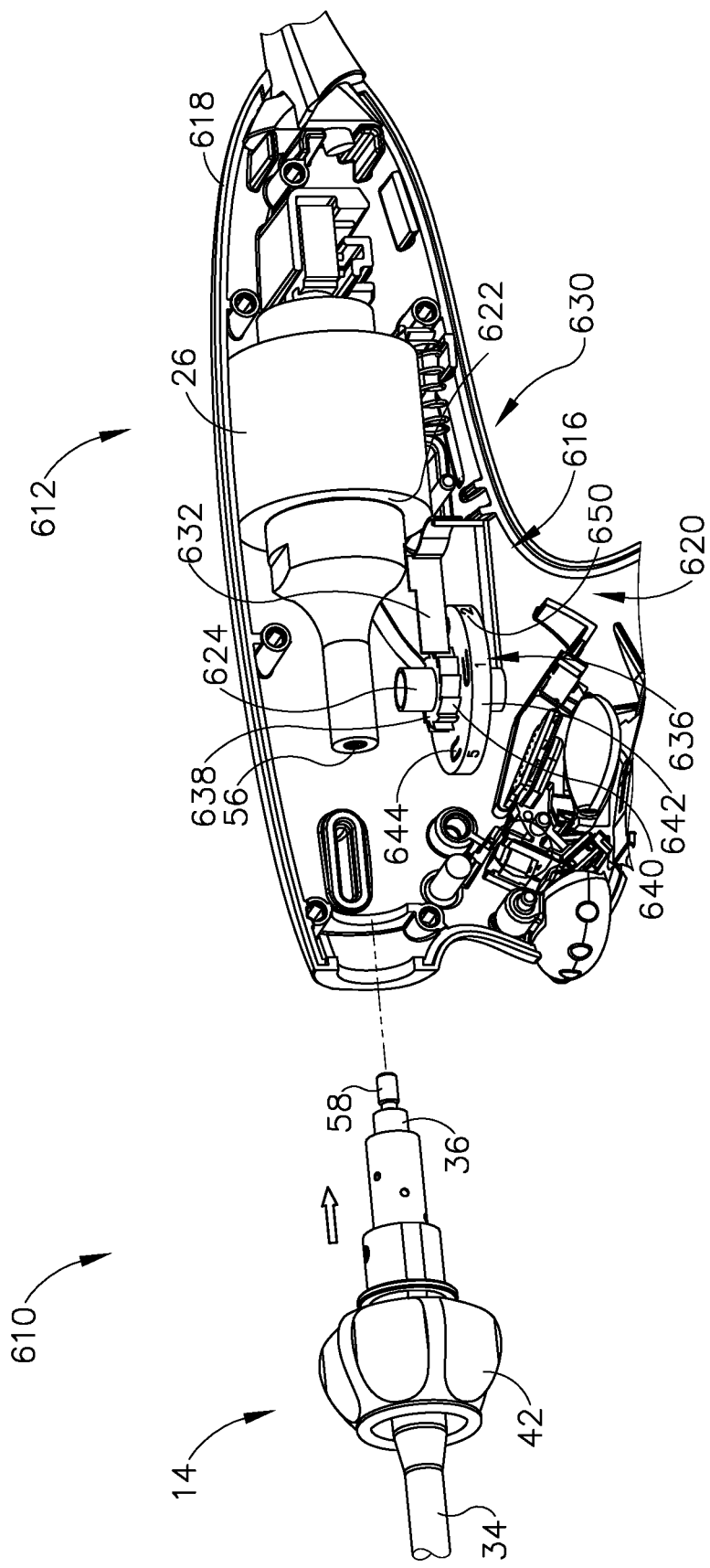
FIG. 28A depicts an enlarged perspective view of the ultrasonic surgical instrument and the fourth wheel ratchet usage indicator of FIG. 26 with the shaft assembly being inserted into the handle assembly, an ultrasonic transducer withdrawn to a proximal position, and various features hidden for clarity.
Figure 28B:
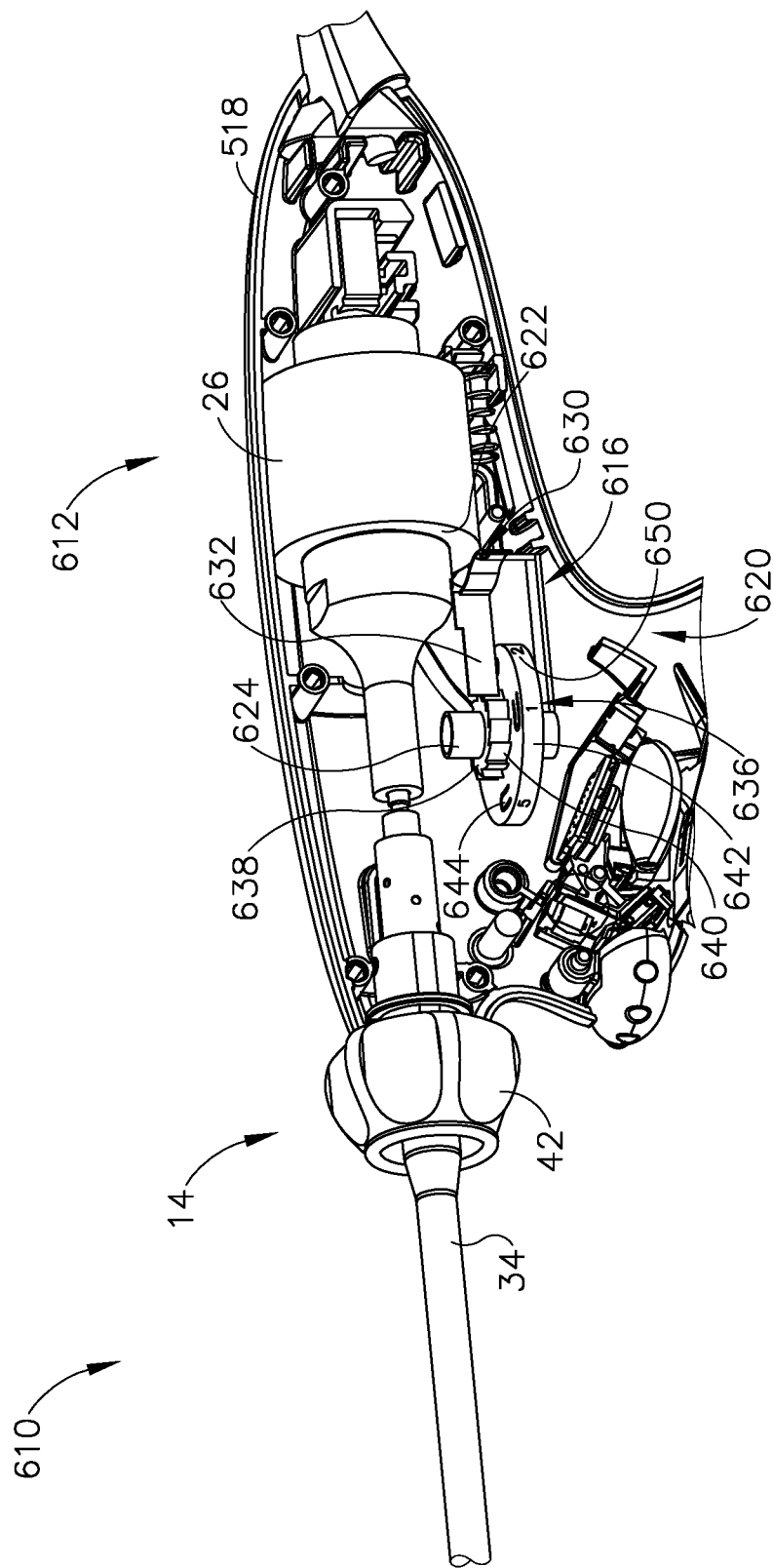
FIG. 28B depicts the enlarged perspective view of the ultrasonic surgical instrument and the fourth wheel ratchet usage indicator similar to FIG. 28A, but showing a waveguide being introduced into the ultrasonic transducer in the proximal position.
Figure 28C:
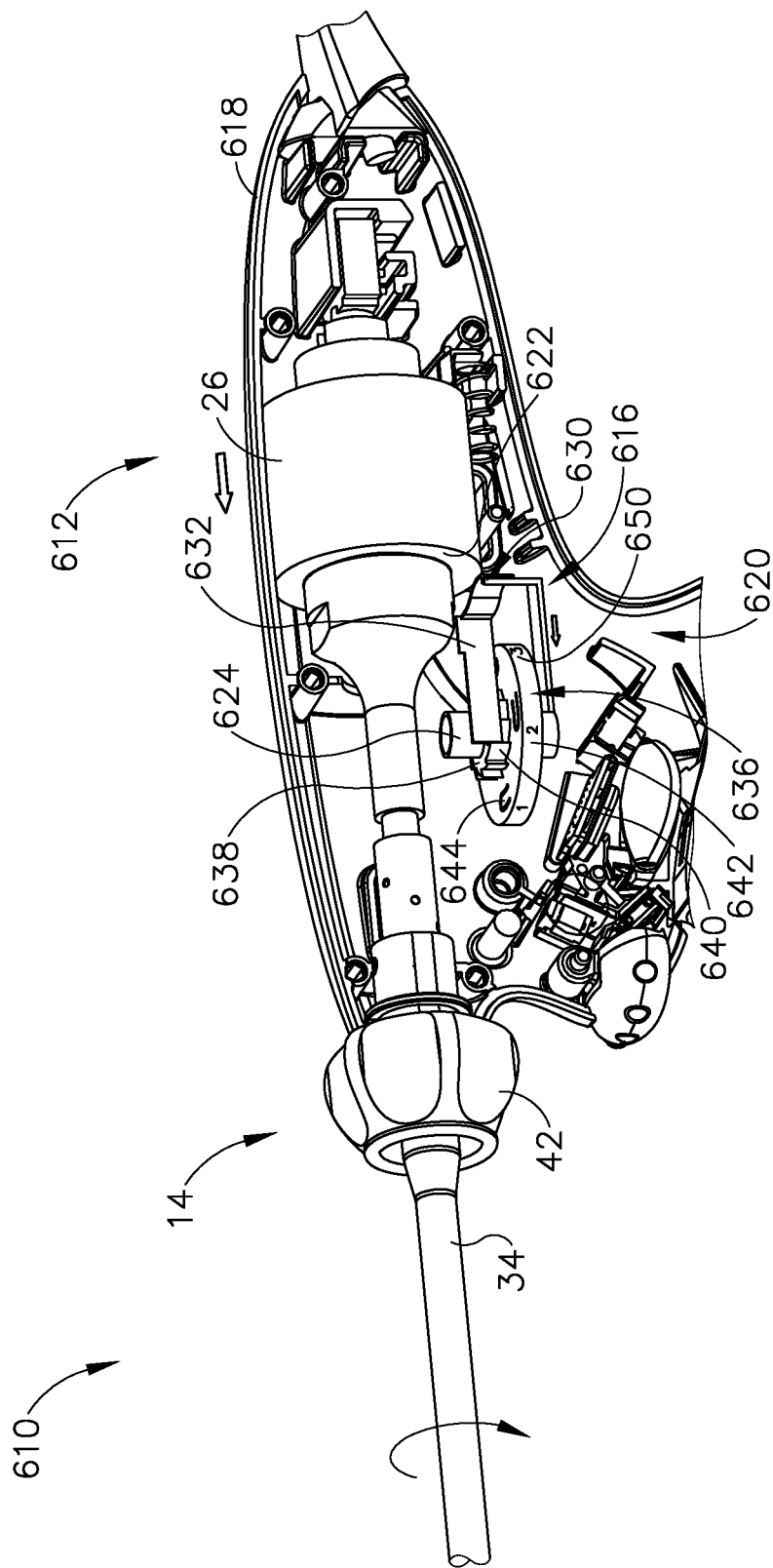
FIG. 28C depicts the enlarged perspective view of the ultrasonic surgical instrument and the fourth wheel ratchet usage indicator similar to FIG. 28B, but showing the waveguide being threadably coupled with the ultrasonic transducer thereby pulling the ultrasonic transducer distally from the proximal position toward a distal position and urging the fourth wheel ratchet usage indicator to indicate a second usage.

In the present example, with respect to FIG. 28A-28C, shaft assembly (14) mechanically and acoustically couples to handle assembly (612) by rotation similar to shaft and handle assemblies (114, 112) (see FIG. 7D). Threadably connecting waveguide (38) with ultrasonic transducer (26) distally pulls ultrasonic transducer (26) with actuator (622) into engagement with pawl tab (632) of ratchet mechanism (630). Pawl tab (632) in turn urges slip ratchet teeth (40) clockwise direction with sufficient force to overcome arrester (640). Disconnecting waveguide (38) from ultrasonic transducer (26) causes ultrasonic transducer (26) with actuator (622) to proximally return to the proximal position such that pawl tab (632) slips proximally along slip ratchet teeth (640). Arrester (640) is configured to secure wheel ratchet (636) such that pawl tab (632) slips without also rotating wheel ratchet (636) in the counterclockwise direction. Slip ratchet teeth (640) each include engagement and ramp portions (648a, 648b) to further aid to respective urging and slipping of wheel ratchet (636) similar to those discussed above in other examples herein.

Figure 26:
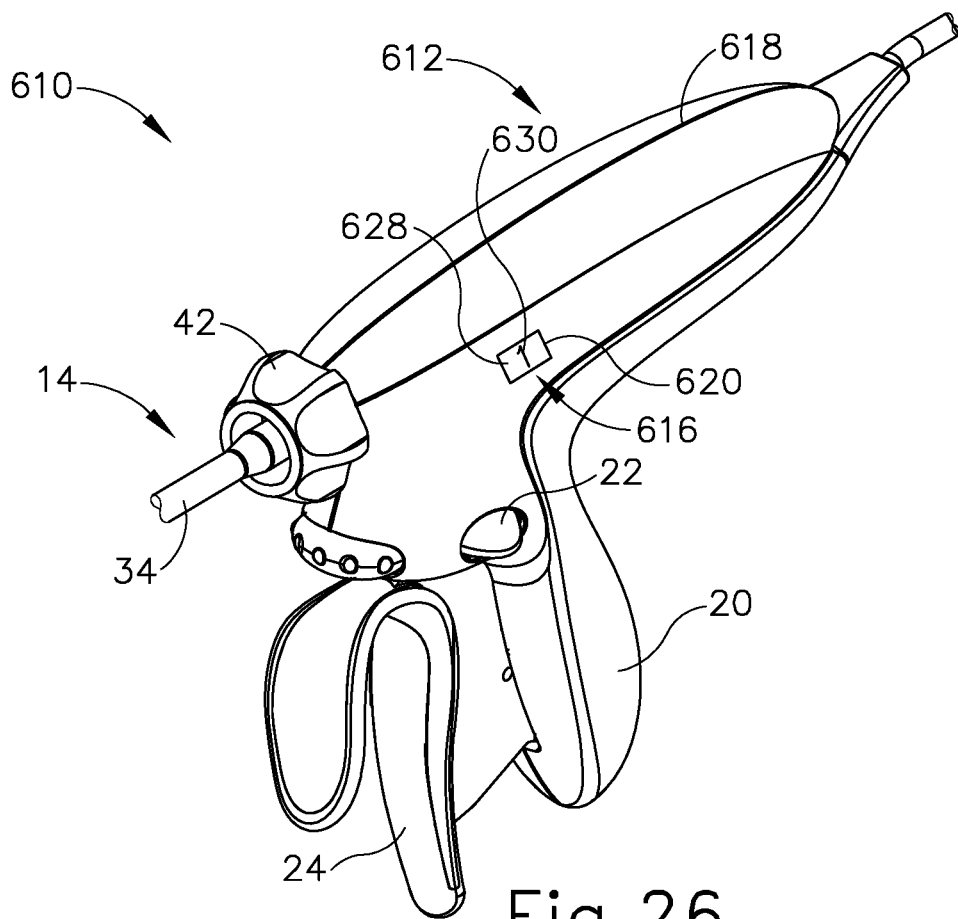
FIG. 26 depicts an enlarged perspective view of a seventh exemplary ultrasonic surgical instrument having a fourth wheel ratchet usage indicator for a shaft assembly and a handle assembly.
Figure 27:
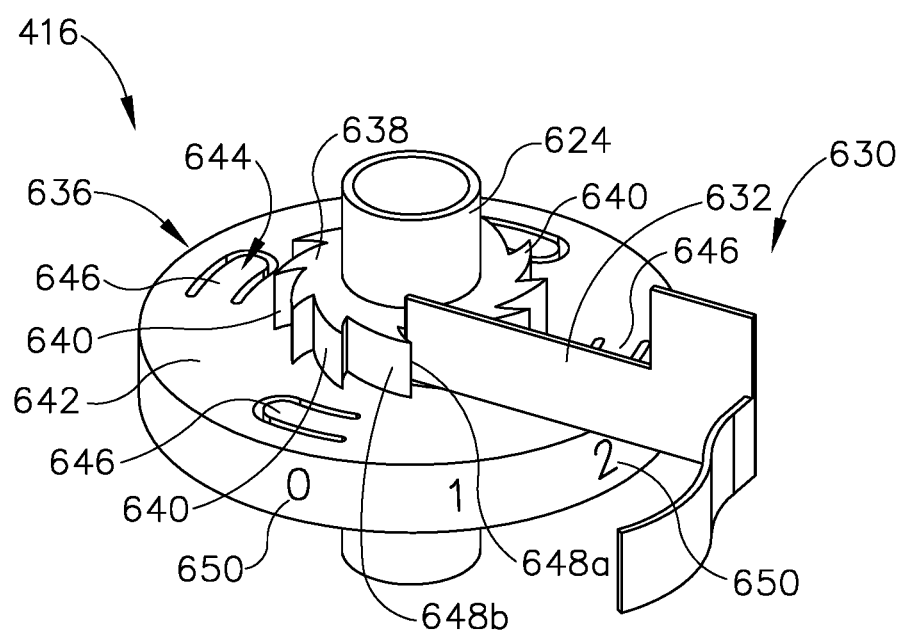
FIG. 27 depicts a perspective view of the fourth wheel ratchet usage indicator of FIG. 26.

As briefly discussed above, indicia window (628) (see FIG. 26) provides clinician with visual identification of the angular position of wheel ratchet (636). The relative angular position is recorded by a series of counter indices (650), which are angularly positioned about wheel ratchet (636) and increasing in the counterclockwise direction. The present example of counter indices (636) includes counterclockwise increasing numbers "1," "2," "3," "4," and "5" and are respectively configured to correspond to each replacement shaft assembly (14) used with handle assembly (612) in relation to the rotational position of wheel ratchet (636). For example, as shown in FIG. 26 and FIG. 28A, a first counter indicia (650) "1" transversely aligns through indicia window (628) to indicate to the clinician that handle assembly (612) is in its first use.

Successive connections of replacement shaft assemblies (14) continue to rotate wheel ratchet (636) until a fifth counter indicia (650) "5" transversely aligns through indicia window (628) to visually indicate the used state of handle assembly (612). In addition, fourth wheel ratchet usage indicator (616) is configured to mechanically inhibit further connection of replacement shaft assemblies (14) greater than the predetermined number of use cycles. More particularly, arrester (644) engages wheel ratchet (636) in the used state to inhibit further clockwise rotation thereof. Fourth wheel ratchet usage indicator (616) is thereby configured to inhibit inadvertently using handle assembly (612) beyond the predetermined number of use cycles.

In use, with respect to FIGS. 28A-28C, the clinician connects first replacement shaft assembly (14) to handle assembly (612) such that actuator (622) urges wheel ratchet (636) in alignment with the first indicia (650) for indicating the first use to clinician. Following treatment of the patient, shaft assembly (14) is disconnected from handle assembly (612) by slipping pawl tab (632) by ramp portions (648b) of slip ratchet teeth (640). Handle assembly (612) is then prepped, such as by heating and/or sterilizing, for another surgical procedure and another replacement shaft assembly (614) is connected to handle assembly (612). Actuator (622) of the second replacement shaft assembly (614) urges wheel ratchet (636) in alignment with the second indicia for indicating the second use to the clinician. Such reuse continues in the remaining use state until arrester (644) engages wheel ratchet (636) in the used state.

G. Fifth Wheel Ratchet Usage Indicator

FIGS. 29-31B illustrate an eighth exemplary ultrasonic surgical instrument (710) having a handle assembly (712) configured to be operated up to a predetermined number of use cycles, a shaft assembly (714) configured for a single use cycle of treatment, and a fifth wheel ratchet usage indicator (716). With respect to FIGS. 29-30, fifth wheel ratchet usage indicator (716) is integrated into a housing (718) of handle assembly (712) for recording and indicating each respective use cycle of handle assembly (712) in a use remaining state to a used state. Fifth wheel ratchet usage indicator (716) has a housing portion (720) that cooperates with shaft assembly (714) upon connection of shaft assembly (714) to handle assembly (712) to thereby direct fifth wheel ratchet usage indicator (716) toward the used state with each replacement shaft assembly (714). Once shaft assembly (714) has been replaced the predetermined number of use cycles, fifth wheel ratchet usage indicator (716) indicates the used state of handle assembly (712) to the clinician. Such indication of fifth wheel ratchet usage indicator (716) is visual as well as a lockout, which inhibits operation of handle assembly (712).

Shaft assembly (714) has outer tube (34) with a distal end actuator (722), whereas housing portion (720) of fifth wheel ratchet usage indicator (716) includes, an indicia window (728) through housing (718), a rotatable wheel mount (724), a ratchet mechanism (730), and a wheel ratchet (736). Wheel ratchet (736) is rotatably mounted to wheel mount (724) within housing (718), whereas ratchet mechanism (730) is translatably mounted within housing (718) and biased in the distal direction toward distal end actuator (722) of outer tube (34). In the present example, insertion of outer tube (34) into housing (718) causes distal end actuator (722) to proximally urge ratchet mechanism (730) into engagement with wheel ratchet (736) for rotating wheel ratchet (736) while wheel ratchet (736) is visible to clinician through indicia window (728) as discussed below in greater detail.

In the present example, ratchet mechanism (730) includes a translatable member (731), a pivotal pawl (732) connected to a distal end portion of translatable member (731), and a biasing member, such as a tension spring (734). Tension spring (734) biases translatable member (731) with pivotal pawl (732) carried thereon in the distal direction for engagement with distal end actuator (722) of outer tube (34). Thus, pivotal pawl (732) is configured to be proximally translated by distal end actuator (722) outer tube (34) slides into housing (718).

Wheel ratchet (736) is generally cylindrical and has a plurality of radially projecting slip ratchet teeth (740) about rotatable wheel mount (724). Pivotal pawl (732) is thus configured to engage slip ratchet teeth (740) while moving the proximal direction and urge wheel ratchet (736) in the clockwise direction, but inhibit movement in the counterclockwise direction. In addition, fifth wheel ratchet usage indicator (716) further includes an arrester (744). Arrester (744) has a resiliently mounted arrester pawl (746) and a brake member (747) configured to engage slip ratchet teeth (740) and collectively inhibit inadvertent counterclockwise rotation of wheel ratchet (636). More particularly, arrester pawl (746) inhibits counterclockwise rotation of wheel ratchet (736) by engagement with slip ratchet teeth (740), but slips along slip ratchet teeth (740) during clockwise rotation. Brake member (747) generally frictionally engages wheel ratchet (736) to inhibit inadvertent clockwise and counterclockwise rotation and is further configured to lock movement of wheel ratchet (736) in the used state. In the present example, "clockwise" and "counterclockwise" refer to rotation of wheel ratchet (736) as viewed from a side view of wheel ratchet (736) in FIGS. 30-31B.

Figure 31A:
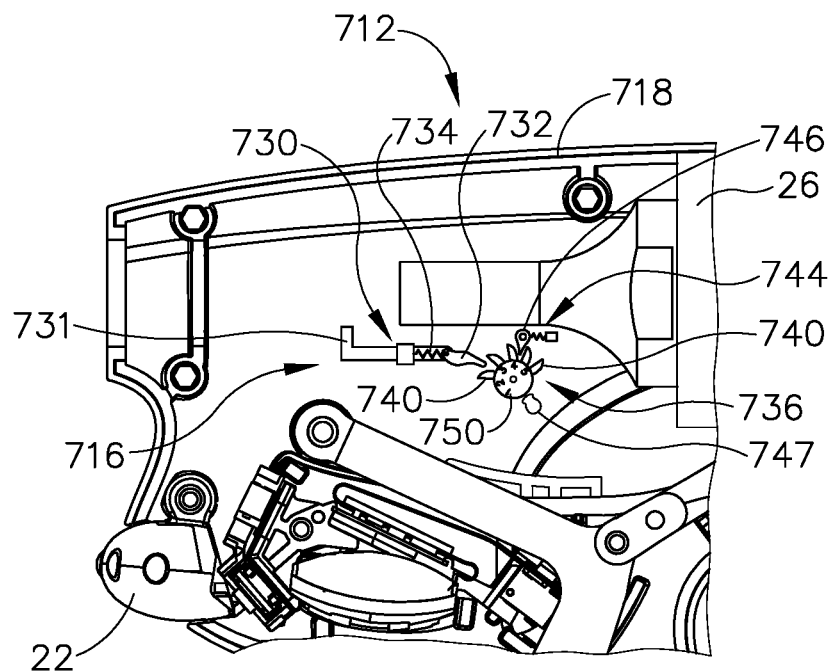
FIG. 31A depicts an enlarged side view of the ultrasonic surgical instrument and the fifth wheel ratchet usage indicator of FIG. 29 having various features hidden for more clearly showing the fifth wheel ratchet usage indicator within the handle assembly.
Figure 31B:
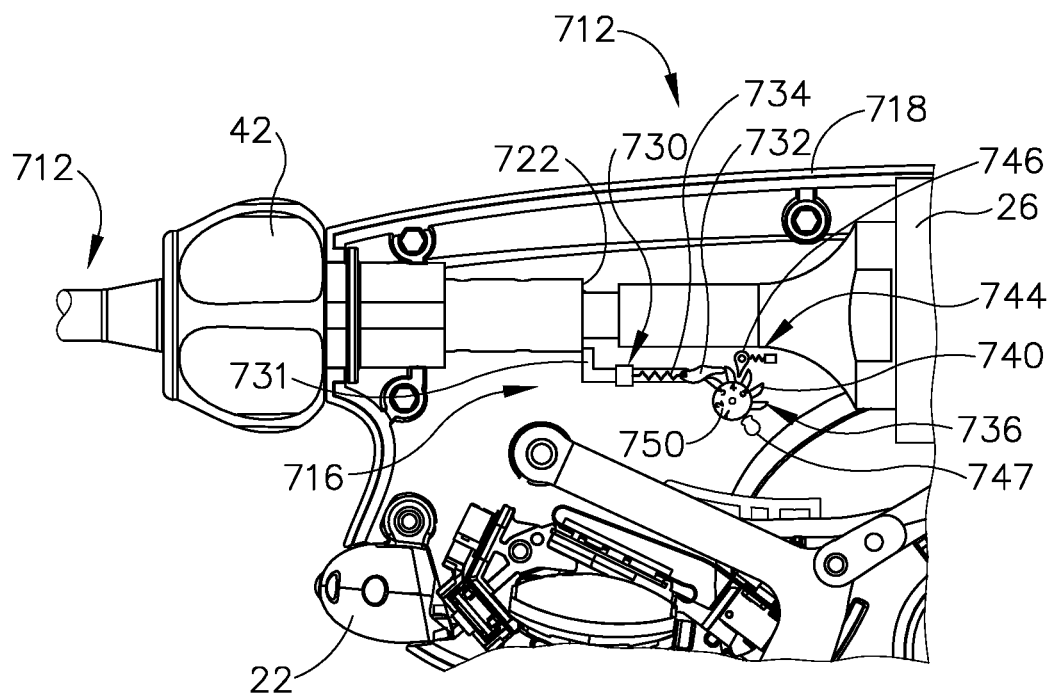
FIG. 31B depicts the enlarged side view of the ultrasonic surgical instrument and the fifth wheel ratchet usage indicator similar to FIG. 31A, but showing the shaft assembly connected to the handle assembly and urging the fifth wheel ratchet usage indicator to indicate a second usage.
Figure 32A:
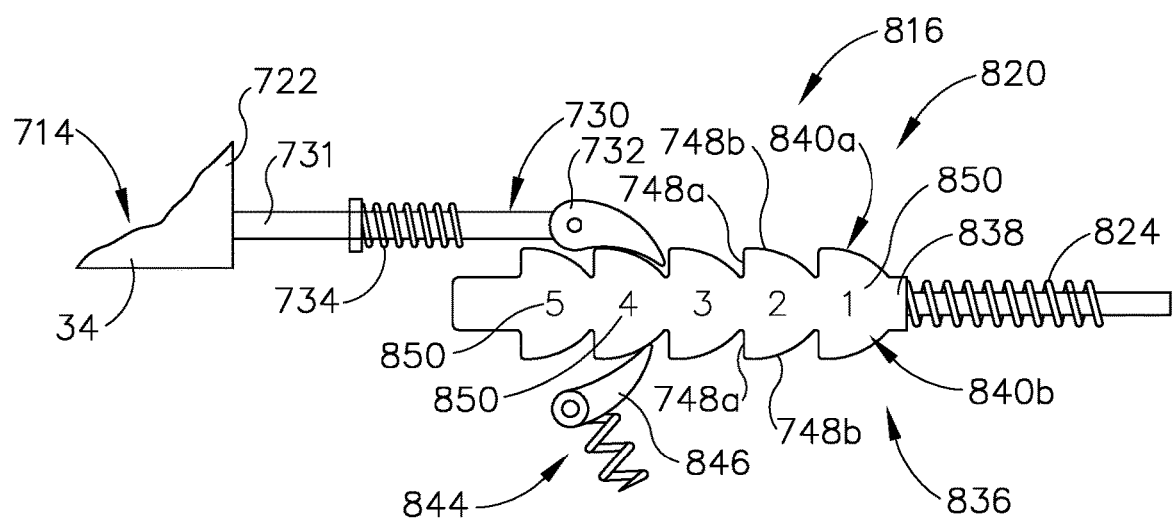
FIG. 32A depicts a side view of a linear ratchet usage indicator having a ratchet mechanism and a linear ratchet indicating a third usage with a shaft assembly.
Figure 32B:
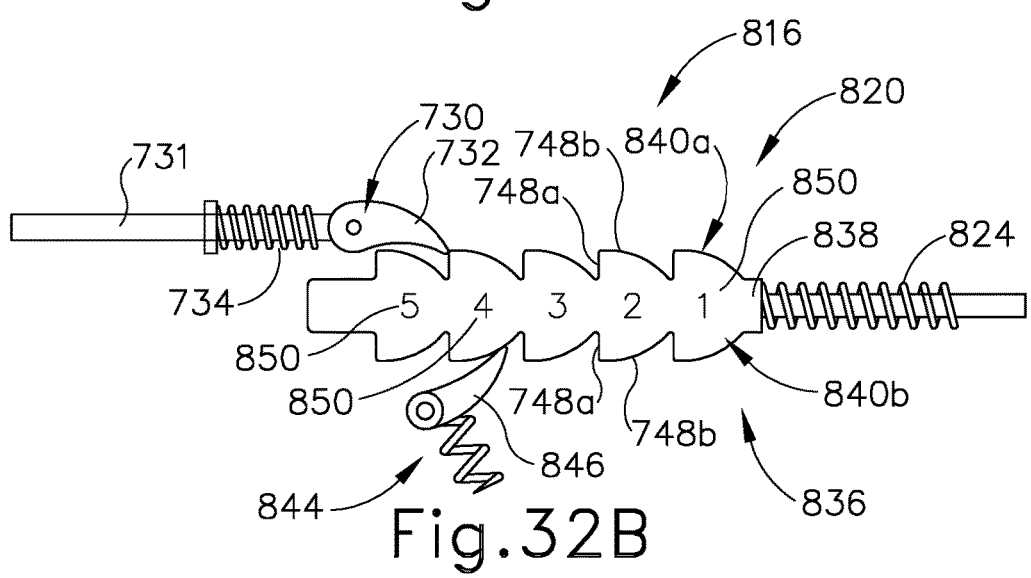
FIG. 32B depicts the side view of the linear ratchet usage indicator similar to FIG. 32A, but showing the ratchet mechanism biased to a distal position upon removal of the shaft assembly.
Figure 32C:
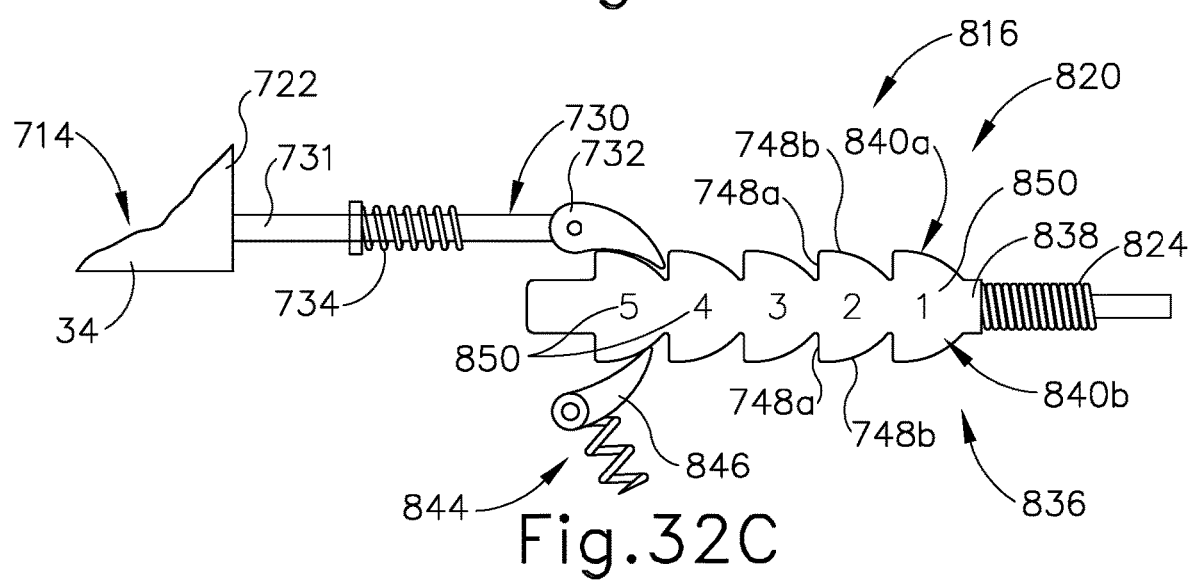
FIG. 32C depicts the side view of the linear ratchet usage indicator similar to FIG. 32B, but showing the ratchet mechanism being urged proximally to a proximal position by the shaft assembly to thereby urge the linear ratchet to indicate a fourth usage with the shaft assembly.

In the present example, with respect to FIG. 31A-31B, shaft assembly (714) mechanically and acoustically couples to handle assembly (712) by rotation similar to shaft and handle assemblies (114, 112) (see FIG. 7D). Insertion of outer tube (34) into housing (718) causes distal end actuator (722) to engage translatable member (731) and collectively slide translatable member (731) and pivotal pawl (732) in the proximal direction toward wheel ratchet (740). Pivotal pawl (732) pivots to effectively ride along slip ratchet teeth (740) and accommodate rotation of slip ratchet teeth (740) while maintaining engagement therewith. Pivotal pawl (732) in turn urges slip ratchet teeth (740) in the clockwise direction with sufficient force to overcome arrester (740). Disconnecting shaft assembly (714) from handle assembly (712) causes with distal end actuator (722) to proximally disengage from translatable member (731). Translatable member (731) and pivotal pawl (732) thereby return to the distal position such that pivotal pawl (732) slips distally along slip ratchet teeth (740). Arrester (740) is configured to secure wheel ratchet (736) such that pivotal pawl (732) slips without also rotating wheel ratchet (736) in the counterclockwise direction. Slip ratchet teeth (740) and arrester pawl (746) each include engagement and ramp portions (748a, 748b) to further aid to respective urging and slipping of wheel ratchet (736) similar to those discussed above in other examples herein.

Figure 29:
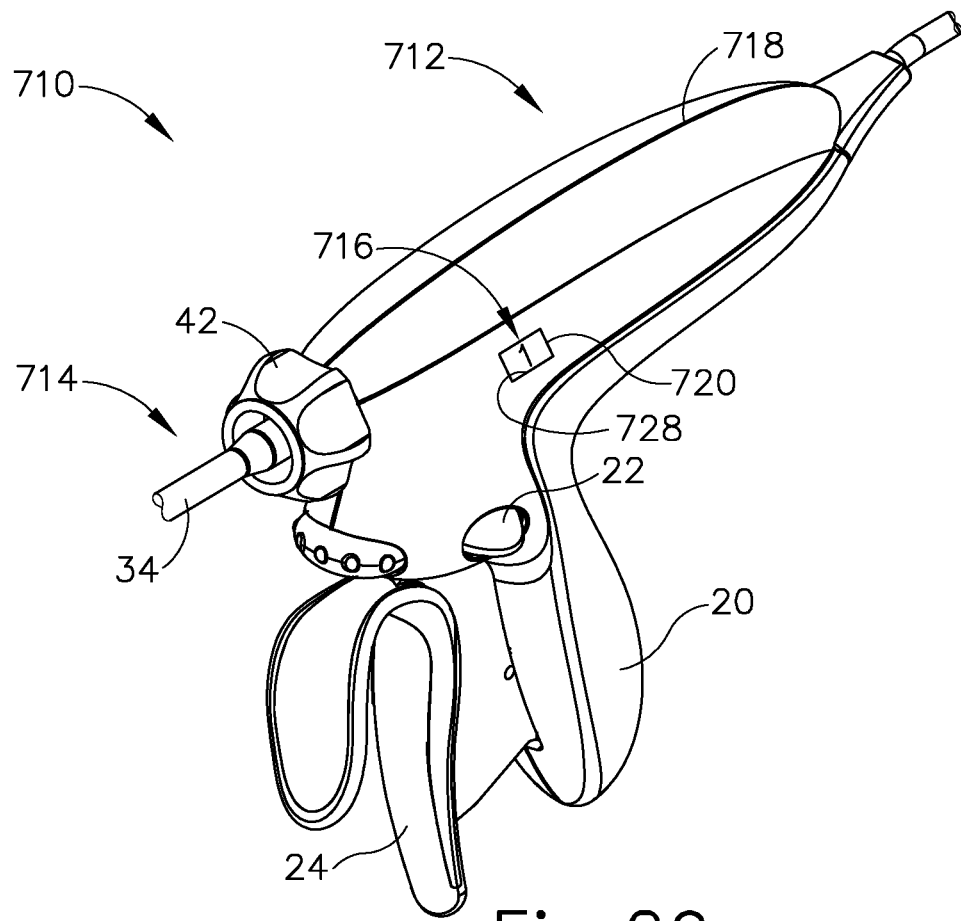
FIG. 29 depicts an enlarged perspective view of an eighth exemplary ultrasonic surgical instrument having a fifth wheel ratchet usage indicator for a shaft assembly and a handle assembly.
Figure 30:
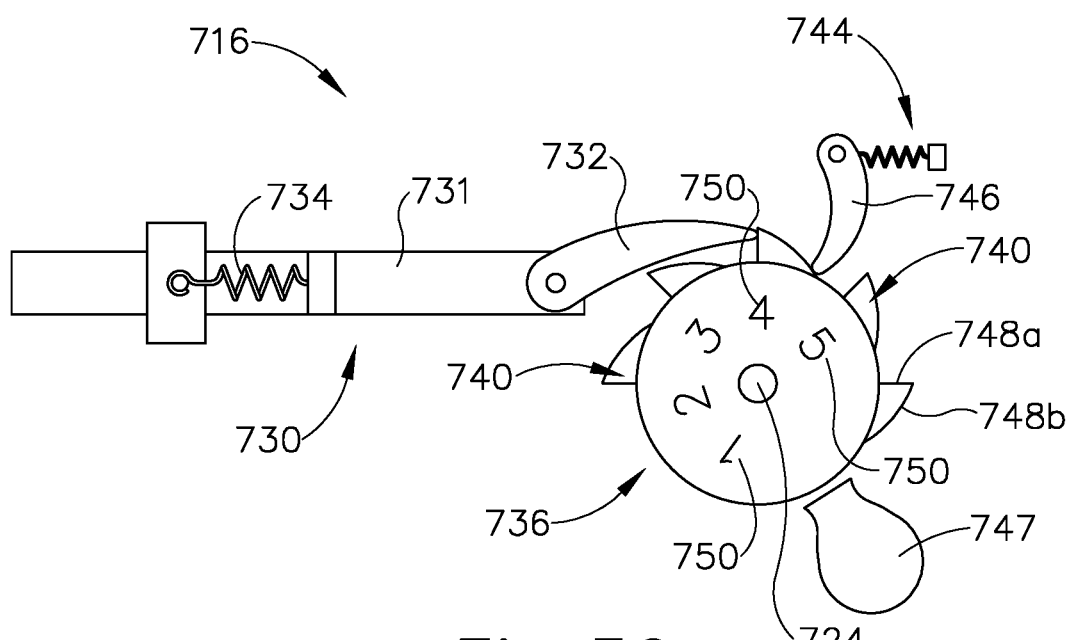
FIG. 30 depicts a side view of the fifth wheel ratchet usage indicator of FIG. 29.

As briefly discussed above, indicia window (728) (see FIG. 29) provides clinician with visual identification of the angular position of wheel ratchet (736). The relative angular position is recorded by a series of counter indices (750), which are angularly positioned about wheel ratchet (736) and increasing in the clockwise direction. The present example of counter indices (736) includes clockwise increasing numbers "1," "2," "3," "4," and "5" and are respectively configured to correspond to each replacement shaft assembly (714) used with handle assembly (712) in relation to the rotational position of wheel ratchet (736). In the present example, such correspondence indicates the amount of use cycles remaining and thus, progressively decreases with use. For example, as shown in FIG. 29, a first counter indicia (750) "1" aligns through indicia window (728) to indicate to the clinician that handle assembly (712) has one use remaining. Alternatively, counter indices (736) may be counterclockwise increasing numbers in order to indicate the cumulative use cycles of handle assembly (712).

The invention is thus not intended to be unnecessarily limited to increasing or decreasing numerical indices for the present example or other examples described herein.

Successive connections of replacement shaft assemblies (714) continue to rotate wheel ratchet (736) until a fifth counter indicia (750) "5" aligns through indicia window (728) to visually indicate the used state of handle assembly (712) as shown in FIGS. 31A-31B. In addition, fifth wheel ratchet usage indicator (716) is configured to mechanically inhibit further connection of replacement shaft assemblies (714) greater than the predetermined number of use cycles. More particularly, brake member (748) of arrester (744) engages wheel ratchet (736) in the used state to inhibit further clockwise rotation thereof. Fifth wheel ratchet usage indicator (716) is thereby configured to inhibit inadvertently using handle assembly (712) beyond the predetermined number of use cycles.

In use, with respect to FIGS. 31A-31B, the clinician connects first replacement shaft assembly (714) to handle assembly (712) such that actuator (722) urges wheel ratchet (736) in alignment with the first indicia (750) for indicating the first use to clinician. Following treatment of the patient, shaft assembly (714) is disconnected from handle assembly (712) by slipping pivotal pawl (732) by ramp portions (748b) of slip ratchet teeth (740). Handle assembly (712) is then prepped, such as by heating and/or sterilizing, for another surgical procedure and another replacement shaft assembly (714) is connected to handle assembly (712). Distal end actuator (722) of the second replacement shaft assembly (714) urges wheel ratchet (736) in alignment with the second indicia for indicating the second use to the clinician. Such reuse continues in the remaining use state until arrester (744) engages wheel ratchet (736) in the used state.

H. Linear Ratchet Usage Indicator

FIGS. 32A-33C illustrate a linear ratchet usage indicator (816) for use with handle assembly (712) and shaft assembly (714) shown in FIG. 29. Similar to fifth wheel ratchet usage indicator (716) discussed above, linear ratchet usage indicator (816) is integrated into housing (718) of handle assembly (712) for recording and indicating each respective use cycle of handle assembly (712) in a use remaining state to a used state. Linear ratchet usage indicator (816) has a housing portion (820) that cooperates with shaft assembly (714) upon connection of shaft assembly (714) to handle assembly (712) to thereby direct linear ratchet usage indicator (816) toward the used state with each replacement shaft assembly (714). Once shaft assembly (714) has been replaced the predetermined number of use cycles, linear ratchet usage indicator (816) indicates the used state of handle assembly (712) to the clinician. Such indication of linear ratchet usage indicator (816) is visual as well as a lockout, which inhibits operation of handle assembly (712).

Shaft assembly (714) has outer tube (34) with distal end actuator (722), whereas housing portion (820) of linear ratchet usage indicator (816) includes ratchet mechanism (730) as discussed above as well as a linear mount (824) and a linear ratchet (736). Linear ratchet (736) is translatably mounted to linear mount (824) and biased in the distal direction toward ratchet mechanism (730). In the present example, insertion of outer tube (34) into housing (718) causes distal end actuator (722) to proximally urge ratchet mechanism (730) into engagement with linear ratchet (836) for proximally translating linear ratchet (836) while linear ratchet (836) is visible to clinician through indicia window (728) as discussed below in greater detail.

Linear ratchet (836) generally includes an elongate plate body (838) having a series of upper and lower transversely projecting slip ratchet teeth (840a, 840b). Upper and lower slip ratchet teeth (840a, 840b) are respectively linearly aligned and extending upward and downward from elongate plate body (838). Pivotal pawl (732) is thus configured to engage upper slip ratchet teeth (840) while moving in the proximal direction and urge linear ratchet (836) in the proximal direction, but inhibit movement in the distal direction. In addition, linear ratchet usage indicator (816) further includes an arrester (844). Arrester (844) has a resiliently mounted arrester pawl (846) configured to engage lower slip ratchet teeth (840b) to inhibit inadvertent distal movement of linear ratchet (836). While not shown in the present example, arrester (844) may further include a brake member (not shown) similar to brake member (747) (see FIG. 30) discussed above for further inhibiting inadvertent proximal and distal movement of linear ratchet (836).

As briefly discussed above, indicia window (728) (see FIG. 29) provides clinician with visual identification of the longitudinal position of linear ratchet (836). The relative longitudinal position is recorded by a series of counter indices (850), which are longitudinally positioned along linear ratchet (836) and increasing in the counterclockwise direction. The present example of counter indices (736) includes distally increasing numbers "1," "2," "3," "4," and "5" and are respectively configured to correspond to each replacement shaft assembly (714).

Successive connections of replacement shaft assemblies (714) continue to proximally translate linear ratchet (836) until a fifth counter indicia (850) "5" aligns through indicia window (728). In addition, linear ratchet usage indicator (816) is configured to mechanically inhibit further connection of replacement shaft assemblies (814) greater than the predetermined number of use cycles. More particularly, linear ratchet (836) is configured to cease further proximal translation in the used state to thereby inhibit inadvertently using handle assembly (712) (see FIG. 29) beyond the predetermined number of use cycles.

In use, with respect to FIGS. 29 and 32A-32C, the clinician connects first replacement shaft assembly (714) to handle assembly (712) such that actuator (722) urges linear ratchet (836) in alignment with the first indicia (850) for indicating the first use to clinician. Following treatment of the patient, shaft assembly (714) is disconnected from handle assembly (712) by slipping pivotal pawl (732) by ramp portions (748b) of slip ratchet teeth (840a). Handle assembly (712) is then prepped, such as by heating and/or sterilizing, for another surgical procedure and another replacement shaft assembly (714) is connected to handle assembly (712). Distal end actuator (722) of the second replacement shaft assembly (714) urges linear ratchet (836) in alignment with the second indicia for indicating the second use to the clinician. Such reuse continues in the remaining use state until linear ratchet (836) translates proximally to the used state to inhibit further attachment of additional replacement shaft assemblies (714).

I. Slip Ratchet Usage Indicator

FIGS. 33-35E illustrate a ninth exemplary ultrasonic surgical instrument (910) having a handle assembly (912) configured to be operated up to a predetermined number of use cycles, a shaft assembly (914) configured for a single use cycle of treatment, and a slip ratchet usage indicator (916). With respect to FIGS. 33-34, slip ratchet usage indicator (916) is integrated into portions of shaft assembly (914) and a housing (918) of handle assembly (912) for recording and indicating each respective use cycle of handle assembly (912) in a use remaining state to a used state. Slip ratchet usage indicator (916) has a shaft portion (919) that cooperates with a housing portion (920) upon connection of shaft assembly (914) to handle assembly (912) to thereby direct slip ratchet usage indicator (916) toward the used state with each replacement shaft assembly (914). Once shaft assembly (914) has been replaced the predetermined number of use cycles, slip ratchet usage indicator (916) indicates the used state of handle assembly (912) to the clinician. Such indication of slip ratchet usage indicator (916) is visual as well as a lockout, which inhibits operation of handle assembly (912).

Figure 34:
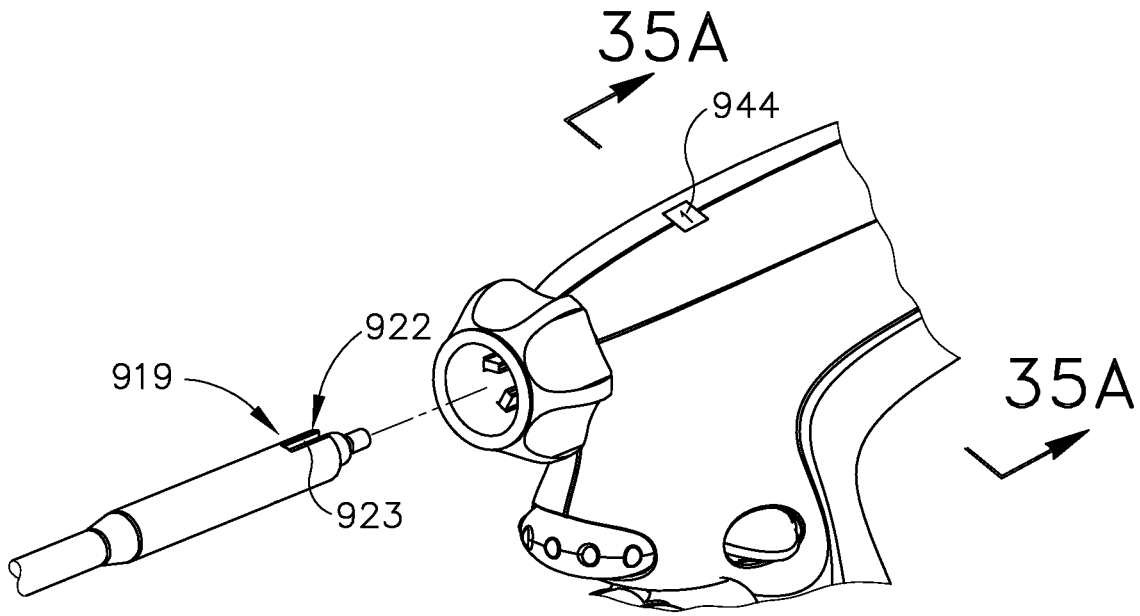
FIG. 34 depicts an enlarged, partially exploded perspective view of the ultrasonic surgical instrument and the slip ratchet usage indicator of FIG. 33.
Figure 35A:
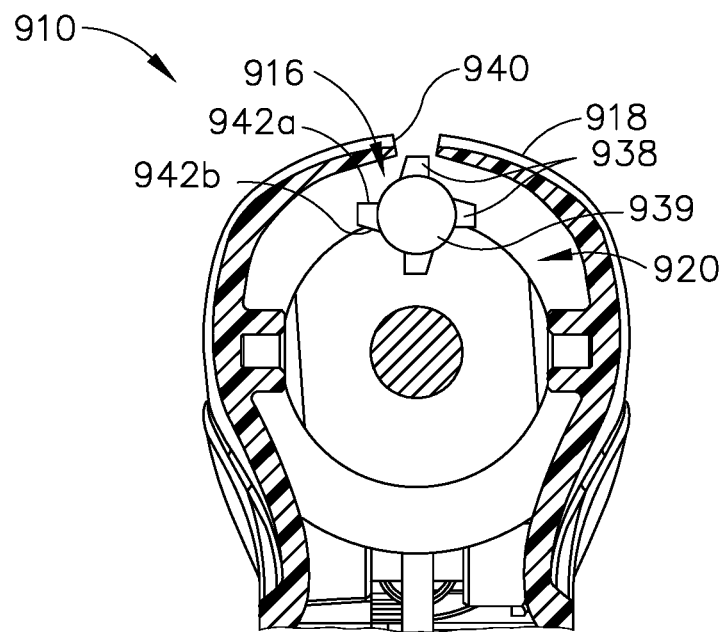
FIG. 35A depicts a cross-sectional view of the ultrasonic surgical instrument and the slip ratchet usage indicator taken along section line 35A-35A of FIG. 34 with the shaft assembly removed from the handle assembly and the slip ratchet usage indicator indicating a first usage.

As shown in FIGS. 34-35A, shaft portion (919) of slip ratchet usage indicator (916) includes an actuator (922) positioned on outer tube (34). Actuator (34) of the present example includes a receiving slot (923) and a follower slot (924). Housing portion (920) of slip ratchet usage indicator (916) includes a wheel ratchet (936) having a plurality of slip ratchet teeth (938) angularly positioned about and extending radially outward from a rotatable shaft (939). Wheel ratchet (936) is ratcheted to rotate in a clockwise direction, but not rotate in the counterclockwise direction. Wheel ratchet (936) is thus configured to indicate usage through an indicia window (940) extending through an upper surface of housing (918) as discussed below in greater detail. In addition, wheel ratchet (936) further includes an arrester (not shown) to inhibit inadvertent clockwise or counterclockwise rotation. In the present example, "clockwise" and "counterclockwise" refer to rotation of wheel ratchet (936) as viewed from a distal end of wheel ratchet (936).

Figure 35B:
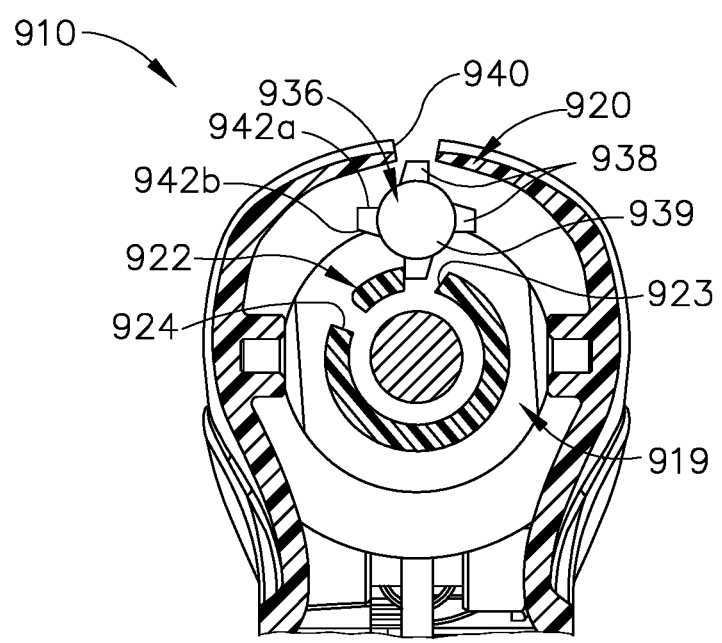
FIG. 35B depicts the cross-sectional view of the ultrasonic surgical instrument and the slip ratchet usage indicator similar to FIG. 35A, but showing the shaft assembly inserted into the handle assembly in an unlocked state.
Figure 35C:
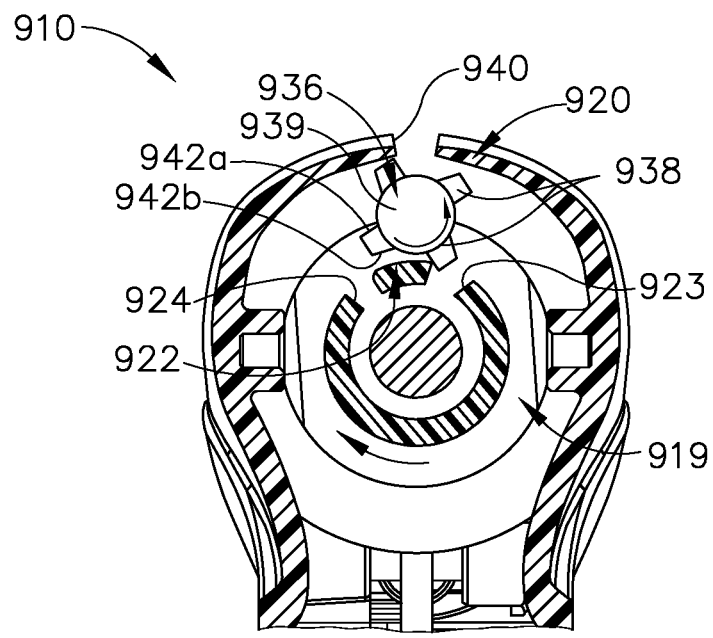
FIG. 35C depicts the cross-sectional view of the ultrasonic surgical instrument and the slip ratchet usage indicator similar to FIG. 35B, but showing the shaft assembly being rotated from the unlocked state toward the locked state to thereby rotate the slip ratchet usage indicator.
Figure 35D:
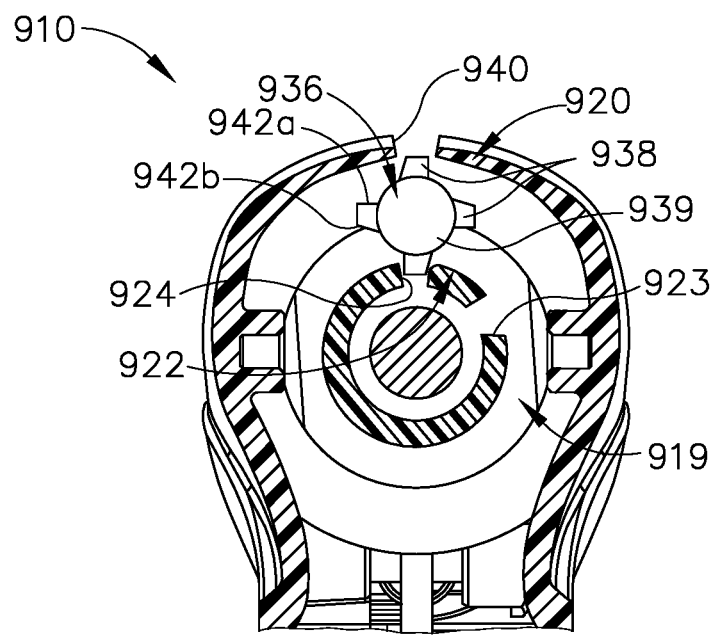
FIG. 35D depicts the cross-sectional view of the ultrasonic surgical instrument and the slip ratchet usage indicator similar to FIG. 35C, but showing the shaft assembly in the locked state and the slip ratchet usage indicator indicating a second usage.

In the present example, shaft assembly (914) mechanically and acoustically couples to handle assembly (912) by rotation similar to shaft and handle assemblies (114, 112) (see FIG. 7D). As outer tube (34) is inserted into housing (918) as shown in FIGS. 35A-35B, receiving slot (923) in outer tube (34) translatably receives a lower slip ratchet tooth (938). Rotating outer tube (34) for connection to shaft assembly (914) in the clockwise direction causes actuator (922) to similarly rotate wheel ratchet (936) in the counterclockwise direction. Follower slot (924) then radially receives an adjacent slip ratchet tooth (938) as shown in FIGS. 35C-35D, at which point outer tube (34) is mechanically coupled with handle assembly (912).

Figure 35E:
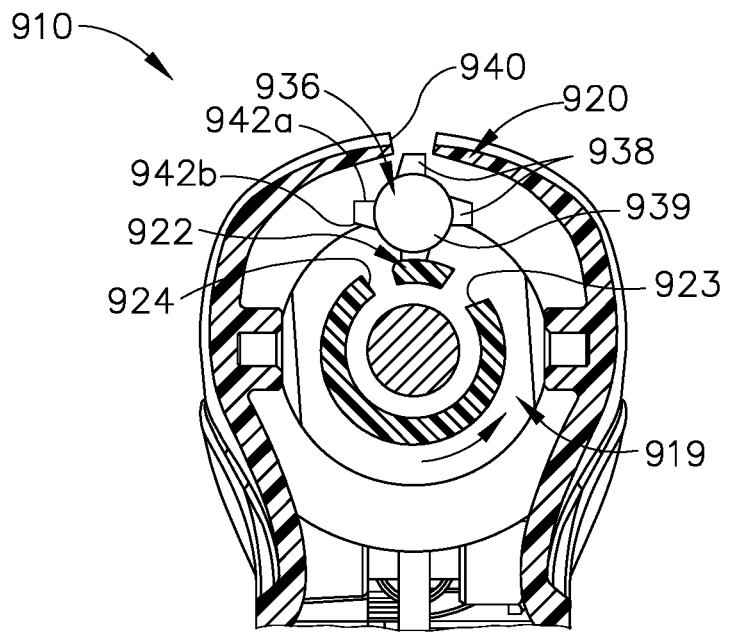
FIG. 35E depicts the cross-sectional view of the ultrasonic surgical instrument and the slip ratchet usage indicator similar to FIG. 35D, but showing the shaft assembly being rotated from the locked state toward the unlocked state for removal after use and the slip ratchet usage indicator indicating the second usage.

Upon removal of shaft assembly (914), outer tube (34) is rotated counterclockwise as shown in FIG. 35E. However, because wheel ratchet (936) is ratcheted as discussed above, wheel ratchet (936) does not rotate clockwise upon engaged with actuator (922) with slip ratchet tooth (938) in follower slot (924). Instead, outer tube (34) compresses slip ratchet tooth (938) and slips counterclockwise along slip ratchet tooth (938) until slip ratchet tooth (938) is again radially received back in receiving slot (923) for removal of outer tube (34) from handle assembly (912). Such urging and slipping of wheel ratchet (936) is further aided by engagement and ramp portions (942a, 942b) of slip ratchet teeth (938) similar to those discussed above in other examples herein. The angular position of wheel ratchet (936) is thus configured to indicate to the clinician the use remaining state as it is rotated in the counterclockwise direction toward the used state by successive connections of replacement shaft assemblies (914).

Figure 33:
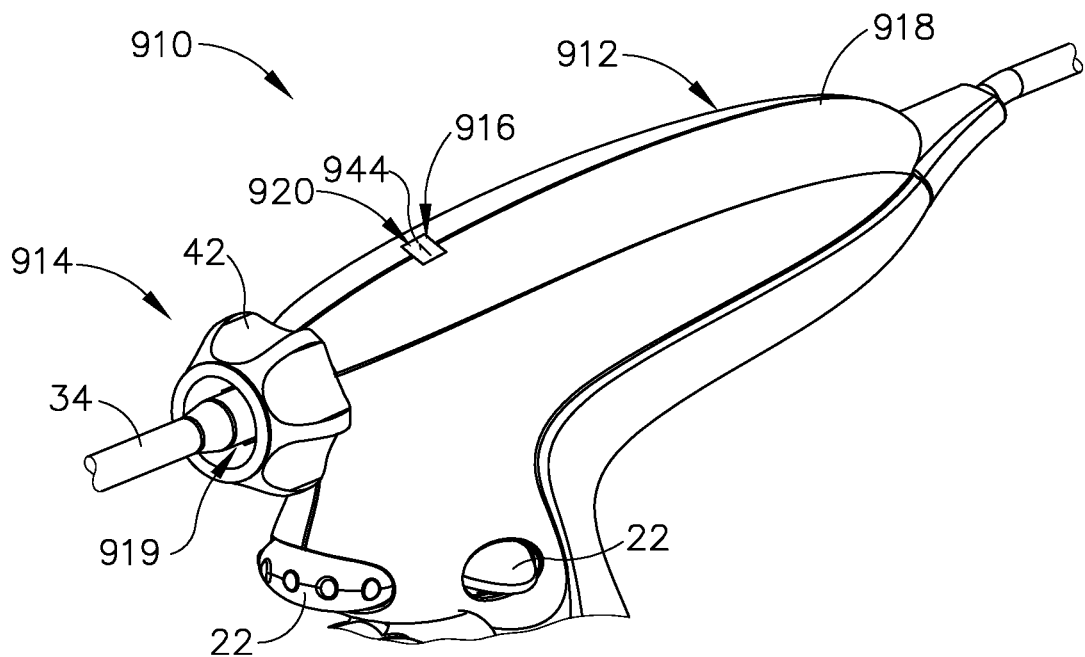
FIG. 33 depicts an enlarged perspective view of a ninth exemplary ultrasonic surgical instrument having a slip ratchet usage indicator for a shaft assembly and a handle assembly.

As briefly discussed above, indicia window (940) provides clinician with visual identification of the angular position of wheel ratchet (936). The relative angular position is recorded by a series of counter indices (944), which are angularly positioned about wheel ratchet (936) and increasing in the counterclockwise direction. The present example of counter indices (944) includes clockwise increasing numbers "1," "2," "3," and "4," and are respectively configured to correspond to each replacement shaft assembly (914) used with handle assembly (912) in relation to the rotational position of wheel ratchet (936). For example, as shown in FIGS. 33-34, a first counter indicia (944) "1" transversely aligns through indicia window (940) to indicate to the clinician that handle assembly (912) is in its first use.

Successive connections of replacement shaft assemblies (914) continue to rotate wheel ratchet (936) until a fourth counter indicia (944) "4" transversely aligns through indicia window (440) to visually indicate the used state of handle assembly (912). In addition, slip ratchet usage indicator (916) may further include arrester (not shown) to mechanically inhibit further connection of replacement shaft assemblies (914) greater than the predetermined number of use cycles. Slip ratchet usage indicator (916) is thereby configured to inhibit inadvertently using handle assembly (912) beyond the predetermined number of use cycles.

In use, with respect to FIGS. 35A-35E, the clinician connects first replacement shaft assembly (914) to handle assembly (912) such that actuator (2222) urges wheel ratchet (936) counterclockwise in alignment with the first indicia (944) for indicating the first use to clinician. Following treatment of the patient, shaft assembly (914) is disconnected from handle assembly (912) while ratcheted wheel ratchet (936) remains stationary relative to outer tube (34). Handle assembly (912) is then prepped, such as by heating and/or sterilizing, for another surgical procedure and another replacement shaft assembly (914) is connected to handle assembly (912). Actuator (926) of the second replacement shaft assembly (914) urges wheel ratchet (936) in alignment with the second indicia for indicating the second use to the clinician. Such reuse continues in the remaining use state until wheel ratchet (936) rotates counterclockwise to the used state to inhibit further attachment of additional replacement shaft assemblies (914).

J. Cycle Response Usage Indicator

FIGS. 36-40B illustrate a tenth exemplary ultrasonic surgical instrument (1010) having a handle assembly (1012) configured to be operated up to a predetermined number of use cycles, shaft assembly (14) configured for a single use cycle of treatment, and a cycle response usage indicator (1016). With respect to FIGS. 36-39, cycle response usage indicator (1016) is integrated into a housing (1018) of handle assembly (1012) for recording and indicating each respective use cycle of handle assembly (1012) in a use remaining state to a used state. Cycle response usage indicator (1016) has a housing portion (1020) is configured to respond to a state of use that occurs once per usage cycle to thereby direct cycle response usage indicator (1016) toward the used state. In the present example, cycle response usage indicator (1016) is directed toward the used state each time cycle response usage indicator (1016) is increased in temperature to a predetermined cleaning temperature. Once handle assembly (1012) has been repeatedly heated to the predetermined cleaning temperature the predetermined number of use cycles, cycle response usage indicator (1016) indicates the used state of handle assembly (1012) to the clinician. Such indication of cycle response usage indicator (1016) is visual as well as a lockout, which inhibits operation of handle assembly (1012).

As shown in FIGS. 37-40A, cycle response usage indicator (1016) includes a response actuator pawl (1028) rigidly mounted to shaft mount (1030) within a wheel ratchet (1036). Wheel ratchet (1036) is rotatable about shaft mount (1030) within housing (1018) and aligned with an indicia window (1040) for viewing the angler position of wheel ratchet (1036). Response actuator pawl (1028) is configured to direct rotation of wheel ratchet (1036) by moving from a retracted state to an elongated state upon being heated to the predetermined cleaning temperature as shown respectively in FIG. 38 and FIG. 39. To this end, response actuator pawl (1028) of the present example is formed from a first material, such as a first metal (1031), attached to a second material, such as a second metal (1032). The first and second metals (1031, 1032) have respective first and second thermal coefficients of expansion configured to collectively respond to heating such that response actuator pawl (1028) moves from the retracted state to the elongated state. More particularly, the first coefficient of thermal expansion of first metal (1031) is less than the second coefficient of thermal expansion of second metal (1032) such that second metal (1032) expands more than first metal (1031) upon heating to the predetermined cleaning temperature. Thereby, the greater expansion of second metal (1032) relative to first metal (1031) effectively rotates and straightens response actuator pawl (1028) for urging rotation of wheel ratchet (1036).

Figure 40A:
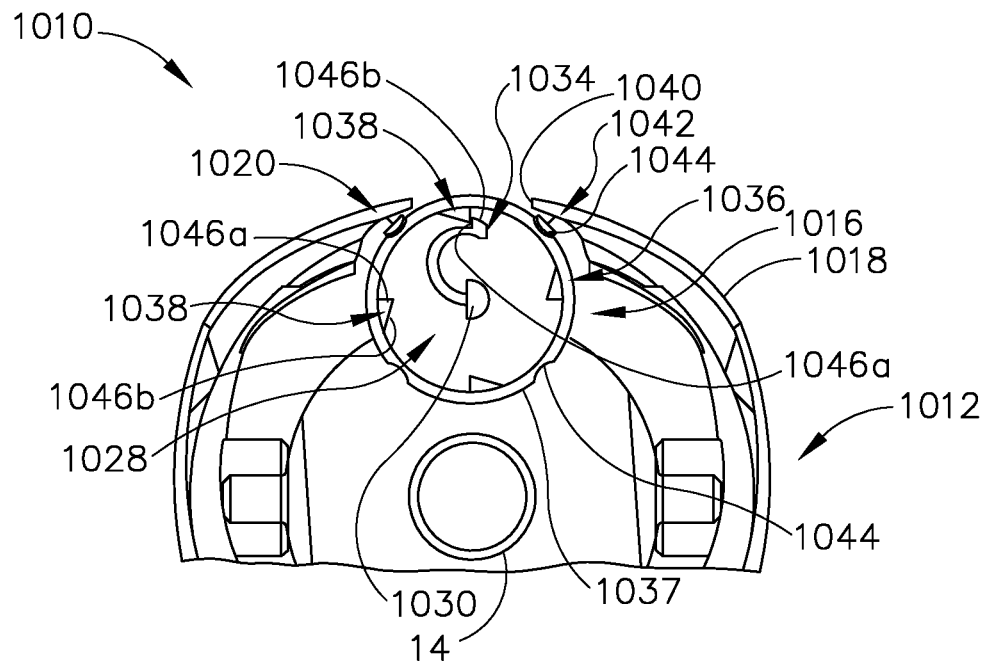
FIG. 40A depicts a cross-sectional view of the ultrasonic surgical instrument and the cycle response usage indicator taken along section line 40A-40A of FIG. 36 with the ratchet actuator in the unactuated state and indicating a first usage.
Figure 40B:
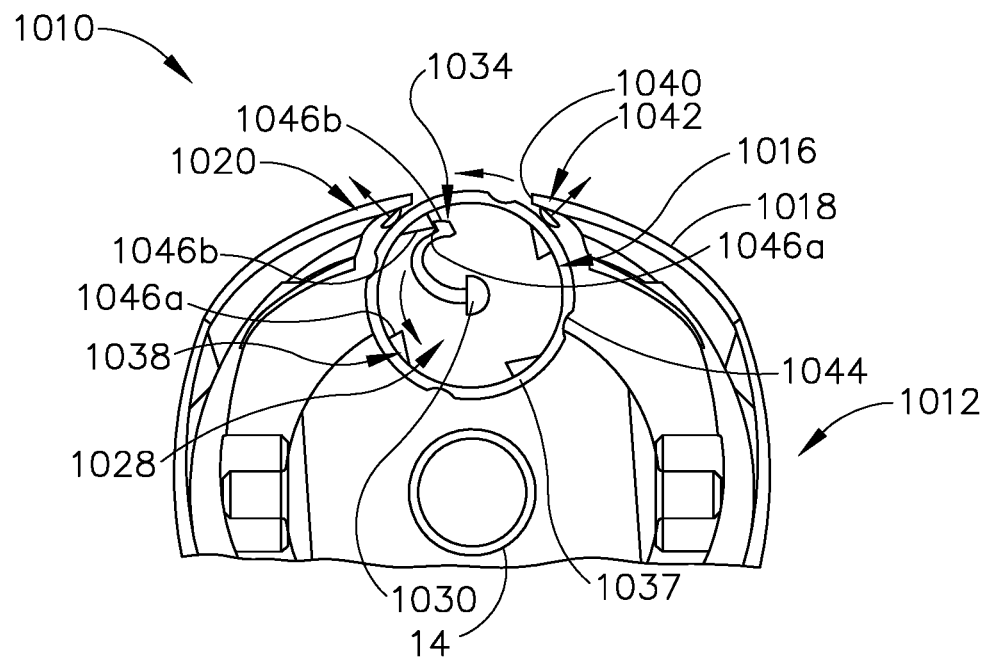
FIG. 40B depicts the cross-sectional view of the ultrasonic surgical instrument and the cycle response usage indicator similar to FIG. 40A, but showing the ratchet actuator actuating from the unactuated state toward the actuated state such that the cycle response usage indicator rotates toward an indication of a second usage.
Figure 40C:
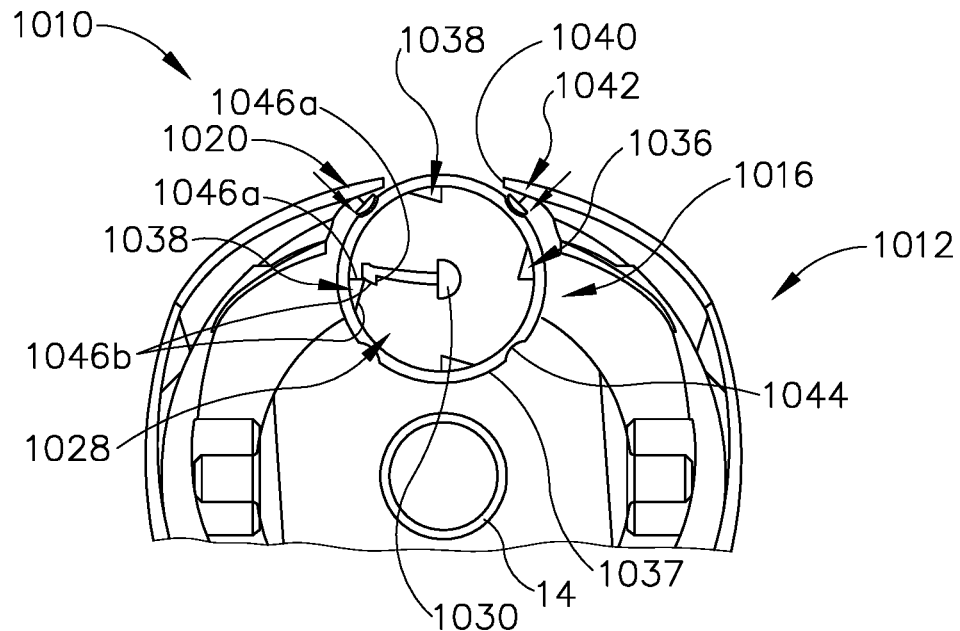
FIG. 40C depicts the cross-sectional view of the ultrasonic surgical instrument and the cycle response usage indicator similar to FIG. 40B, but showing the ratchet actuator in the actuated state such that the cycle response usage indicator indicates the second usage.

FIG. 40A shows response actuator pawl (1028) within wheel ratchet (1036). Response actuator pawl (1028) further includes an end tooth (1034), whereas wheel ratchet (1036) has a ring body (1037) and plurality of slip ratchet teeth (1038). Slip ratchet teeth (1038) extend inward from ring body (1037) and are positioned angularly about an inner surface of ring body (1037). In the retracted state, response actuator pawl (1028) engages an upper slip ratchet tooth (1038), but as cycle response usage indicator (1016) is heated to the predetermined cleaning temperature, response actuator pawl (1028) is configured to urge wheel ratchet (1036) counterclockwise toward the used state as shown in FIGS. 40B-40C. Cycle response usage indicator (1016) further includes an arrester (1042) to inhibit inadvertent clockwise or counterclockwise rotation. Arrester (1042) of the present example includes cooperating detents (1044) between housing (1018) and ring body (1037) to movably secure the angular position of wheel ratchet (1036) with sufficient force to inhibit such inadvertent rotation. In the present example, "clockwise" and "counterclockwise" refer to rotation of wheel ratchet (936) as viewed from a distal end of wheel ratchet (1036).

Figure 40D:
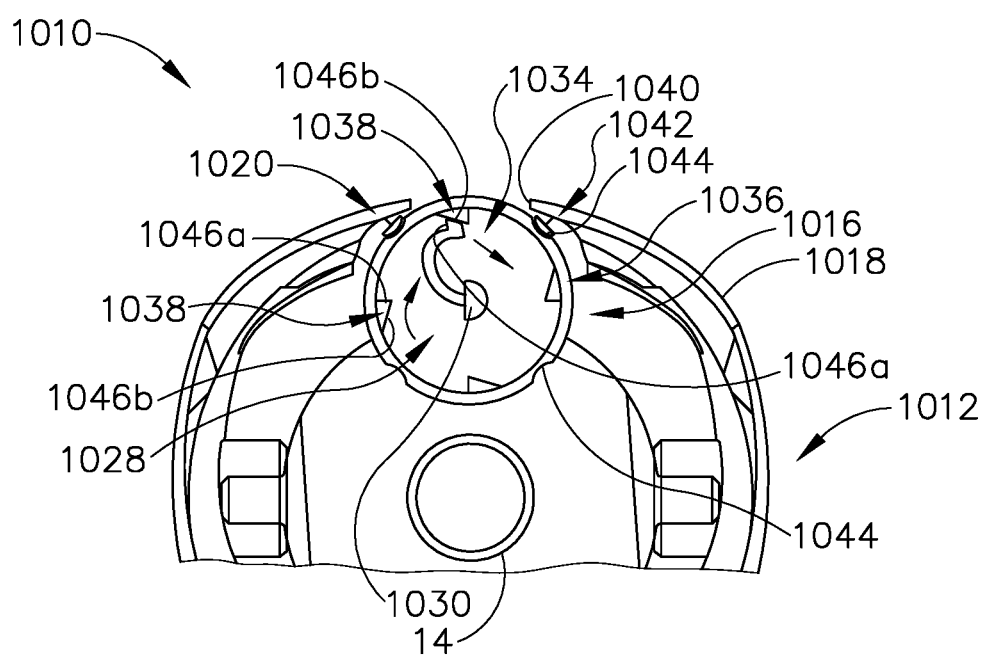
FIG. 40D depicts the cross-sectional view of the ultrasonic surgical instrument and the cycle response usage indicator similar to FIG. 40B, but showing the ratchet actuator returned from the actuated state to the unactuated state such that the cycle response usage indicator continues to indicate the second usage.

With respect to FIG. 40D, upon cooling of handle assembly (1012) from the predetermined cleaning temperature to the ambient temperature, response actuator pawl (1028) returns from the elongated state to the retracted state. However, because wheel ratchet (1036) is moveably secured via arrester (1042) as discussed above, wheel ratchet (1036) does not rotate clockwise with response actuator pawl (1028). Instead, end tooth (1034) of response actuator pawl (1028) slips counterclockwise along slip ratchet tooth (1038) until end tooth (1034) of response actuator pawl (1028) is again engaged with slip ratchet tooth (1038) for an additional cycle use. Such urging and slipping between end tooth (1034) and slip ratchet teeth (1038) is further aided by engagement and ramp portions (942a, 942b) of end tooth (1034) and slip ratchet teeth (938) similar to those discussed above in other examples herein. The angular position of wheel ratchet (1036) is thus configured to indicate to the clinician the use remaining state as it is rotated in the counterclockwise direction toward the used state by successive heating to the predetermined cleaning temperature.

Figure 36:
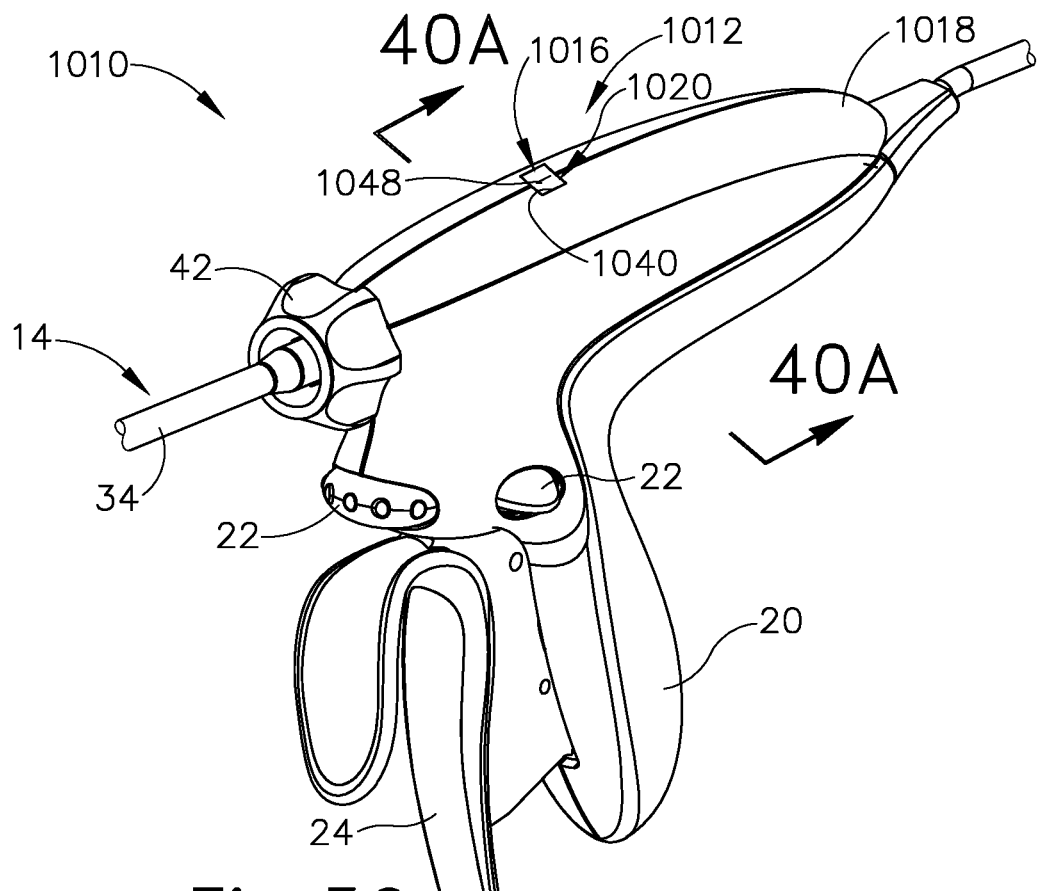
FIG. 36 depicts an enlarged perspective view of a tenth exemplary ultrasonic surgical instrument having a cycle response usage indicator for a shaft assembly and a handle assembly.

As briefly discussed above, indicia window (1040) provides clinician with visual identification of the angular position of wheel ratchet (1036). The relative angular position is recorded by a series of counter indices (1048), which are angularly positioned about wheel ratchet (1036) and increasing in the counterclockwise direction. The present example of counter indices (1048) includes clockwise increasing numbers "1," "2," "3," and "4," and are respectively configured to correspond to each replacement shaft assembly (14) used with handle assembly (1012) in relation to the rotational position of wheel ratchet (1036). For example, as shown in FIG. 36, a first counter indicia (1048) "1" transversely aligns through indicia window (1040) to indicate to the clinician that handle assembly (1012) is in its first use.

Successive heating to the predetermined cleaning temperature continue to rotate wheel ratchet (1036) until a fourth counter indicia (1048) "4" transversely aligns through indicia window (1040) to visually indicate the used state of handle assembly (1012). In addition, arrester (1042) may be further configured to inhibit connection of replacement shaft assemblies (1014) greater than the predetermined number of use cycles. Cycle response usage indicator (1016) is thereby configured to inhibit inadvertently using handle assembly (1212) beyond the predetermined number of use cycles. While the present example response actuator pawl (1028) is initially in the retracted state and straightens to the elongated state upon heating to the predetermined cleaning temperature, response actuator pawl (1028) may be alternatively configured to initially be in either the retracted or elongated states. Response actuator pawl (1028) may furthermore be configured to direct movement of wheel ratchet (1036) when heated or cooled. It will be appreciated that any combination of initial states of actuator pawl (1028) upon either heating or cooling may direct movement of actuator pawl (1028), and the invention is thus not intended to be unnecessarily limited to the particular states of actuator pawl (1028) shown and described herein.

In use, with respect to FIGS. 40A-40D, the clinician connects first replacement shaft assembly (14) to handle assembly (1012) and wheel ratchet (1036) aligns with the first indicia (1048) for indicating the first use to clinician. Following treatment of the patient, shaft assembly (14) is disconnected from handle assembly (1012) while ratcheted wheel ratchet (1036) remains stationary relative to housing (1018). Handle assembly (1012) is then prepped, such as by heating and cleaning handle assembly (1012) up to the predetermined cleaning temperature, for another surgical procedure. Heating handle assembly (1012) moves response actuator pawl (1028) from the retracted state to the elongated state to urge wheel ratchet (1036) counterclockwise another use cycle toward the used state. and another replacement shaft assembly (914) is connected to handle assembly (912). A second replacement shaft assembly (14) may then be connected to handle assembly (1012) while indicating the second use to the clinician. Such reuse continues in the remaining use state until wheel ratchet (1036) rotates counterclockwise to the used state to inhibit further attachment of additional replacement shaft assemblies (14).

K. Circuit Usage Indicator

FIGS. 41-45B illustrate an eleventh exemplary ultrasonic surgical instrument (1110) having a handle assembly (1112) configured to be operated up to a predetermined number of use cycles, shaft assembly (14) configured for a single use cycle of treatment, and a first circuit usage indicator (1116). With respect to FIGS. 41-42, first circuit usage indicator (1116) is integrated into a housing (1118) of handle assembly (1112) for recording and indicating each respective use cycle of handle assembly (1112) in a use remaining state to a used state. First circuit usage indicator (1116) has a housing portion (1120) is configured to respond to a state of use that occurs once per usage cycle to thereby direct first circuit usage indicator (1116) toward the used state. In the present example, first circuit usage indicator (1116) is directed toward the used state each time shaft assembly (14) is connected to handle assembly (1112). Once handle assembly (1112) has been repeatedly used with replacement shaft assemblies (14), first circuit usage indicator (1116) indicates the used state of handle assembly (1112) to the clinician. Such indication of first circuit usage indicator (1116) is visual as well as a lockout, which inhibits operation of handle assembly (1112).

Figure 43:
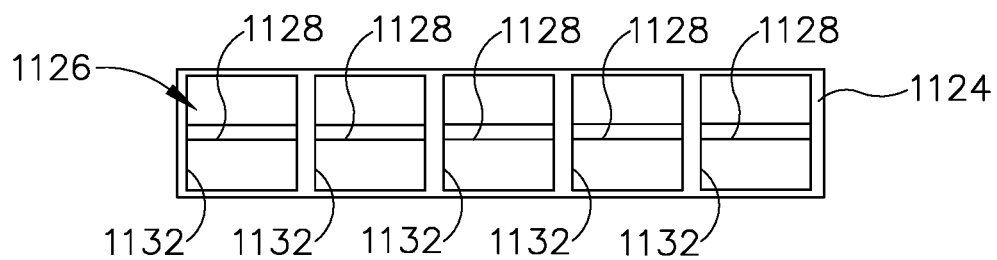
FIG. 43 depicts a side view of the circuit board of FIG. 42 with the plurality of use tabs hidden for greater clarity.

First circuit usage indicator (1116) includes a memory, such as an EEPROM (1122), and a circuit board (1124) having an electrical circuit (1126). EEPROM (1122) is configured to detect and record each instance that replacement shaft assemblies (14) are respectively connected to handle assembly (1112). Electrical circuit (1126) further includes a plurality of removable electrical connections (1128), such as wires, and a respective plurality of use tabs (1130) that cover openings (1132) on an outer surface of housing (1118) as shown in FIG. 43.

With respect to FIG. 42 and FIGS. 44A-45B, each use tab (1130) is pivotally connected to housing (1118) and further includes a wedge (1134) extending laterally into housing (1118) toward removable electrical connection (1128). With each use, the clinician manipulates one respective use tab (1130) inward through opening (1132) such that wedge (1134) breaks electrical connection (1124) for electrical removal from electrical circuit (1126). EEPROM (1122) adjusts electrical circuit (1126) based on each recorded connection of shaft assembly (14) to prevent electrical powering of ultrasonic transducer (26) handle assembly (1112) unless a subsequent use tab (1130) is depressed. EEPROM (1122) is thus configured to sense each respective electrical removal of use tabs (1130) and only allows electrical powering of ultrasonic transducer (26) after clinician removes electrical connection (1128) that correlates to the particular use cycle with replacement shaft assembly (14). For visual indication of use cycles, each use tab (1130) has a respective counter indicia (1136) that increases in the proximal direction with numbers "1," "2," "3," "4," and "5" and are respectively configured to correspond to each replacement shaft assembly (14). For example, a first counter indicia (1136) "1" indicates to the clinician that handle assembly (1212) is in its first use.

Successive connections of replacement shaft assemblies (14) continue to require the clinician to remove respective electrical portions (1128) via depression of use tabs (1130) until a fifth counter indicia (1136) "5" is depressed to visually indicate the used state of handle assembly (1112). In addition, EEPROM (1122) is further configured to inhibit further electrical powering of handle assembly (1112) with additional replacement shaft assemblies (14) greater than the predetermined number of use cycles. First circuit usage indicator (1116) is thereby configured to inhibit inadvertently using handle assembly (1112) beyond the predetermined number of use cycles.

In use, with respect to FIGS. 44A-44D, the clinician connects first replacement shaft assembly (14) to handle assembly (1112). Based on the recorded use cycles stored on EEPROM (1122), EEPROM prohibits electrical powering of handle assembly (1112) until the clinician depresses the respective use tab (1130) that correspond to the recorded use cycle and removes respective electrical connection (1128). Clinician depresses the respective use tab (1130) and thus treats the patient. Following treatment of the patient, shaft assembly (14) is disconnected from handle assembly (1112). Handle assembly (1112) is then prepped, such as by heating and/or sterilizing, for another surgical procedure and another replacement shaft assembly (14) is connected to handle assembly (1112). Such reuse continues in the remaining use state until all use tabs (1130) are depressed to the used state and EEPROM (1122) prohibits further electrical powering of handle assembly (1112).

Figure 41:
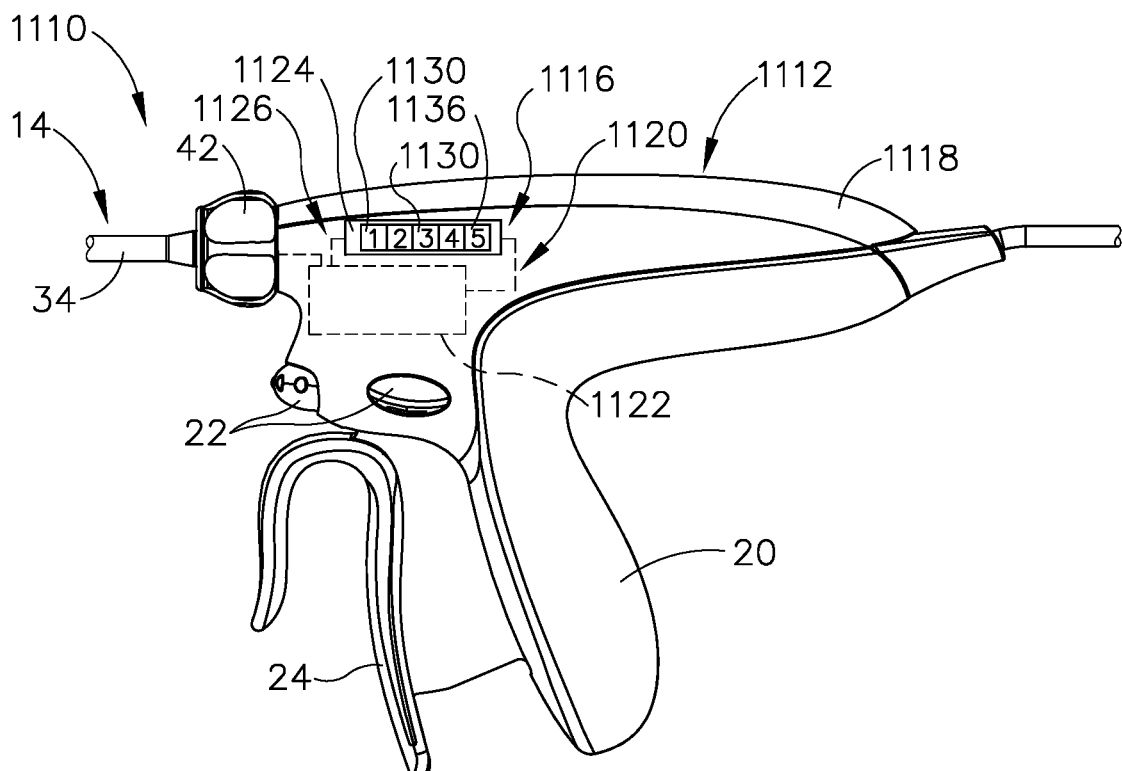
FIG. 41 depicts an enlarged side view of an eleventh exemplary ultrasonic surgical instrument having a first circuit usage indicator for a shaft assembly and a handle assembly.
Figure 42:
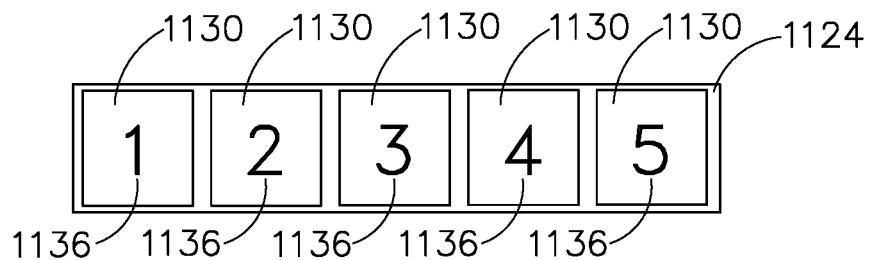
FIG. 42 depicts a side view of a circuit board of the first circuit usage indicator of FIG. 41 having a plurality of use tabs.

An alternative, second circuit usage indicator (1216) is shown in FIGS. 46A-47 for use in handle assembly (1112) of FIG. 41. Second circuit usage indicator (1216) is similar to first circuit usage indicator (1116) discussed above in most respects, but has a plurality of removable use tabs (1230) that include respective removable electrical connections (1228) of an electrical circuit (1226) integrated therein. Each removable use tab (1230) is thus configured to be pulled by the clinician and removed from housing (1118) to remove electrical connections (1228) for use by EEPROM (1122) as discussed above with respect to first circuit usage indicator (1116). Such tabs (1130, 1230) shown in FIGS. 41-47 may thus be movable between states for indication while remaining operatively connected to handle assembly (1112) or wholly removable from handle assembly (1112) for such indication.

L. First Switch Usage Indicator

FIGS. 48A-49B illustrate a twelfth exemplary ultrasonic surgical instrument (1310) having a handle assembly (1312) configured to be operated up to a predetermined number of use cycles, shaft assembly (14) configured for a single use cycle of treatment, and a first switch usage indicator (1316). First switch usage indicator (1316) is integrated into a housing (1318) of handle assembly (1312) for recording and indicating each respective use cycle of handle assembly (1312) in a use remaining state to a used state. First switch usage indicator (1316) has a housing portion (1320) is configured to respond to a state of use that occurs once per usage cycle to thereby direct first switch usage indicator (1316) toward the used state. In the present example, first switch usage indicator (1316) is directed toward the used state each time shaft assembly (14) is disconnected from handle assembly (1312). Once handle assembly (1312) has been repeatedly used with replacement shaft assemblies (14), first switch usage indicator (1316) indicates the used state of handle assembly (1312) to the clinician. Such indication of first switch usage indicator (1316) is visual as well as a lockout, which inhibits operation of handle assembly (1312).

First switch usage indicator (1316) includes a memory, such as an EEPROM (1322), an electromagnetic switch (1324), a pivotal blocker (1326), and a biasing element, such as a tension spring (1328), extending between a housing mount (1330) and pivotal blocker (1326), and a visual indicia (1332). EEPROM (1322) is configured to detect and record each instance that replacement shaft assemblies (14) are respectively connected to handle assembly (1312). Electromagnetic switch (1324) is electrically connected to EEPROM (1322) and configured to be activated by EEPROM (1322) to generate a magnetic field upon initiation of the used state. Pivotal blocker (1326) is biased by tension spring (1328) in a use remaining position and configured to be moved by the magnetic field from the use remaining position to a used position for releasing visual indicia (1332) as discussed below.

Figure 48A:
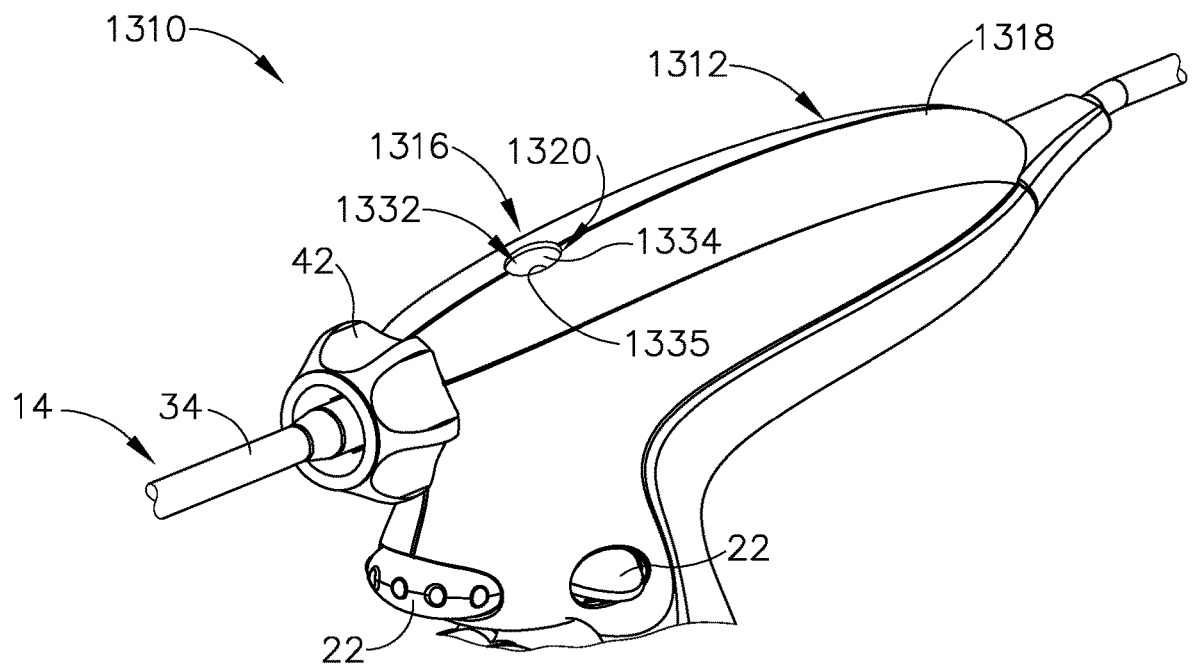
FIG. 48A depicts an enlarged perspective view of a twelfth exemplary ultrasonic surgical instrument having first a switch usage indicator for a shaft assembly and a handle assembly with the first switch usage indicator in a use remaining position.
Figure 48B:
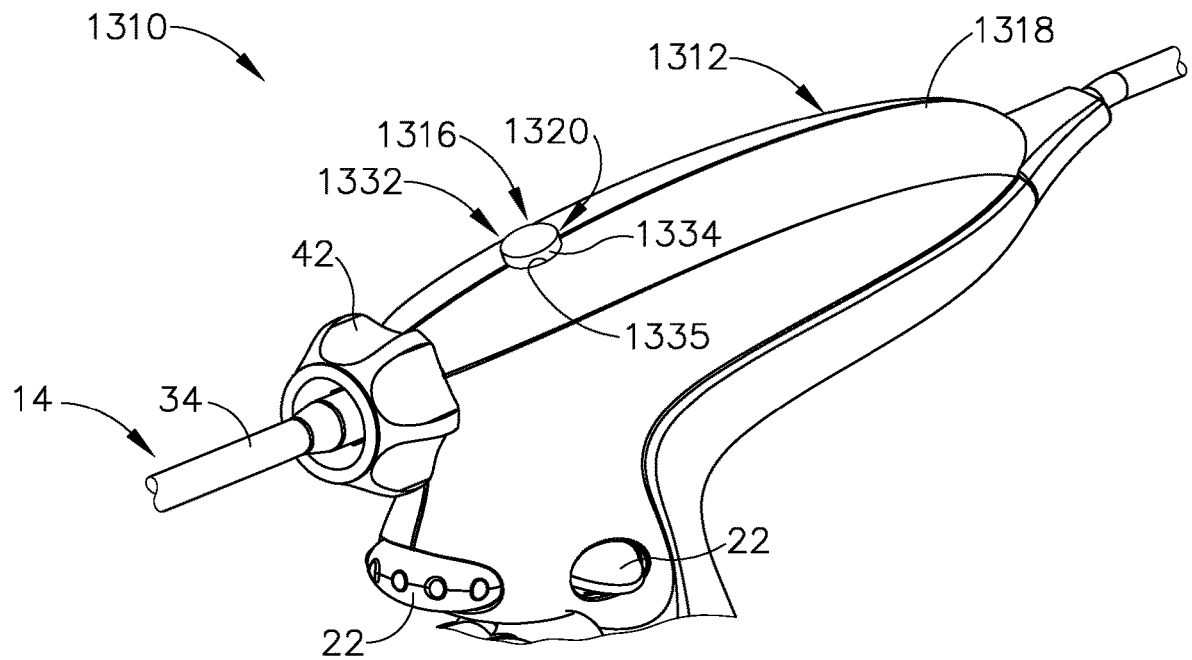
FIG. 48B depicts the enlarged perspective view of the ultrasonic surgical instrument and the first switch usage indicator similar to FIG. 48A, but showing the first switch usage indicator in a used position.

Visual indicia (1332) includes a cylindrical body (1334) biased upward by a biasing element, such as a compression spring (1336). Cylindrical body (1334) is transversely aligned with an indicia window (1335) in housing (1318)

and configured to move from a recessed position below indicia window (1335) to an extended position protruding through indicia window (1335). In the use remaining position, pivotal blocker (1326) releasably captures cylindrical body (1334) in the recessed position within housing (1318). More particularly, tension spring (1328) braces pivotal blocker (1326) to overcome the upward force on cylindrical body (1334) by compression spring (1336) and inhibit cylindrical body (1334) from rising upward to the extended position. Cylindrical body (1334) generally remains captured in the recessed position as shown in FIG. 48A and FIG. 48B by pivotal blocker (1326) throughout the use remaining state to indicate to the clinician that additional use cycles for replacement shaft assemblies (14) remain.

Once EEPROM (1322) senses removal of shaft assembly (14) on the final use cycle of handle assembly (1312), EEPROM (1322) operatively directs electromagnetic switch (1324) to generate the electromagnetic field. Electromagnetic field repels a magnetically responsive portion pivotal blocker (1326) and pivots pivotal blocker (1326) from the use remaining position to the used position to release upward movement of cylindrical body (1334) through indicia window (1335) a shown in FIG. 48B and FIG. 49B. In other words, the accumulation of the electromagnetic force and compression spring (1336) overcomes tension spring (1338) to move pivotal blocker to (1326) to the used position. In the present example, electromagnetic switch (1324) simply generates the electromagnetic field for a period of time sufficient to move pivotal blocker (1326) to the used position. Electromagnetic switch (1324) thus terminates the electric field following this period of time, but pivotal blocker (1326) remains in the used position.

Cylindrical body (1334) in the used state provides visual indication to the clinician that all use cycles for handle assembly (1312) are complete. Moreover, cylindrical body (1334) cannot be depressed back to into the housing (1318), because pivotal blocker (1326) cannot be reset to the use remaining position. Rather, compression spring (1336) will continue to urge cylindrical body (1334) upward for visual indication. No further electrical powering of electromagnetic switch (1324) is needed to provide the visual indication of the used state to the clinician. In addition, EEPROM (1322) is further configured to inhibit further electrical powering of handle assembly (1312) with additional replacement shaft assemblies (14) greater than the predetermined number of use cycles. First switch usage indicator (1316) is thereby configured to inhibit inadvertently using handle assembly (1312) beyond the predetermined number of use cycles. In the present example, the predetermined number of use cycles is five use cycles with five respective, replacement shaft assemblies (14).

Figure 49A:
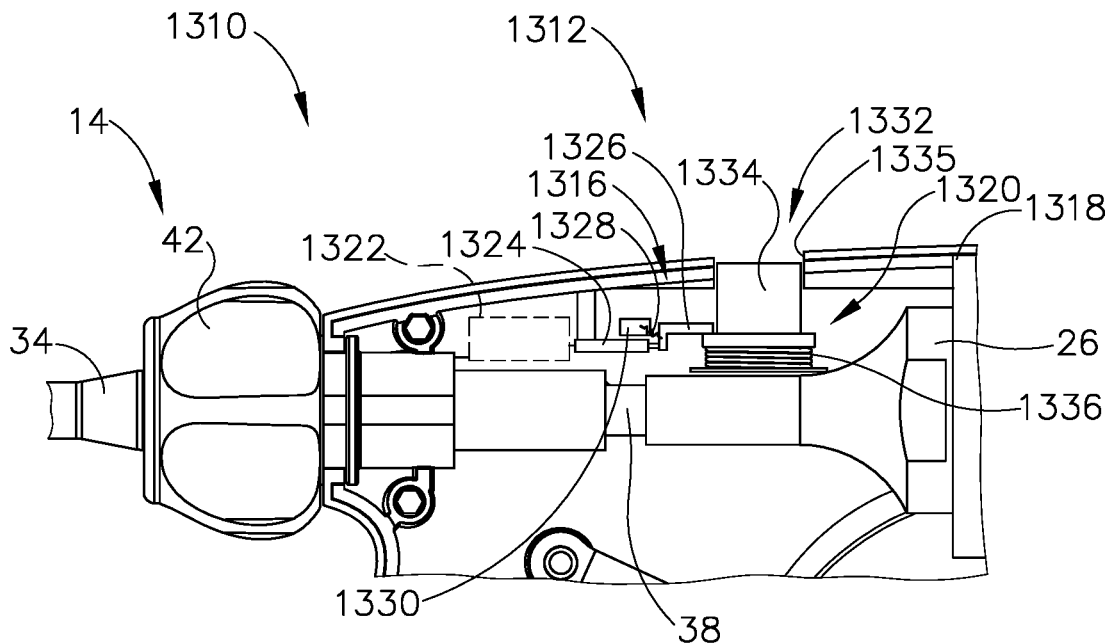
FIG. 49A depicts a side view of the ultrasonic surgical instrument and the first switch usage indicator of FIG. 48A having various features removed for more clearly showing the first switch usage indicator in the use remaining position.
Figure 49B:
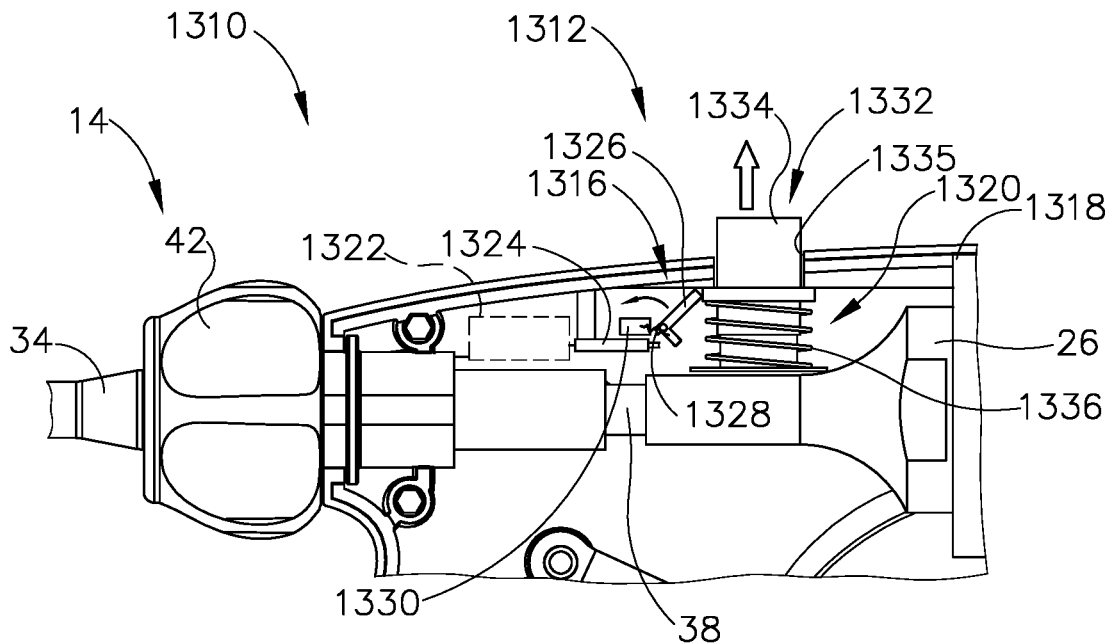
FIG. 49B depicts a side view of the ultrasonic surgical instrument and the first switch usage indicator of FIG. 48B having various features removed for more clearly showing the first switch usage indicator in the used position.

In use, with respect to FIGS. 49A-49B, the clinician connects first replacement shaft assembly (14) to handle assembly (1312). Following treatment of the patient, shaft assembly (14) is disconnected from handle assembly (1312) and EEPROM (1322) senses and records the disconnection of first replacement shaft assembly (14). Handle assembly (1312) is then prepped, such as by heating and/or sterilizing, for another surgical procedure and another replacement shaft assembly (14) is connected to handle assembly (1312). Such reuse continues in the remaining use state until EEPROM (1322) senses the disconnection of replacement shaft assembly (14) in the final use cycle of handle assembly (1312). EEPROM (1322) then initiates the used state by directing electromagnetic switch (1324) to generate the electromagnetic field and moving pivotal blocker (1326) from the use remaining position to the used position. Compression spring (1336) then urges cylindrical body (1334) upward through indicia window (1335) to indicate to the clinician that handle assembly (1312) is in the used state, while EEPROM (1322) inhibits further powering of handle assembly (1312) for use with another shaft assembly (14).

M. Second Switch Usage Indicator

Figure 50A:
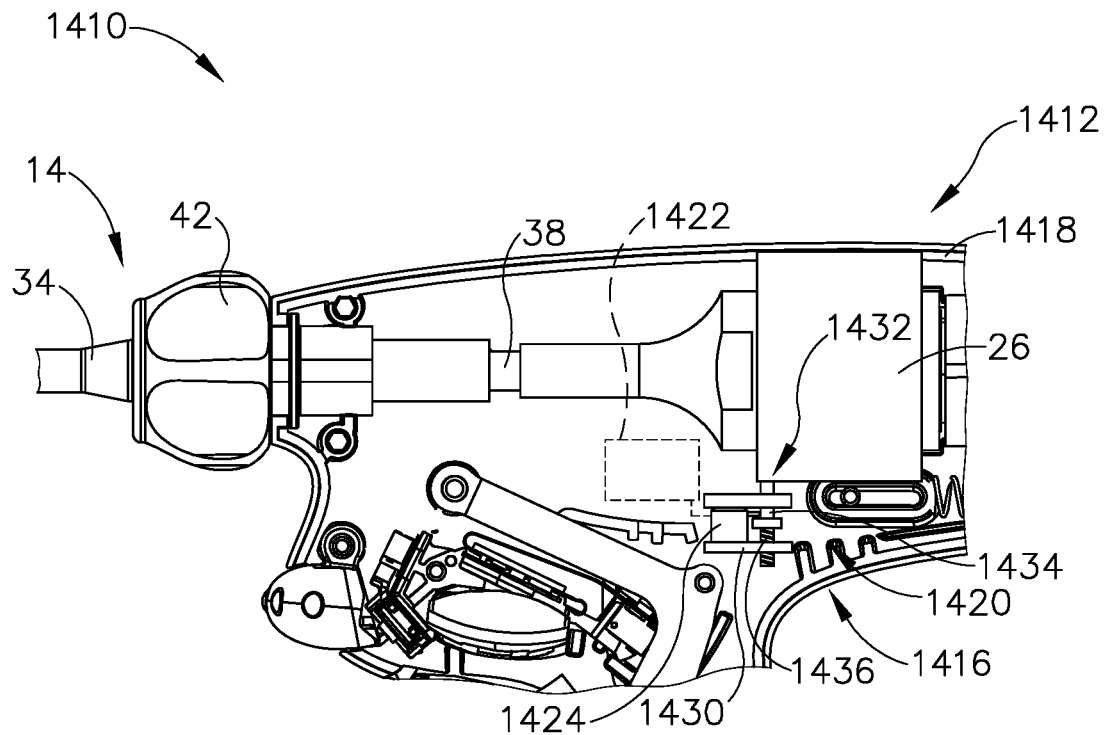
FIG. 50A depicts an enlarged side view of a thirteenth exemplary ultrasonic surgical instrument having various features hidden for more clearly showing a second switch usage indicator for a shaft assembly and a handle assembly with the second switch usage indicator in a use remaining position.
Figure 50B:
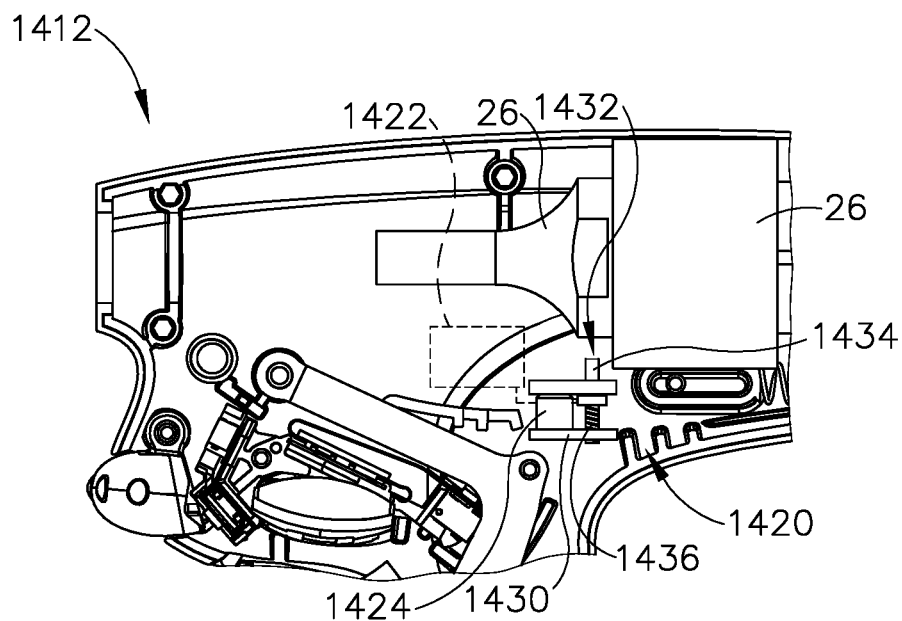
FIG. 50B depicts the enlarged side view of the ultrasonic surgical instrument and the second switch usage indicator similar FIG. 50A, but showing the second switch usage indicator in a used position.

FIGS. 50A-50B illustrate a thirteenth exemplary ultrasonic surgical instrument (1410) having a handle assembly (1412) configured to be operated up to a predetermined number of use cycles, shaft assembly (14) configured for a single use cycle of treatment, and a second switch usage indicator (1416). Second switch usage indicator (1416) is integrated into a housing (1418) of handle assembly (1412) for recording and indicating each respective use cycle of handle assembly (1412) in a use remaining state to a used state. Second switch usage indicator (1416) has a housing portion (1420) is configured to respond to a state of use that occurs once per usage cycle to thereby direct second switch usage indicator (1416) toward the used state. In the present example, second switch usage indicator (1416) is directed toward the used state each time shaft assembly (14) is disconnected from handle assembly (1412). Once handle assembly (1412) has been repeatedly used with replacement shaft assemblies (14), second switch usage indicator (1416) indicates the used state of handle assembly (1412) to the clinician. Such indication of second switch usage indicator (1316) is a lockout, which inhibits operation of handle assembly (1312).

Second switch usage indicator (1416) includes a memory, such as an EEPROM (1422), a solenoid switch (1424), and a translatable blocker (1426). EEPROM (1422) is configured to detect and record each instance that replacement shaft assemblies (14) are respectively connected to handle assembly (1412). Solenoid switch (1424) is electrically connected to EEPROM (1422) and configured to be activated by EEPROM (1422) from an extended state to a retracted state. Translatable blocker (1426) is biased by a compression spring (1436) from a use remaining position toward a used position for releasing movement of translatable blocker (1426) via solenoid switch (1424).

Generally, solenoid switch (1424) in the extended state is configured to releasably secure translatable blocker (1426) in the use remaining position until disconnection of shaft assembly (14) in the final use cycle. Actuating solenoid switch (1424) to the retracted state releases movement of translatable blocker (1426), which is positioned proximate to ultrasonic transducer (26). Translatable blocker (1426) in the used position extends upward into the longitudinal path of ultrasonic transducer (26) once disconnected from shaft assembly (14) to inhibit another, replacement shaft assembly (14) from being properly connected to ultrasonic transducer (26). The inability of the clinician to properly connect shaft assembly (14) to handle assembly (1412) in the used state indicates such used state to the clinician. Second switch usage indicator (1416) is thereby configured to inhibit inadvertently using handle assembly (1412) beyond the predetermined number of use cycles. In the present example, the predetermined number of use cycles is five use cycles with five respective, replacement shaft assemblies (14).

In use, with respect to FIGS. 50A-50B, the clinician connects first replacement shaft assembly (14) to handle assembly (1412). Following treatment of the patient, shaft assembly (14) is disconnected from handle assembly (1412) and EEPROM (1322) senses and records the disconnection of first replacement shaft assembly (14). Handle assembly (1412) is then prepped, such as by heating and/or sterilizing, for another surgical procedure and another replacement shaft assembly (14) is connected to handle assembly (1412). Such reuse continues in the remaining use state until EEPROM (1422) senses the disconnection of replacement shaft assembly (14) in the final use cycle of handle assembly (1412). EEPROM (1422) then initiates the used state by directing solenoid switch (1424) from the extended state to the retracted state to release translatable blocker (1426) from the use remaining position toward the used position. Compression spring (1436) then urges translatable blocker (1432) upward into the longitudinal path of ultrasonic transducer (26) to inhibit proper connection of shaft assembly (14) to handle assembly (1412) for indicating the used state to the clinician.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An ultrasonic surgical instrument, comprising: (a) a housing configured to removably connect to a shaft assembly; (b) an ultrasonic transducer supported by the housing and having a transducer connector configured to connect to a waveguide for acoustically connecting the ultrasonic transducer to the waveguide, wherein the ultrasonic transducer is configured to be operated up to a predetermined number of use cycles; and (c) an integrated usage indicator operatively connected to the housing and including a used state indicator, wherein the used state indicator is configured to indicate to a user in a used state when the ultrasonic transducer has been operated at least the predetermined number of use cycles for limiting usage of the ultrasonic transducer to the predetermined number of use cycles.

Example 2

The ultrasonic surgical instrument of Example 1, wherein the integrated usage indicator is configured to inhibit activation of the ultrasonic transducer with the shaft assembly attached therewith for inhibiting usage of the ultrasonic transducer greater than the predetermined number of use cycles.

Example 3

The ultrasonic surgical instrument of Example 2, wherein the used state indicator is configured to inhibit the shaft assembly from being connected to the housing when the ultrasonic transducer has been operated at least the predetermined number of use cycles.

Example 4

The ultrasonic surgical instrument of Example 1, wherein the used state indicator is configured to inhibit the waveguide from being acoustically connected to the ultrasonic transducer when the ultrasonic transducer has been operated at least the predetermined number of use cycles.

Example 5

The ultrasonic surgical instrument of Example 1, wherein the integrated usage indicator has a housing portion, and wherein the housing portion of the integrated usage indicator is configured to cooperate with the shaft assembly being introduced into connection with the housing to thereby direct the integrated usage indicator toward the used state.

Example 6

The ultrasonic surgical instrument of Example 5, further comprising a shaft assembly having a shaft portion of the integrated usage indicator configured to removably connect with the housing portion of the integrated usage indicator, and wherein the shaft portion of the integrated usage indicator is configured to direct the housing portion of the integrated usage indicator toward the used state upon connection therewith.

Example 7

The ultrasonic surgical instrument of Example 5, further comprising a shaft assembly having a shaft portion of the integrated usage indicator configured to removably connect with the housing portion of the integrated usage indicator, and wherein the shaft portion of the integrated usage indicator is configured to direct the housing portion of the integrated usage indicator toward the used state upon disconnection therefrom.

Example 8

The ultrasonic surgical instrument of Example 1, wherein the integrated usage indicator has a housing portion, wherein the housing portion of the integrate usage indicator is configured to increase in temperature up to a predetermined temperature, and wherein the housing portion of the integrate usage indicator is configured to be directed toward the used state upon increasing in temperature to the predetermined temperature.

Example 9

The ultrasonic surgical instrument of Example 1, wherein the integrated usage indicator further includes a catch connected to the housing, wherein the catch is configured to capture a detachable feature on the shaft assembly for indicating at least one of the predetermined number of use cycles.

Example 10

The ultrasonic surgical instrument of Example 1, wherein the integrated usage indicator further includes a ratchet having the used state indicator thereon, wherein the ratchet is configured to be directed in a first direction toward the used state upon connection of the housing with the shaft assembly, and wherein the ratchet is ratcheted to inhibit the ratchet from moving in a second direction opposite from the first direction.

Example 11

The ultrasonic surgical instrument of Example 10, wherein the ratchet is a wheel ratchet and the first and second directions are respectively a first rotational direction and a second rotational direction.

Example 12

The ultrasonic surgical instrument of Example 10, further comprising a shaft assembly having an actuator, wherein the actuator is configured to urge the ratchet in the first direction upon connection of the shaft assembly with the housing.

Example 13

The ultrasonic surgical instrument of Example 1, wherein the integrated usage indicator further includes a ratchet having the used state indicator thereon, wherein the ratchet is configured to be directed in a first direction toward the used state upon acoustic connection of the waveguide to the ultrasonic transducer, wherein the ratchet is ratcheted to inhibit the ratchet from moving in a second direction opposite from the first direction, and wherein the ultrasonic transducer has an actuator configured to urge the ratchet in the first direction upon acoustically connecting the wave guide to the ultrasonic transducer.

Example 14

The ultrasonic surgical instrument of Example 1, wherein the integrated usage indicator further includes an electrical circuit having a plurality of removable electrical connections, wherein each of the plurality of removable electrical connections is configured to be removed with each respective predetermined number of use cycles until indication of the used state indicator.

Example 15

The ultrasonic surgical instrument of Example 1, wherein the integrated usage indicator further includes a blocker configured to be driven from a first position to a second position upon the predetermined number of use cycles to thereby move the used state indicator to the used state.

Example 16

An ultrasonic surgical instrument, comprising: (a) a shaft assembly extending from a distal end portion to a proximal end portion and including: (i) an end effector extending distally from the distal end portion, and (ii) an acoustic waveguide extend from the distal end portion to the proximal end portion, wherein the wave guide includes a proximally extending first threaded connection; (b) a housing configured to removably connect to the proximal end portion of the shaft assembly; (c) an ultrasonic transducer supported by the housing and having a second threaded connector configured to connect to the first threaded connector of the acoustic waveguide for acoustically connecting the ultrasonic transducer to the waveguide, wherein the ultrasonic transducer is configured to be operated up to a predetermined number of use cycles; and (d) an integrated usage indicator operatively connected to the housing and including: (i) a use remaining indicator configured to indicate to a clinician in a use remaining state when the ultrasonic transducer has been operated less than the predetermined number of use cycles, (ii) a used state indicator configured to indicate to the clinician in a used state when the ultrasonic transducer has been operated the predetermined number of use cycles, and (iii) an arrester configured to inhibit connection of the shaft assembly when the used state indicator is in the used state for limiting usage of the ultrasonic transducer to the predetermined number of use cycles.

Example 17

The ultrasonic surgical instrument of Example 16, wherein the integrated usage indicator further includes a ratchet having the used state indicator thereon, wherein the ratchet is configured to be directed in a first direction toward the used state upon connection of the housing with the shaft assembly, and wherein the ratchet is ratcheted to inhibit the ratchet from moving in a second direction opposite from the first direction.

Example 18

A method of indicating a used state of an ultrasonic surgical instrument, the ultrasonic surgical instrument including: (a) a housing configured to removably connect to a shaft assembly, (b) an ultrasonic transducer supported by the housing and having a transducer connector configured to connect to a waveguide for acoustically connecting the ultrasonic transducer to the waveguide, wherein the ultrasonic transducer is configured to be operated up to a predetermined number of use cycles, and (c) an integrated usage indicator operatively connected to the housing and including a used state indicator, wherein the used state indicator is configured to indicate to a clinician in a used state when the ultrasonic transducer has been operated at least the predetermined number of use cycles for limiting usage of the ultrasonic transducer to the predetermined number of use cycles, the method comprising: (a) connecting the shaft assembly to the housing; (b) directing the integrated usage indicator from a use remaining state toward the used state; and (c) indicating the used state with the used state indicator to the clinician when the integrated usage indicator is in the used state.

Example 19

The method of Example 18, wherein directing the integrated usage indicator further includes rotating a wheel ratchet in a first direction and inhibiting rotation of the wheel ratchet in a second direction, wherein the first direction is opposite the second direction.

Example 20

The method of Example 18, further comprising inhibiting connection of the shaft assembly to the housing when the integrated usage indicator is in the used state.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pat. No. 8,844,789, entitled "Automated End Effector Component Reloading System for Use with a Robotic System," issued Sep. 30, 2014, the disclosure of which is incorporated by reference herein; U.S. Pat. No. 8,820,605, entitled "Robotically-Controlled Surgical Instruments," issued Sep. 2, 2014, the disclosure of which is incorporated by reference herein; U.S. Pat. No. 8,616,431, entitled "Shiftable Drive Interface for Robotically-Controlled Surgical Tool," issued Dec. 31, 2013, the disclosure of which is incorporated by reference herein; U.S. Pat. No. 8,573,461, entitled "Surgical Stapling Instruments with Cam-Driven Staple Deployment Arrangements," issued Nov. 5, 2013, the disclosure of which is incorporated by reference herein; U.S. Pat. No. 8,602,288, entitled "Robotically-Controlled Motorized Surgical End Effector System with Rotary Actuated Closure Systems Having Variable Actuation Speeds," issued Dec. 10, 2013, the disclosure of which is incorporated by reference herein; U.S. Pat. No. 9,301,759, entitled "Robotically-Controlled Surgical Instrument with Selectively Articulatable End Effector," issued Apr. 5, 2016, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An ultrasonic surgical instrument, comprising:
   (a) a housing configured to removably connect to a shaft assembly;
   (b) an ultrasonic transducer supported by the housing and having a transducer connector configured to connect to a waveguide for acoustically connecting the ultrasonic transducer to the waveguide, wherein the ultrasonic transducer is configured to be operated up to a predetermined number of use cycles; and
   (c) an integrated usage indicator operatively connected to the housing and including a used state indicator, wherein the used state indicator is configured to indicate to a clinician in a used state when the ultrasonic transducer has been operated at least the predetermined number of use cycles for limiting usage of the ultrasonic transducer to the predetermined number of use cycles, wherein the used state indicator is configured to inhibit the waveguide from being acoustically connected to the ultrasonic transducer when the ultrasonic transducer has been operated at least the predetermined number of use cycles.

2. The ultrasonic surgical instrument of claim 1, wherein the integrated usage indicator is configured to inhibit activation of the ultrasonic transducer with the shaft assembly attached therewith for inhibiting usage of the ultrasonic transducer greater than the predetermined number of use cycles.

3. The ultrasonic surgical instrument of claim 2, wherein the used state indicator is configured to inhibit the shaft assembly from being connected to the housing when the ultrasonic transducer has been operated at least the predetermined number of use cycles.

4. The ultrasonic surgical instrument of claim 1, wherein the integrated usage indicator has a housing portion, and wherein the housing portion of the integrated usage indicator is configured to cooperate with the shaft assembly being introduced into connection with the housing to thereby direct the integrated usage indicator toward the used state.

5. The ultrasonic surgical instrument of claim 4, further comprising a shaft assembly having a shaft portion of the integrated usage indicator configured to removably connect with the housing portion of the integrated usage indicator, and wherein the shaft portion of the integrated usage indicator is configured to direct the housing portion of the integrated usage indicator toward the used state upon connection therewith.

6. The ultrasonic surgical instrument of claim 4, further comprising a shaft assembly having a shaft portion of the integrated usage indicator configured to removably connect with the housing portion of the integrated usage indicator, and wherein the shaft portion of the integrated usage indicator is configured to direct the housing portion of the integrated usage indicator toward the used state upon disconnection therefrom.

7. The ultrasonic surgical instrument of claim 1, wherein the integrated usage indicator has a housing portion, wherein the housing portion of the integrate usage indicator is configured to increase in temperature up to a predetermined temperature, and wherein the housing portion of the integrate usage indicator is configured to be directed toward the used state upon increasing in temperature to the predetermined temperature.

8. The ultrasonic surgical instrument of claim 1, wherein the integrated usage indicator further includes a catch connected to the housing, wherein the catch is configured to capture a detachable feature on the shaft assembly for indicating at least one of the predetermined number of use cycles.

9. The ultrasonic surgical instrument of claim 1, wherein the integrated usage indicator further includes a ratchet having the used state indicator thereon, wherein the ratchet is configured to be directed in a first direction toward the used state upon connection of the housing with the shaft assembly, and wherein the ratchet is ratcheted to inhibit the ratchet from moving in a second direction opposite from the first direction.

10. The ultrasonic surgical instrument of claim 9, wherein the ratchet is a wheel ratchet and the first and second directions are respectively a first rotational direction and a second rotational direction.

11. The ultrasonic surgical instrument of claim 9, further comprising a shaft assembly having an actuator, wherein the actuator is configured to urge the ratchet in the first direction upon connection of the shaft assembly with the housing.

12. The ultrasonic surgical instrument of claim 1, wherein the integrated usage indicator further includes a ratchet having the used state indicator thereon, wherein the ratchet is configured to be directed in a first direction toward the used state upon acoustic connection of the waveguide to the ultrasonic transducer, wherein the ratchet is ratcheted to inhibit the ratchet from moving in a second direction opposite from the first direction, and wherein the ultrasonic transducer has an actuator configured to urge the ratchet in the first direction upon acoustically connecting the wave guide to the ultrasonic transducer.

13. The ultrasonic surgical instrument of claim 1, wherein the integrated usage indicator further includes an electrical circuit having a plurality of removable electrical connections, wherein each of the plurality of removable electrical connections is configured to be removed with each respective predetermined number of use cycles until indication of the used state indicator.

14. The ultrasonic surgical instrument of claim 1, wherein the integrated usage indicator further includes a blocker configured to be driven from a first position to a second position upon the predetermined number of use cycles to thereby move the used state indicator to the used state.

15. An ultrasonic surgical instrument, comprising:
   (a) a shaft assembly extending from a distal end portion to a proximal end portion and including:
      (i) an end effector extending distally from the distal end portion, and
      (ii) an acoustic waveguide extending from the distal end portion to the proximal end portion, wherein the wave guide includes a proximally extending first threaded connection;
   (b) a housing configured to removably connect to the proximal end portion of the shaft assembly;
   (c) an ultrasonic transducer supported by the housing and having a second threaded connector configured to connect to the first threaded connector of the acoustic waveguide for acoustically connecting the ultrasonic transducer to the waveguide, wherein the ultrasonic transducer is configured to be operated up to a predetermined number of use cycles; and (d) an integrated usage indicator operatively connected to the housing and including:
   (i) a use remaining indicator configured to indicate to a clinician in a use remaining state when the ultrasonic transducer has been operated less than the predetermined number of use cycles,
   (ii) a used state indicator configured to indicate to the clinician in a used state when the ultrasonic transducer has been operated the predetermined number of use cycles, and
   (iii) an arrester configured to inhibit mechanical connection of the proximal end portion of the shaft assembly to the housing when the used state indicator is in the used state for limiting usage of the ultrasonic transducer to the predetermined number of use cycles.

16. The ultrasonic surgical instrument of claim 15, wherein the integrated usage indicator further includes a ratchet having the used state indicator thereon, wherein the ratchet is configured to be directed in a first direction toward the used state upon connection of the housing with the shaft assembly, and wherein the ratchet is ratcheted to inhibit the ratchet from moving in a second direction opposite from the first direction.

17. The ultrasonic surgical instrument of claim 15, wherein the arrester is further configured to inhibit inadvertent movement of the used state indicator.

18. A method of indicating a used state of an ultrasonic surgical instrument, the ultrasonic surgical instrument including: (a) a housing configured to removably connect to a shaft assembly, (b) an ultrasonic transducer supported by the housing and having a transducer connector configured to connect to a waveguide for acoustically connecting the ultrasonic transducer to the waveguide, wherein the ultrasonic transducer is configured to be operated up to a predetermined number of use cycles, and (c) an integrated usage indicator operatively connected to the housing and including a ratchet and a used state indicator, wherein the used state indicator is configured to indicate to a clinician in a used state when the ultrasonic transducer has been operated at least the predetermined number of use cycles for limiting usage of the ultrasonic transducer to the predetermined number of use cycles, the method comprising:
   (a) connecting the shaft assembly to the housing;
   (b) ratcheting the ratchet of the integrated usage indicator from a use remaining state toward the used state;
   (c) indicating the used state with the used state indicator to the clinician when the integrated usage indicator is in the used state.

19. The method of claim 18, wherein ratcheting the integrated usage indicator further includes rotating a wheel ratchet in a first direction and inhibiting rotation of the wheel ratchet in a second direction, wherein the first direction is opposite the second direction.

20. The method of claim 18, further comprising inhibiting connection of the shaft assembly to the housing when the integrated usage indicator is in the used state.

* * * * *